(12) United States Patent
Okamura et al.

(10) Patent No.: US 11,219,672 B2
(45) Date of Patent: Jan. 11, 2022

(54) THERAPEUTIC AGENT FOR CANCER WHICH COMPRISES COMBINATION OF IL-18 AND MOLECULE-TARGETING ANTIBODY

(71) Applicants: Haruki Okamura, Osaka (JP); Kyosuke Yamanishi, Hyogo (JP); Yoshimasa Tanaka, Nagasaki (JP); MEDICAL RESEARCH AND DEVELOPMENT CORPORATION, Aichi (JP); FOUNDATION FOR BIOMEDICAL RESEARCH AND INNOVATION AT KOBE, Hyogo (JP)

(72) Inventors: Haruki Okamura, Hyogo (JP); Kyosuke Yamanishi, Hyogo (JP); Wen Li, Hyogo (JP)

(73) Assignees: Haruki Okamura, Osaka (JP); Kyosuke Yamanishi, Hyogo (JP); Yoshimasa Tanaka, Nagasaki (JP); Medical Research and Development Corporation, Aichi (JP); Foundation for Biomedical Research and Innovation, Hyogo (JP)

( * ) Notice: Subject to any disclaimer, the term of this patent is extended or adjusted under 35 U.S.C. 154(b) by 322 days.

(21) Appl. No.: 15/501,760

(22) PCT Filed: Aug. 7, 2015

(86) PCT No.: PCT/JP2015/072505
§ 371 (c)(1),
(2) Date: Feb. 3, 2017

(87) PCT Pub. No.: WO2016/021720
PCT Pub. Date: Feb. 11, 2016

(65) Prior Publication Data
US 2017/0224791 A1    Aug. 10, 2017

(51) Int. Cl.
*A61K 39/00* (2006.01)
*A61K 38/00* (2006.01)
*A61K 39/395* (2006.01)
*A61K 38/20* (2006.01)
*C07K 16/24* (2006.01)
*C07K 16/28* (2006.01)

(52) U.S. Cl.
CPC .......... *A61K 39/0005* (2013.01); *A61K 38/00* (2013.01); *A61K 38/20* (2013.01); *A61K 39/395* (2013.01); *C07K 16/244* (2013.01); *C07K 16/2812* (2013.01); *A61K 2039/6056* (2013.01)

(58) Field of Classification Search
CPC .. A61K 39/0005; A61K 38/00; A61K 39/395; A61K 38/20; A61K 2039/6056; A61K 39/39558; A61K 2039/505; C07K 16/244; C07K 16/2812; A61P 43/00; A61P 35/02; A61P 35/00; A61P 21/00; A61P 17/00; A61P 15/00; A61P 1/04
See application file for complete search history.

(56) References Cited

U.S. PATENT DOCUMENTS

| | | | |
|---|---|---|---|
| 8,121,365 B2 * | 2/2012 | Pinard | G01N 33/53 382/128 |
| 2006/0110383 A1 | 5/2006 | Honjo et al. | |
| 2007/0041981 A1 * | 2/2007 | Howard | A61K 39/39 424/155.1 |
| 2008/0274078 A1 | 11/2008 | Haskova et al. | |
| 2009/0035258 A1 | 2/2009 | Haskova et al. | |
| 2009/0074787 A1 * | 3/2009 | Gomez-Navarro | A61P 43/00 424/142.1 |
| 2010/0055102 A1 | 3/2010 | Langermann | |
| 2010/0111945 A1 | 5/2010 | Haskova et al. | |
| 2010/0196310 A1 | 8/2010 | Haskova et al. | |
| 2011/0081341 A1 | 4/2011 | Honjo et al. | |
| 2011/0159023 A1 | 6/2011 | Langermann | |
| 2011/0195068 A1 | 8/2011 | Langermann | |
| 2011/0223188 A1 | 9/2011 | Langermann | |
| 2011/0287009 A1 * | 11/2011 | Scheer | C07K 16/244 424/136.1 |
| 2012/0114648 A1 | 5/2012 | Langermann | |
| 2012/0114649 A1 | 5/2012 | Langermann | |
| 2013/0230514 A1 | 9/2013 | Langermann | |
| 2014/0227262 A1 | 8/2014 | Langermann | |

(Continued)

FOREIGN PATENT DOCUMENTS

| | | |
|---|---|---|
| CA | 2647282 | 10/2007 |
| CN | 102203132 | 9/2011 |
| EP | 0692536 | 1/1996 |

(Continued)

OTHER PUBLICATIONS

Kim et al. Structural requirements of six naturally occurring isoforms of the IL-18 binding protein to inhibit IL-18. (PNAS 97(3): 1190-1195, Feb. 1, 2000).*

(Continued)

*Primary Examiner* — Alana Harris Dent

(74) *Attorney, Agent, or Firm* — Casimir Jones, S.C.; Tanya A. Arenson

(57) ABSTRACT

A cancer therapeutic agent according to an embodiment of the present invention contains, as active ingredients, IL-18 and one or more antibodies selected from the group consisting of an anti-PD-L1 antibody, an anti-PD-1 antibody, an anti-PD-L2 antibody, an anti-CTLA-4 antibody, an anti-CD25 antibody, an anti-CD33 antibody, and an anti-CD52 antibody.

4 Claims, 38 Drawing Sheets
Specification includes a Sequence Listing.

(56) References Cited

U.S. PATENT DOCUMENTS

2014/0294765 A1* 10/2014 Cojocaru ............... C07K 16/28
424/85.2

FOREIGN PATENT DOCUMENTS

| EP | 0712931 | 5/1996 | |
|---|---|---|---|
| EP | 0767178 | 4/1997 | |
| EP | 1537878 | 6/2005 | |
| JP | 2004-512005 | 4/2004 | |
| JP | 2006-528627 | 12/2006 | |
| JP | 2007-277242 | 10/2007 | |
| JP | 2008-539249 | 11/2008 | |
| JP | 2009-544582 | 12/2009 | |
| JP | 2010-522239 | 7/2010 | |
| JP | 2013-525373 | 6/2013 | |
| KR | 2010-0014530 | 2/2010 | |
| WO | 97/02441 | 1/1997 | |
| WO | 01/14424 | 3/2001 | |
| WO | 01/098455 | 12/2001 | |
| WO | 2004/004771 | 1/2004 | |
| WO | 2005/009466 | 2/2005 | |
| WO | 2006/116423 | 11/2006 | |
| WO | 2008/006895 | 1/2008 | |
| WO | 2008/118733 | 10/2008 | |
| WO | 2008/118736 | 10/2008 | |
| WO | WO-2008118736 A1 * | 10/2008 | ............ A61P 37/04 |
| WO | 2011/133819 | 10/2011 | |
| WO | 2013/173223 | 11/2013 | |

OTHER PUBLICATIONS

NCBI, IL18 interleukin 18 [*Homo sapeins* (human)], 6 pages (published Jul. 16, 2019).*
Ma et al. IL-18 augments efficacy of anti-CTLA4 and /or anti-PD-L1 antibodies against peritoneally disseminated tumors in mice. The 43th Meeting of Japanese Society for Immunology 43: p. 36, Abstract 1-B-W2-10-P, Dec. 10, 2014-Dec. 12, 2014.*
Okamura et al. Effect of Combination of IL-18 and Immune Checkpoint Inhibitors on Peritoneal Dissemination of Tumor Cells. Grants-In-Aide for Scientific Research, Research Results Report, 2017.*
Search Report for EP Patent Application No. 15830617.5, dated Aug. 1, 2017.
Ma, Z. et al: "Augmentation of Immune Checkpoint . . . ," Clinical Cancer Research, vol. 22, No. 12, Jan. 11, 2016 (Jan. 11, 2016), pp. 2969-2980, XP055392162,US ISSN: 1078-0432, DOI: 10.1158/1078-0432.CCR-15-1655.
Franks, H.A. et al: "New Anticancer Immunotherapies", Anticancer Research, vol. 32, Jan. 1, 2012 (Jan. 1, 2012), pp. 2439-2454, XP055392336.
Wu, L. et al: "CTLA-4 Blockade Expands Infiltrating . . . ", Molecular Cancer Therapeutics, vol. 11, No. 8, Aug. 1, 2012 (Aug. 1, 2012), pp. 1809-1819, XP055392333, US ISSN: 1535-7163, DOI: 10.1158/1535-7163. MCT-11-10.
Zitvogel, L. et al: "Inflammasomes in carcinogenesis . . . ", Nature Immunology, vol. 13, No. 4, Apr. 1, 2012 (Apr. 1, 2012), pp. 343-351, XP055091179, ISSN: 1529-2908, DOI: 10.1038/ni.222.
Alagkiozidis, I. et al: "Time-dependent cytotoxic . . . ", Journal of Translational Medicine, Biomed Central, London, GB, vol. 9, No. 1, May 25, 2011 (May 25, 2011), p. 77, XP021100804, ISSN: 1479-5876, DOI: '10.1186/1479-5876-9-77.
Nishimura H. et al. "Facilation of Beta Selection and Modification of Positive Selection in the Thymus of PD-1-deficient Mice" J. Exp. Med. vol. 191, No. 5, Mar. 6, 2000. pp. 891-897.
McCoy Kathy and Graham Le Gros. "The role of CTLA-4 in the regulation of T cell immune responses." Immunology and Cell Biology. 77: pp. 1-10,1999.
Liu Alvin Y. , Randy R. Robinson, "Chimeric mouse-human IgG1 antibody that can mediate lysis of cancer cells" Proc.Natl. Acad. Sci. USA vol. 84, pp. 3439-3443,May 1987 Medical Sciences.

Ishikawa Dai, Hironori Kikkawa.et al., "GD1α-replica peptides functionally mimic GD1α, an adhesion molecule of metastatic tumor cells, and suppress the tumor metastasis" FEBS Letters 441(1998) p. 20-24.
Becton-Dickson "Detecting Intracellular Cytokines in Activated Lymphocytes" BD Biosciences, 1999, pp. 1-12.
Wu George Y. and Catherine H. Wu.,"Receptor-mediated in Vitro GeneTransformation . . . ", The Journal of Biological Chemistry, 1987, vol. 262, pp. 4429-4432.
Wells, William A. "Eek, a XenoMouse" Chemistry & Biology 2000, 7(8): R185-R186.
Liu et al. "Production of a mouse-human chimeric monoclonal antibody to CD20 with potent Fc-dependent biologic activity" J. Immunology, 1987;139:3521-3526.
Jost, Carolina R., Istvan Kurucz, et al., "Mammalian Expression and Secretion of Functional Single-chain Fv Molecules" J.Biol.Chem., vol. 269, No. 42, Issue of Oct. 21, p. 26267-26273, 1994.
Kohler, G. and C. Milstein "Continuous cultures of fused cells secreting antibody of predefined specificity" Nature vol. 256 Aug. 7, 1975 pp. 495-497.
Leach, Dana R. et al., "Enhancement of Antitumor Immunity by CTLA-4 Blockade" Science vol. 271 Mar. 22, 1996 pp. 1734-1736.
Thompson, Craig B. and James P. Allison. et al., "The emerging role of CTLA-4 as an immune attenuator" Immunity, vol. 7, pp. 445-450, Oct. 1997.
Latchman, Y et al. "PD-L2 is a second ligand for PD-1 and inhibits T cell activation" Nature Immunology Mar. 2001, vol. 2, No. 3. pp. 261-268.
Freeman G. et al. "Engagement of the PD-1 Immunoinhibitory Receptor by a Novel B7 Family Member Leads to Negative Regulation of Lymphocyte Activiation" J. Exp. Med. vol. 192, No. 7,Oct. 2, 2000 1027-1034.
Agata, Yasutoshi, et al. "Expression of the PD-1 antigen on the surface of stimulated mouse T and B lymphocytes" Int. Immunol., 1996, vol. 8,No. 5, pp. 765-772.
Nishimura, Hiroyuki, et al "Developmentally regulated expression of the PD-1 protein on the surface of double-negative (CD4–CD8–) thymocytes" Int. Immunology, 1996, vol. 8, No. 5, pp. 773-780.
Li, W. et.al, "Protection of CD8+ T cells from activation-induced cell death by IL-18" J. Leukoc. Biol., 82, pp. 142-151, 2007.
Okamura et. al, "Cloning of a new cytokine that induces IFN-y production by T cells" Nature, 378: pp. 88-91, 1995.
Fong L. et al., "Potentiating Endogenous Antitumor Immunity to Prostate Cancer through combination immunotherapy with CTLA4 Blockade and GM-CSF" Cancer Res, 2009, 69:609-615.
Fabbi, Marina et al., "Context-dependent role of IL-19 in cancer biology and counter-regulation by IL-18BP" J Leukoc Biol. Apr. 2015;97:665-675.
Simpkins F. et al.,"Chemoimmunotheraphy Using Pegylated Liposomal Doxorubicin and Interleukin-18 in Recurrent Ovarian Cancer: A Phase I Dose-Escalation Study" Cancer ImmunolRes. Sep. 2013;1(3):168-78.
Robertson MJ. et al., "A dose-escalation study of recombinant interleukin-18 in combination with rituximab in patients with non-hodgkin's lymphoma" J mmunother Jul.-Aug. 2013;36(6):331-41.
Tarhini AA. et al., "A Phase 2, Randomized Study of SB-485232, rhIL-18, in Patients With Previously Untreated Metastatic Melanoma" Cancer. Feb. 15, 2009;115(4):859-68.
Valcarcel , M et al., "IL-18 Regulates melanoma VLA-4 Integrin Activation through a hierarchized sequence of inflammatory factors" J. Invest. Dermatol.2014; 134, 470-480.
Lim, H. X. et al., "IL-18 enhances immunosuppressive responses by promoting differentiation into monocytic myeloid-derived suppressor cells" J. Immunol. 2014; 193,5453-5460.
Uzan, B. et al., "Interleukin-18 produced by bone marrow-derived stromal cells supports T-cell acute leukaemia progression" EMBO Mol. Med. 2014; 6,821-834.
Crende, O. et al., "Metastatic Lesions with and without Interleukin-18-dependent genes in advanced-stage melanoma patients" Am. J. Pathol. 2013; 183,69-82.
Palma G. et al., "Interleukin 18: Friend or foe in cancer" Biochim Biophys Acta. Dec. 2013;1836(2):296-303.

(56) References Cited

OTHER PUBLICATIONS

Kim, K. et al., "Interleukin-18 is a critical factor for vascular endothelial growth factor-enhanced migration in human gastric cancer cell lines" Oncogene 2007; 26, 1468-76.
Majima, T. et al., "Exploitation of interleukin-18 by gastric cancers for their growth and evasion of host immunity" Int. J. Cancer 2006; 118,388-395.
Dinarello CA. "The paradox of pro-inflammatory cytokines in cancer" Cancer Metastasis Rev. Sep. 2006;25(3):307-13.
Terme M. et al., "Cancer-induced immunosuppression: IL-18-Elicited Immunoablative NK Cells" Cancer Res. Jun. 1, 2012;72(11):2757-67.
Terme M. et al., "IL-18 Induces PD-1-Dependent Immunosuppression in Cancer" Cancer Res. Aug. 15, 2011;71(16):5393-9.
Ehlers M. et al.,"Immunoregulatory Natural Killer Cells Suppress Autoimmunity by Down-Regulating Antigen-Specific CD8+ T Cells in Mice" Endocrinology Sep. 2012;153(9):4367-79.
Postow Micheal A. "Managing Immune Checkpoint-Blocking Antibody Side Effects" ASCO Educational Book. 2015; 76-83.
Laubli Heinz et al., "Acute heart failure due to autoimmune myocarditis under pembrolizumab treatment for metastatic melanoma" J. ImmunoTherapy. Cancer 2015; 3:11.
Quirk SK. et al., "Immune=mediated adverse events of anticytotoxic T lymphocyte-associated antigen 4 antibody therapy in metastatic melanoma" Transl Res. Nov. 2015;166(5):412-24.
Horvat TZ. et al., "Immune-Related Adverse Events, Need for Systemic Immunosuppression, and Effects on Survival and Time to Treatment Failure in Patients With Melanoma Treated With Ipilimumab at Memorial Sloan Kettering Cancer Center." J Clin Oncol. Oct. 1, 2015;33(28):3193-8.
Bertrand A. et al., "Immune related adverse events associated with anti-CTLA-4 antibodies: systematic review and meta-analysis." BMC Med. Sep. 4, 2015;13:211.
Freeman-Keller M. et al., "Nivolumab in Resected and Unresectable Metastatic Melanoma: Characteristics of Immune-Related Adverse Events and Association with Outcomes" J. Clin CancerRes. Oct. 7, 2015. pp. 1-27.
Gibney G. T. et al., "Safety, correlative markers, and clinical results of adjuvant nivolumab in combination with vaccine in resected high-risk metastatic melanoma." Clin Cancer Res. Feb. 15, 2015;21(4):712-20.
Corsello SM. et al., "Endocrine side effects induced by immune checkpoint inhibitors." J Clin Endocrinol Metab. Apr. 2013;98(4):1361-75.
Gelao L. et al., "Immune Chekpoint Blockade in Cancer Treatment: A Double-Edged Sword Cross-Targeting the Host as an Innocent Bystander" Toxins (Basel). Mar. 3, 2014;6(3):914-33.
Lalor SJ. et al., "Caspase-1-processed cytokines IL-1beta and IL-18 promote IL-17 production by gammadelta and CD4 T cells that mediate autoimmunity." J Immunol. May 15, 2011;186(10):5738-48.
Mills KH. et al., "The role of inflammasome-derived IL-1 in driving IL-17 responses." J Leukoc Biol. Apr. 2013;93(4):489-97.
Sedimbi SK. et al.,"IL-18 in inflammatory and autoimmune disease" Cell Mol Life Sci. Dec. 2013;70(24):4795-808.
Yang CA. et al., "Inflammasomes and human autoimmunity: A comprehensive review" J Autoimmun. Jul. 2015;61:1-8.
Ikeda A. et al., "Progression of autoimmune hepatitis is mediated by IL-18-producing dendritic cells and hepatic CXCL9 expression in mice." Hepatology. Jul. 2014;60(1):224-36.

Yazdi AS. et al., "The two facies of the inflammasome adaptor ASC in epithelial skin carcinogenesis" Clin Exp Rheumatol. Sep.-Oct. 2015;33(4 Suppl 92):94-6.
Santana P. et al., "Is the inflammasome relevant for epithelial cell function?" Microbes Infect. Nov. 8, 2015. pii: S1286-4579(15)00230-0.
Kyi C and Postow MA "Checkpoint blocking antibodies in cancer immunotherapy", FEBS Letters, vol. 588, No. 2, pp. 368-376, doi.org/10.1016/j.febslet.2013.10.015.
NZ Office Action for NZ Patent Application No. 729395, dated Dec. 11, 2017.
El-Gazzar A1, Groh V, Spies T. Immunobiology and conflicting roles of the human NKG2D lymphocyte receptor and its ligands in cancer. J. Immunol. 2013; 191: 1509-1515.
Cheng M, Chen Y, Xiao W, Sun R, Tian Z. NK cell-based immunotherapy for malignant diseases. Cell Mol Immunol. 2013;10:230-52.
Champsaur M, Lanier LL Effect of NKG2D ligand expression on host immune responses.. Immunol Rev. 2010;235:267-85.
Chitadze G, Bhat J, Lettau M, Janssen O, Kabelitz DScand J Generation of soluble NKG2D ligands: proteolytic cleavage, exosome secretion and functional implications. Scandinavian J. Immunol. 2013;78:120-9.
Romee R, Leong JW, Fehniger TA. Utilizing cytokines to function-enable human NK cells for the immunotherapy of cancer. Scientifica (Cairo). 2014;2014:205796 Epub Jun. 25, 2014.
Okamura H, Minato N, Toi M, Tanaka Y. Zoledronic acid-induced expansion of γδ T cells from early-stage breast cancerpatients: effect of IL-18 on helper NK cells. Sugie T, Murata-Hirai K, Iwasaki M, Morita CT, Li W, Cancer Immunol Immunother. 2013;62:677-87.
Kuppala MB, Syed SB, Bandaru S, Varre S, Akka J, Mundulru HP. Immunotherapeutic approach for better management of cancer—role of IL-18. Asian Pac J Cancer Prev. 2012;13(11):5353-61.
Wong, JL et al. IL-18-primed helper NK cells collaborate with dendritic cells to promote recruitment of effector CD8+ T cells to the tumor microenvironment. Cancer Res Aug. 1, 2013;73(15):4653-62.
Yazdi AS. et al., "The Role of the Inflammasome in Nonmyeloid Cells" J Clin Immunol. Sep. 2010;30(5):623-7.
Cella M. et al., "Beyond NK cells: the expanding universe of innate lymphoid cells" Front Immunol. Jun. 16, 2014;5:282.
Lugli E. et al., "NK cell subset redistribution during the course of viral infections" Front Immunol. Aug. 14, 2014;5:390.
Seillet C. et al., "Differentiation and diversity of subsets in group 1 innate lymphoid cells" Int Immunol. Sep. 23, 2015, pp. 1-9.
Xu HM. "Th1 cytokine-based immunotherapy for cancer" Hepatobiliary Pancreat Dis Int. Oct. 2014;13(5):482-94.
Novick D. et al., "Interleukin-18, more than a Th1 cytokine" Semin Immunol. Dec. 15, 2013;25(6):439-48.
Nakanishi K. et al., "Interleukin-18 regulates both Th1 and Th2 responses." Annu Rev Immunol.2001;19:423-74.
Croxford AL. et al., "IL-12-and IL-23 in health and disease" Cytokine Growth Factor Rev. Aug. 2014;25(4):415-421.
International Preliminary Report on Patentability for PCT/JP2015/072505, dated Feb. 9, 2017.
International Search Report for PCT/JP2015/072505, dated Oct. 13, 2015.
KR Office Action for KR Patent Application No. 10-2017-7006235, dated Jun. 14, 2018.
CN Office Action for CN Patent Application No. 201580042424.7, dated Dec. 6, 2019, 20 pages.

\* cited by examiner

SEQUENCE LISTING

```
<160> NUMBER OF SEQ ID NOS: 2

<210> SEQ ID NO 1
<211> LENGTH: 157
<212> TYPE: PRT
<213> ORGANISM: Homo sapiens

<400> SEQUENCE: 1

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Met Tyr Lys Asp Ser Gln Pro Arg Gly Met Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155

<210> SEQ ID NO 2
<211> LENGTH: 157
<212> TYPE: PRT
<213> ORGANISM: Murine

<400> SEQUENCE: 2

Asn Phe Gly Arg Leu His Cys Thr Thr Ala Val Ile Arg Asn Ile Asn
1               5                   10                  15

Asp Gln Val Leu Phe Val Asp Lys Arg Gln Pro Val Phe Glu Asp Met
            20                  25                  30

Thr Asp Ile Asp Gln Ser Ala Ser Glu Pro Gln Thr Arg Leu Ile Ile
        35                  40                  45

Tyr Met Tyr Lys Asp Ser Glu Val Arg Gly Leu Ala Val Thr Leu Ser
    50                  55                  60
```

-continued

```
Val Lys Asp Ser Lys Met Ser Thr Leu Ser Cys Lys Asn Lys Ile Ile
 65              70                  75                  80

Ser Phe Glu Glu Met Asp Pro Pro Glu Asn Ile Asp Asp Ile Gln Ser
             85                  90                  95

Asp Leu Ile Phe Phe Gln Lys Arg Val Pro Gly His Asn Lys Met Glu
            100                 105                 110

Phe Glu Ser Ser Leu Tyr Glu Gly His Phe Leu Ala Cys Gln Lys Glu
        115                 120                 125

Asp Asp Ala Phe Lys Leu Ile Leu Lys Lys Lys Asp Glu Asn Gly Asp
        130                 135                 140

Lys Ser Val Met Phe Thr Leu Thr Asn Leu His Gln Ser
145                 150                 155
```

THERAPEUTIC AGENT FOR CANCER WHICH COMPRISES COMBINATION OF IL-18 AND MOLECULE-TARGETING ANTIBODY

TECHNICAL FIELD

The present invention relates to a cancer therapeutic agent that uses interleukin-18 (hereinafter referred to as "IL-18") and a molecular-targeted antibody in combination. More specifically, the present invention relates to a cancer therapeutic agent containing IL-18 and a molecular-targeted antibody, thereby achieving a synergistic excellent antitumor effect and causing fewer adverse reactions.

BACKGROUND ART

It is known that peritoneal metastasis of tumor cells is easily induced, accompanied with cancers such as a gastric cancer, a large intestine cancer, and an ovarian cancer, and is very difficult to treat because the peritoneal metastasis may develop despite surgical removal of the tumors. Several therapeutic approaches to the peritoneal metastasis have been attempted so far, including a treatment with a chemotherapeutic agent, a treatment that targets a vascular endothelial growth factor (VEGF), and a sensitization therapy using bisphosphonic acid.

Further, antibodies targeting a CTLA-4 antigen or a PD-1/PD-L1 antigen, which are antigens expressed on lymphocytes (regulatory cells) that suppress immune reaction and/or inflammatory response and on macrophages in order to reduce the above lymphocytes (regulatory lymphocytes) have recently begun to be put to clinical practice (Patent Literatures 1 and 2).

While reducing the regulatory lymphocytes, the above antibodies enhance effector lymphocytes expressing, for example, CD28 and NKG2D, so that the effector lymphocytes eliminate tumor cells and pathogen-infected cells.

Thus the treatment with the above antibodies aims at regression or disappearance of tumors by activating innate immunity and acquired immunity, continuously increasing tumor cell-breaking lymphocytes (also referred to effector lymphocytes or effector cells), and, in turn, enhancing migration to tumors. The above antibodies have been proven to be effective against malignant tumors, such as melanoma, which have been difficult to be treated by known treatment techniques. Thus, the above antibodies have been expected to enhance their effectiveness and expand their application to many tumor cells.

In addition, an attempt has also been made to confirm an antitumor effect by using GM-CSF, IL-15, and an anti-CTLA-4 antibody (Non-patent Literature 1). Further, it is disclosed that a combination of IL-18 and rituximab or HERCEPTIN (registered trademark) exhibits a more excellent therapeutic effect in comparison with the use of a single agent (Patent Literature 3). Furthermore, there is disclosed a cancer immunotherapy using a composition containing a combination of a compound represented by a predetermined formula, one or more molecular-targeted antibody, and an immunostimulating compound (Patent Literature 4).

CITATION LIST

Patent Literature

[Patent Literature 1]
International publication No. WO 2004/004771 (Publication date: Jan. 15, 2004)

[Patent Literature 2]
Japanese Translation of PCT International Application, Tokuhyo, No. 2004-512005 (Publication date: Apr. 22, 2004)

[Patent Literature 3]
Japanese Translation of PCT International Application, Tokuhyo, No. 2010-52239 (Publication date: Jul. 1, 2010)

[Patent Literature 4]
Japanese Translation of PCT International Application, Tokuhyo, No. 2008-539249 (Publication date: Nov. 13, 2008)

Non-Patent Literature

[Non-Patent Literature 1]
Fong L. et al., Cancer Res, 2009, 69:609-615.

SUMMARY OF INVENTION

Technical Problem

Strictly, therapeutic effects produced by using the antibodies disclosed in Patent Literatures 1 and 2 are considered to still have room for improvement. Moreover, the antibodies disclosed in Patent Literatures 1 and 2 have the problem that the reduced regulatory lymphocytes and the enhanced effector lymphocytes may cause side effects such as onset of an autoimmune disease. In other words, the techniques disclosed in Patent Literatures 1 and 2 have room for improvement in terms of enhancement of a therapeutic effect and reduction of adverse reactions.

Further, the method disclosed in Non-Patent Literature 1 is not a realistic method because it requires a very high dose of agent.

Patent Literature 3 discloses that, as a result of concurrently or sequentially administering IL-18 and rituximab or HERCEPTIN (registered trademark) to individual patients, the combined use produced more excellent therapeutic effect than the use of a single agent. Further, Patent Literature 4 discloses that adding an immunopotentiator to a specific compound represented by a predetermined formula and one or more molecular-targeted antibodies (rituximab, HERCEPTIN (registered trademark), etc.) can enhance immune response. Note that the "molecular-targeted antibody" refers to an antibody capable of recognizing surface antigens involved in the function of lymphocytes and surface antigens of cancer cells.

However, what effect is produced by using an antibody other than the antibodies used in Patent Literatures 3 and 4 and to what extent adverse reactions are caused have not been revealed. Therefore, it can be said that Patent Literatures 3 and 4 have not yet provided a sufficient knowledge about provision of a cancer therapeutic agent that achieves enhancement of a therapeutic effect and reduction of adverse reactions.

The present invention has been accomplished in view of the above problems with the known techniques. It is an object of the present invention to provide a novel cancer therapeutic agent containing IL-18 and at least one predetermined antibody, thereby achieving an excellent antitumor effect and reduction of side effects.

Solution to Problem

The inventors of the present invention have conducted diligent studies on a cancer therapeutic agent that achieves enhancement of a therapeutic effect and reduction of adverse reactions. As a result, the inventors of the present invention have discovered that the above problems can be solved by using IL-18 in combination with one or more antibodies selected from the group consisting of an anti-PD-L1 antibody, an anti-PD-1 antibody, an anti-PD-L2 antibody, an anti-CTLA-4 antibody, an anti-CD25 antibody, an anti-CD33 antibody, and an anti-CD52 antibody. The inventors have thereby completed the present invention.

That is, in order to solve the above problems, a cancer therapeutic agent according to an embodiment of the present invention contains, as active ingredients, IL-18 and one or more antibodies selected from the group consisting of an anti-PD-L1 antibody, an anti-PD-1 antibody, an anti-PD-L2 antibody, an anti-CTLA-4 antibody, an anti-CD25 antibody, an anti-CD33 antibody, and an anti-CD52 antibody.

Advantageous Effects of Invention

A cancer therapeutic agent according to an embodiment of the present invention contains, as active ingredients, IL-18 and one or more antibodies selected from the group consisting of an anti-PD-L1 antibody, an anti-PD-1 antibody, an anti-PD-L2 antibody, an anti-CTLA-4 antibody, an anti-CD25 antibody, an anti-CD33 antibody, and an anti-CD52 antibody. This makes it possible to remarkably enhance an antitumor effect of the one or more antibodies. This, as a result, produces the effect of providing a cancer therapeutic agent that achieves a high therapeutic effect and causes fewer adverse reactions.

DESCRIPTION OF EMBODIMENTS

Figure 1:
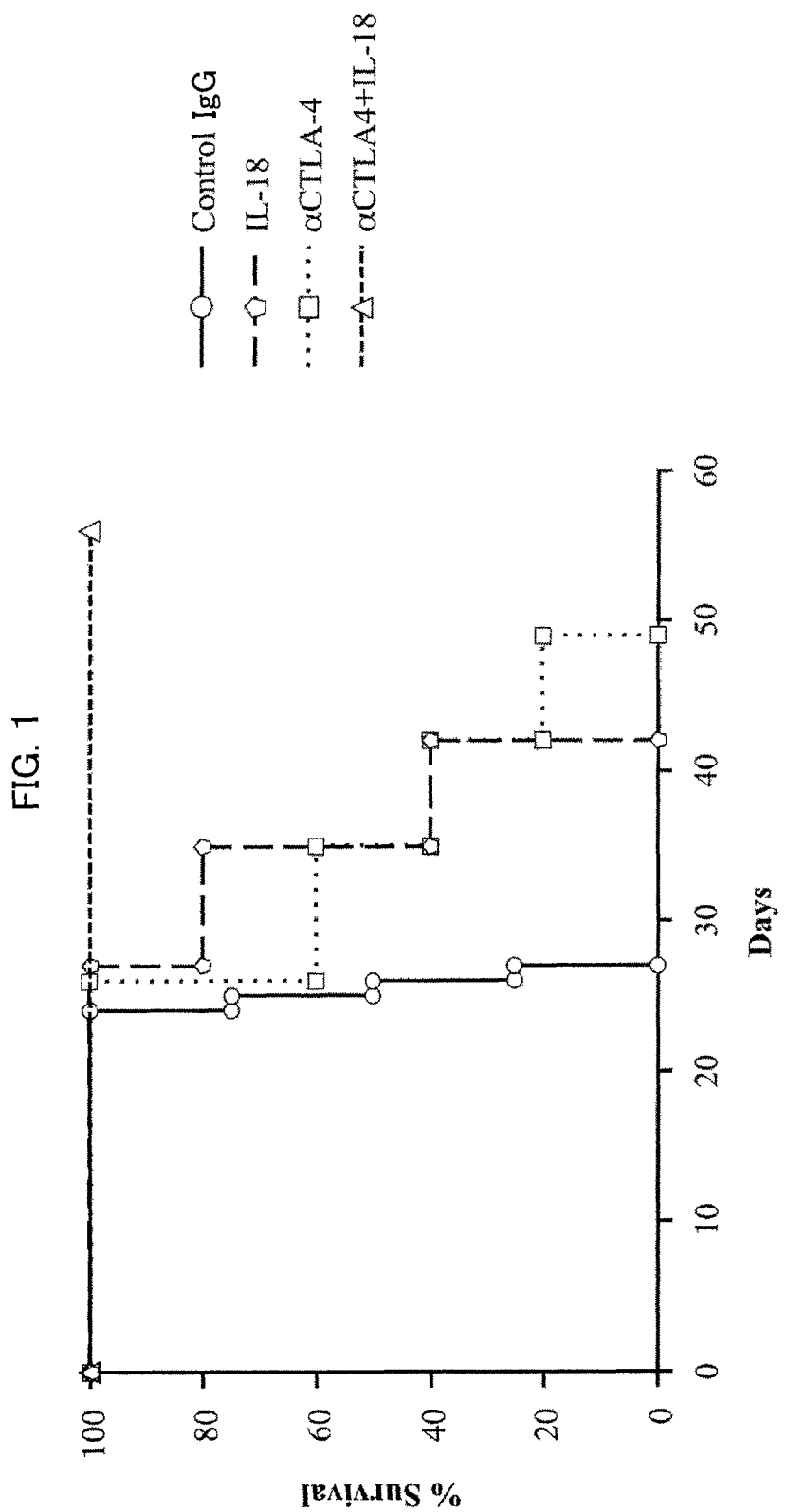
FIG. 1 is a graph showing results of monitoring, as a survival rate of mice, an effect resulting from administration of a cancer therapeutic agent containing an anti-CTLA-4 antibody and IL-18 3 days and later days after the day of inoculation of CT-26 cells.

The following description will discuss embodiments of the present invention in detail. For example, the expression like "A to B" is used to indicate a range and such an expression means "A or more and B or less". Note that all Patent Literatures and Non-Patent Literatures cited herein are hereby incorporated by reference in their entirety.

Embodiment 1: Cancer Therapeutic Agent According to Embodiment of Present Invention (1) Active Ingredients A cancer therapeutic agent according to an embodiment of the present invention contains, as active ingredients, IL-18 and one or more antibodies selected from the group consisting of an anti-PD-L1 antibody, an anti-PD-1 antibody, an anti-PD-L2 antibody, an anti-CTLA-4 antibody, an anti-CD25 antibody, an anti-CD33 antibody, and an anti-CD52 antibody.

IL-18 was discovered in 1995 by Okamura et al., as an IFN-γ-inducing factor (Okamura et. al, Nature, 378:88-91, 1995). This IL-18 is a cytokine which has been recently elucidated to have various biological actions.

IL-18 is formed from change of pro-IL-18 into active IL-18, as a consequence of endoplasmic reticulum stress response to stress such as nutritional deficiency, lack of oxygen, and/or ultraviolet light. The endoplasmic reticulum stress response results in activation of inflammasome (which is a protein complex, and contains, for example, NLRP3, ASC, and caspase-1). The inflammasome thus activated activates caspase-1, so that pro-IL-18 is processed by the caspase-1 and changed into active IL-18.

IL-18 is known to be capable of acting on effector cells (including CD8-positive T cells, natural killer cells (hereinafter, referred to as NK cells), and γδ T cells) which are activated by antigens and/or cytokines, and remarkably increasing the number of these effector cells. IL-18 is known to also inhibit death of these effector cells and promote survival and differentiation of the effector cells (e.g., Li Wen et al., J. Leukoc. Biol., 82, 142-151, 2007).

IL-18 is not particularly limited, and can be, for example, a human IL-18 polypeptide (SEQ ID NO: 1) or a mouse IL-18 polypeptide (SEQ ID NO: 2) which are disclosed in Patent Literature 3. The homology between the amino acid sequence of human IL-18 and the amino acid sequence of mouse IL-18 is 65%. Human IL-18 polypeptides are disclosed in, for example, EP 0692536 A2, EP 0712931 A2, EP 0767178 A1, and WO 97/2441, as described in Patent Literature 3. Note that, hereinafter, an IL-18 polypeptide will be simply referred to as "IL-18".

As described in Patent Literature 3, the human IL-18 is a recombinant mature form of human IL-18 that is expressed in a non-pathogenic strain of *Escherichia coli*. Mouse IL-18 cDNA encodes a precursor protein consisting of 192 amino acids (SEQ ID NO: 2), and human IL-18 cDNA encodes a precursor protein consisting of 193 amino acids (SEQ ID NO: 1).

IL-18 can be collected and purified from recombinant cell cultures by any of publicly known methods which include ammonium sulfate or ethanol precipitation, acid extraction, anion or cation exchange chromatography, phosphocellulose chromatography, hydrophobic interaction chromatography, affinity chromatography, hydroxylapatite chromatography, lectin chromatography, and high-performance liquid chromatography.

In a case where IL-18 is denatured during intracellular synthesis, isolation and/or purification, an active conformation can be regenerated by a well-known technique for refolding proteins. A method for purifying and preparing an active human IL-18 is disclosed in WO 01/098455. IL-18 can also be a commercially-available polypeptide.

The cancer therapeutic agent according to an embodiment of the present invention contains, as an antibody (or antibodies), one or more antibodies selected from the group consisting of an anti-PD-L1 antibody, an anti-PD-1 antibody, an anti-PD-L2 antibody, an anti-CTLA-4 antibody, an anti-CD25 antibody, an anti-CD33 antibody, and an anti-CD52 antibody.

The anti-PD-L1 antibody, the anti-PD-1 antibody, and the anti-PD-L2 antibody are described in detail in Patent Literature 1. As described in Patent Literature 1, human PD-1 cDNA is composed of the base sequence shown in EMBL/GenBank Acc. No. NM_005018, and mouse PD-1 cDNA is composed of the base sequence shown in Acc. No. X67914. Expression of human PD-1 cDNA and mouse PD-1 cDNA are observed when thymus cells differentiate from $CD4^-CD8^-$ cell into $CD4^+CD8^+$ cell (Int. Immunol., 1996, vol. 18, issue 5, pp. 773-780, and J. Exp. Med., 2000, vol. 191, issue 5, pp. 891-898).

It has been reported that PD-1 expression in periphery is observed in myeloid cells such as T cells or B cells activated by stimulation from antigen receptors (Int. Immunol., 1996, vol. 18, issue 5, pp. 765-772), or activated macrophages. Further, PD-1 is known to give signals that inhibit signals of antigen receptors (TCR).

PD-L1 is a ligand of PD-1. PD-L1 is expressed not only in tumor cells but also in so-called antigen-presenting cells such as activated monocytes and dendritic cells (J. Exp. Med., 2000, vol. 191, issue 7, pp. 1027-1034). As disclosed in Patent Literature 1, human PD-L1 cDNA is composed of the base sequence shown in EMBL/GenBank Acc. No. AF233516 and mouse PD-L1 cDNA is composed of the base sequence shown in NM_021893.

The above cells present, to T lymphocytes, interaction molecules that induce a variety of immuno-inductive signals. PD-L1 is one of molecules that induce the above-described inhibitory signals given by PD-1.

As disclosed in Patent Literature 1, it has been reported that PD-L2 has been identified as a second ligand of PD-1, and expression and function of PD-L2 are almost the same as those of PD-L1. Note here that human PD-L2 cDNA is composed of the base sequence shown in EMBL/GenBank Acc. No. NM_025239 and mouse PD-L2 cDNA is composed of the base sequence shown in NM_021896 (Nature Immunology, 2001, vol. 2, issue 3, pp. 261-267).

It has been thought that the inhibitory signals from conjugated inhibitory molecules represented by PD-1 control immunological tolerance or abnormal immune reaction to autoantigens during the process of lymphocyte generation or maturation. Such control is carried out by a mechanism that appropriately controls positive signals from antigen receptors (TCR) and conjugated stimulation molecules.

For example, Japanese Patent Application Publication, Tokukai, No. 2007-277242 discloses an anti-CTLA-4 antibody. CTLA-4 is cytotoxic T lymphocyte-associated antigen 4 (CD152). As described in Japanese Patent Application Publication, Tokukai, No. 2007-277242, in a case where CTLA-4 binds to its natural ligands, B7.1 (CD80) and B7.2 (CD86), a negative regulatory signal is delivered to T cells. Blocking this negative regulatory signal results in enhancement of a T cell immune function and T cell antitumor activity in animal models (Thompson and Allison, Immunity, 7, pp. 445-450 (1997); and McCoy and LeGros, Immunol. & Cell Biol. 77:1-10 (1999)).

It has been demonstrated that in a case where negative regulatory signals of CTLA-4 are blocked with use of antibodies, T cell-mediated killing of tumors is enhanced and antitumor immunity can be induced (see, e.g., Leach et al., Science 271:1734-1736 (1996)). The complete sequence of human CTLA-4 is shown in GenBank Acc. No. L15006.

CD25 is a single-chain glycoprotein having a molecular weight of 55 kDa, and is known as a surface antigen of adult T cell leukemia cells. CD33 is known as a surface antigen of acute myelocytic leukemia cells. Meanwhile, CD52 is known as a surface antigen of B cell chronic lymphocytic leukemia cells.

As long as the anti-PD-L1 antibody, the anti-PD-1 antibody, the anti-PD-L2 antibody, the anti-CTLA-4 antibody, the anti-CD25 antibody, the anti-CD33 antibody, and the anti-CD52 antibody inhibit immunosuppressive signals of PD-L1, PD-1, PD-L2, CTLA-4, CD25, CD33, and CD52, respectively, these antibodies each can be any of antibodies derived from human, mouse, rat, rabbit, or goat. Moreover, these antibodies each can be any of polyclonal or monoclonal antibodies, complete or shortened (for example, F(ab')2, Fab', Fab, or Fv fragment, each of which is hereinafter also referred to as "antibody fragment") antibodies, chimeric antibodies, humanized antibodies, and completely humanized antibodies of the antibodies derived from human, mouse, rat, rabbit, or goat.

The above antibodies each can be produced by using, as an antigen, a partial protein of an extracellular domain of PD-L1, PD-1, PD-L2, CTLA-4, CD25, CD33 or CD52, according to a publicly known production method for antigens or antiserum. The partial protein of the extracellular domain can be prepared by a publicly known method for expressing or purifying proteins.

The polyclonal antibodies can be produced by a publicly known method. For example, the polyclonal antibodies can be produced by: first immunizing a suitable animal with an antigenic protein or a mixture of an antigenic protein and a carrier protein; harvesting, from the animal thus immunized, a matter containing an antibody to the antigenic protein; and separating and purifying the antigen.

Examples of the animal used for production of the polyclonal antibodies generally include mouse, rat, sheep, goat, rabbit, and guinea pig. In order to improve productivity of the antibodies, Freund's complete adjuvant or Freund's incomplete adjuvant can be administered with the antigen. Such administration is carried out generally once every two weeks and approximately 3 to 10 times in total.

The polyclonal antibodies can be collected from blood, ascites, or the like of an animal immunized by the above method. A polyclonal antibody titre in antiserum can be measured by ELISA.

The polyclonal antibodies can be separated and purified by an immunoglobulin separation and purification method including, for example, a purification method which uses an active adsorbent (e.g., an antigen binding solid phase, protein A, or protein G), salting-out, alcohol precipitation, isoelectric precipitation, electrophoresis, adsorption and desorption with an ion exchanger, ultracentrifugation, and gel filtration.

The above antibodies are more preferably monoclonal antibodies or modified monoclonal bodies. As disclosed in Patent Literature 1, it is possible to produce monoclonal-antibody-producing cells by: selecting an individual whose antibody titre has been confirmed, from among animals immunized with an antigen; harvesting the spleen or a lymph node of the individual on 2nd to 5th day after final immunization; fusing antibody-producing cells contained in the spleen or the lymph node, with homogeneous or heterozoic myeloma cells; and thereby preparing monoclonal-antibody-producing hybridomas which can be subcultured.

The antigenic protein is administered, by itself or together with a carrier and/or a diluent, to a site where antibodies can be produced. When the antigenic protein is administered, Freund's complete adjuvant or Freund's incomplete adjuvant is generally administered together in order to improve productivity of the antibodies.

Alternatively, the animal can be immunized by a method called "DNA immunization". This method utilizes a phenomenon in which, after immune animal's tibialis anterior muscle of a hind leg is treated with cardiotoxin and further, antigenic-protein-expressing vectors are introduced into the muscle, the antigenic-protein-expressing vectors are taken into myocytes in the process of tissue repair and consequently, antigenic proteins are expressed (Nature Immunology, 2001, vol. 2, issue 3, pp. 261-267).

The animal to be immunized can be mouse, rat, sheep, goat, rabbit, or guinea pig, and is preferably mouse or rat. A fusing operation can be executed by the method (Nature, 1975, vol. 256, issue 5517, pp. 495-497) of Kohler and Milstein. Further, as a fusion accelerant, polyethylene glycol (PEG), Sendai virus, and/or the like, is used. Examples of the myeloma cells include myeloma cells such as P3U1, NS1, SP2/0, and AP1. Among these myeloma cells, P3U1 is often used typically.

As disclosed in Patent Literature 1, the monoclonal-antibody-producing cells can be screened by, for example, detecting the monoclonal-antibody-producing cells by ELISA or the like. In ELISA, hybridoma culture supernatant is added to a solid phase to which antigenic proteins are adsorbed directly or together with carriers. Further, the antibody titre of the hybridoma culture supernatant can be measured by ELISA. In addition, the monoclonal antibodies can be separated and purified by an immunoglobulin separation and purification method similar to that described above in regard to the polyclonal antibodies.

The hybridomas can be publicly known hybridomas which are typically used for production of the antibodies. For example, in a case where the anti-PD-L1 antibody or the anti-PD-1 antibody is to be produced, hybridomas disclosed in Patent Literature 1 can be used.

The antibody fragments can be obtained by processing the antibodies with protease and optionally carrying out reduction after the processing. A F(ab')2 antibody fragment can be further purified by completely digesting purified monoclonal antibodies with pepsin and then carrying out purification by any of publicly known methods including ion-exchange chromatography, gel filtration, or affinity chromatography. A Fab' antibody fragment can be prepared by partially reducing the F(ab')2 with use of 2-mercaptoethylamine. Further, a Fab antibody fragment can be prepared by purification after direct digestion of the F(ab')2 with digestive enzyme papain under the presence of cysteine.

An scFv antibody can be prepared by, for example, a method of Jost et al. (J. Biol. Chem., 1994, vol. 269, issue 42, pp. 26267-26273).

The humanized antibodies each can be prepared by substituting, with a part of human antibody, a part of non-human antibody which was prepared by immunizing a mammal that is not a human. Concretely, it has been known that a humanized antibody can be prepared by constructing a chimera with a gene encoding a constant region of a human antibody and a gene encoding a variable region of a non-human antibody (Proc. Natl. Acad. Sci. (USA), 1987, vol. 84, pp. 3439-3443; and J. Immunol., 1987, vol. 139, issue 1, p. 3521).

The DNA sequence of the constant region of the human antibody has been disclosed in a publicly known literature, and a gene of the constant region can be easily obtained from a known clone. Then, a DNA sequence encoding a variable region of an antibody is fused to the constant region of the human antibody. An isotype of the constant region of the human antibody can be selected in view of a desired effective function or desired antibody-dependent cytotoxic activity. The isotype is preferably IgG1, IgG3, or IgG4. Further, both κ chain and λ chain of a human light-chain constant region can be used. Such a humanized chimeric antibody can be expressed by an ordinary method.

The completely humanized antibodies each can be prepared, for example, by using mice (XenoMouse (Chemical Biology, 2000, vol. 7, issue 8, p. R185-6) into which a constant region gene of human immunoglobulin has been introduced. Further, a target antibody can be mass-produced by using, as hybridomas, antibody-producing lymphocytes which have been isolated from the mice. The completely humanized antibody can also be prepared by a phage display method (FEBS Letter, 1998, vol. 441, pp. 20-24).

The cancer therapeutic agent according to an embodiment of the present invention contains, as active ingredients, (i) IL-18 and (ii) one or more antibodies selected from the group consisting of an anti-PD-L1 antibody, an anti-PD-1 antibody, an anti-PD-L2 antibody, an anti-CTLA-4 antibody, an anti-CD25 antibody, an anti-CD33 antibody, and an anti-CD52 antibody. The number of the "one or more antibodies" can be any number as long as the antibodies are selected from the above group.

Particularly, the cancer therapeutic agent according to an embodiment of the present invention preferably contains the anti-PD-L1 antibody and/or the anti-CTLA-4 antibody since the anti-PD-L1 antibody and the anti-CTLA-4 antibody have been proven as a cancer therapeutic agent. The cancer therapeutic agent most preferably contains IL-18, the anti-PD-L1 antibody and the anti-CTLA-4 antibody.

Meanwhile, PD-L1 is a ligand of PD-1 as described above, and PD-L2 is a ligand of PD-1. Accordingly, use of the anti-PD-1 antibody or the anti-PD-L2 antibody in place of the anti-PD-L1 antibody is expected to provide an effect similar to that provided by use of the anti-PD-L1 antibody.

Further, as described above, CD33, CD52, and CD25 are known as a surface antigen of acute myelocytic leukemia cells, a surface antigen of B cell chronic lymphocytic leukemia cells, and a surface antigen of adult T cell leukemia cells, respectively. In neoplastic leukocytes of patients of such types of cancer, many surface antigens each called MICA or MICB are observed.

In a case where the cancer therapeutic agent according to an embodiment of the present invention contains IL-18 and one or more antibodies selected from the group consisting of the anti-CD25 antibody, the anti-CD33 antibody, and the anti-CD52 antibody, the anti-CD25 antibody, the anti-CD33 antibody, and the anti-CD52 antibody target CD25, CD33, and CD52, respectively. Further, as shown in Examples described later, IL-18 can enhance induction of NK cells whose NKG2D expression level is high. Then, the NK cells can recognize MICA and MICB through NKG2D, and can cause lysis of cells which have expressed these surface antigens.

Therefore, it is considered that in a case where the cancer therapeutic agent according to an embodiment of the present invention contains IL-18 and one or more antibodies selected from the group consisting of the anti-CD25 antibody, the anti-CD33 antibody, and the anti-CD52 antibody, the therapeutic agent is likely to have an effective action for treatment of acute myelocytic leukemia, B cell chronic lymphocytic leukemia, and adult T cell leukemia.

In regard to a ratio of amounts of IL-18 and the one or more antibodies which are used in the cancer therapeutic agent according to an embodiment of the present invention, in a case where one antibody is used, a mass ratio of IL-18 and the antibody is preferably 1:10 to 1:200, 1:25 to 1:200, 1:25 to 1:50, or 1:30 to 1:50. Moreover, it is preferable to administer the antibody at the above mass ratio in a case where a dose of IL-18 to be administered to a living body (subject, patient) is 0.1 mg/kg in dose per kg of body weight of the living body.

Meanwhile, in a case where two or more antibodies are used, a ratio of the mass of IL-18 and the sum of masses of the two or more antibodies should be set to the above mass ratio and a mass ratio of the two or more antibodies can be set to any ratio.

In other words, a ratio of the mass of IL-18 and the mass(es) of the one or more antibodies (the sum of the masses of the one or more antibodies to be used) selected from the group consisting of the anti-PD-L1 antibody, the anti-PD-1 antibody, the anti-PD-L2 antibody, the anti-CTLA-4 antibody, the anti-CD25 antibody, the anti-CD33 antibody, and the anti-CD52 antibody is preferably 1:10 to 1:200, 1:25 to 1:200, 1:25 to 1:50, or 1:30 to 1:50, and a mass ratio of the antibodies can be set to any ratio.

For example, in a case where two antibodies are used, IL-18, a first antibody, and a second antibody can be used at a mass ratio of 1:50:50 when the dose of IL-18 is set to 0.1 mg/kg.

The cancer therapeutic agent according to an embodiment of the present invention employs, as active ingredients, IL-18 and the above one or more antibodies (one or more antibodies selected from the group consisting of the anti-PD-L1 antibody, the anti-PD-1 antibody, the anti-PD-L2 antibody, the anti-CTLA-4 antibody, the anti-CD25 antibody, the anti-CD33 antibody, and the anti-CD52 antibody). The cancer therapeutic agent can be a composition in which IL-18 and the one or more antibodies are mixed with each other. Alternatively, IL-18 and the one or more antibodies each can separately exist while being unmixed with each other.

In other words, as long as a cancer therapeutic agent uses, as active ingredients, IL-18 and the one or more antibodies, the cancer therapeutic agent is encompassed in the scope of the cancer therapeutic agent according to an embodiment of the present invention regardless of whether or not IL-18 and the one or more antibodies are mixed with each other.

For example, even in a case where IL-18 and the one or more antibodies are separately administered to a patient as in a case where IL-18 is administered to a patient first and then the one or more antibodies are administered to the patient, IL-18 and the one or more antibodies are used in combination as active ingredients. Accordingly, an embodiment in which IL-18 and the one or more antibodies are not mixed with each other corresponds to the cancer therapeutic agent according to an embodiment of the present invention which contains IL-18 and the one or more antibodies as active ingredients. Note however that the order of administration is not limited to above order. In other words, IL-18 can be administered to a patient after administration of the one or more antibodies, or alternatively, the one or more antibodies and IL-18 can be simultaneously administered to a patient.

In a case where the one or more antibodies are a plurality of antibodies, administration of the plurality of antibodies can be, but is not limited to, simultaneous administration of the plurality of antibodies. For example, in a case where two antibodies are used, IL-18, a first antibody, and a second antibody can be separately administered in any order to a patient over time. For example, in a case where IL-18, the anti-PD-L1 antibody, and the anti-CTLA-4 antibody are administered to a patient, the order of administration can be the following order: IL-18, the anti-PD-L1 antibody, and then the anti-CTLA-4 antibody; IL-18, the anti-CTLA-4 antibody, and then the anti-PD-L1 antibody; or the like. In a case where IL-18 and a single antibody or a plurality of antibodies are administered to a patient over time, an interval between administration of IL-18 and administration of the antibody or antibodies, or an interval between administration of an antibody and next administration of another antibody is preferably 2 to 5 days.

Further, a site to which IL-18 is administered can be identical to or different from a site to which each antibody is administered. For example, IL-18 and a plurality of antibodies can be administered all together by intravenous injection. Alternatively, for example, IL-18 and a plurality of antibodies can be administered such that IL-18 is administered by intravenous injection, a first antibody is administered by hypodermic injection, and a second antibody is administered by intradermal injection. In consideration of simple administration, typically, it is preferable to administer IL-18 and an antibody or antibodies to one site.

Respective doses of the active ingredients (IL-18 and the one or more antibodies) of the cancer therapeutic agent according to an embodiment of the present invention cannot be uniformly defined since the doses vary depending on age, symptom, etc. of each patient. However, in regard to the doses of the active ingredients per kg of body weight of a patient at one administration, typically, it is preferable that the dose of IL-18 be 0.1 mg/kg and the dose of the one or more antibodies be 1 mg/kg to 20 mg/kg, and it is more preferable that the dose of the one or more antibodies be 2.5 mg/kg to 5.0 mg/kg or 3.0 mg/kg to 5.0 mg/kg. Note that a mass ratio of IL-18 and the one or more antibodies in the active ingredients is as described above.

Though mice are used as test subjects in Examples described later, there is no significant difference between a dose per kg of body weight of a mouse and a dose per kg of body weight of a human. In the case of administration to a human, one possible example case of administration is a case where administration is carried out once every 3 weeks and 4 times in total such that the one or more antibodies are administered in a dose of 1 mg/kg to 20 mg/kg while IL-18 is administered in a dose of 0.1 mg/kg.

(2) Other Ingredients

The cancer therapeutic agent according to an embodiment of the present invention can further contain, for example, a pharmaceutically acceptable carrier, a pharmaceutically acceptable diluent, and/or a pharmaceutically acceptable excipient as disclosed in Patent Literature 3 in addition to the active ingredients, if needed.

The pharmaceutically acceptable carrier can be sterile liquids, such as water and oils. The oils include oils of petroleum origin, animal origin, vegetable origin and synthetic origin, such as peanut oil, soybean oil, mineral oil, sesame oil, etc.

In a case where the cancer therapeutic agent according to an embodiment of the present invention is intravenously administered, water can be used as the carrier. Examples of a liquid carrier for injection solution also include physiological saline solution, dextrose solution and glycerol solution.

Suitable examples of the pharmaceutically acceptable excipient include starch, glucose, lactose, sucrose, gelatin, malt, rice, flour, chalk, silica gel, magnesium stearate, glycerol monostearate, talc, sodium chloride, dried skim milk, glycerol, propylene glycol, water, and ethanol.

The cancer therapeutic agent according to an embodiment of the present invention can also contain, if needed, a small amount of moisturizing agent or emulsifying agent, or a pH buffering agent. The cancer therapeutic agent according to an embodiment of the present invention can take the form of solution, suspension, emulsion, tablets, pills, capsules, powder, a sustained-release formulation, or the like.

The cancer therapeutic agent according to an embodiment of the present invention can be formulated as a suppository including a conventional binder and a conventional carrier, which are, for example, triglycerides. An oral formulation of the cancer therapeutic agent can contain a standard carrier, such as mannitol, lactose, starch, magnesium stearate, sodium saccharine, cellulose, magnesium carbonate, or the like of a pharmaceutical grade. The cancer therapeutic agent according to an embodiment of the present invention can contain a suitable amount of a carrier, together with the active ingredients. The form of the formulation should be appropriately adjusted in accordance with an administration method.

How the cancer therapeutic agent according to an embodiment of the present invention is administered to patients is not specifically limited. However, in one embodiment of the present invention, the cancer therapeutic agent is prescribed, in accordance with a conventional procedure known to the public, as a pharmaceutical composition adapted to intravenous administration to humans.

As disclosed in Patent Literature 3, compositions for intravenous administration are typically solutions in sterile isotonic aqueous buffer. When appropriate, the composition can also contain a solubilizing agent, and a local anesthetic such as lignocaine which eases pain at an injection site.

In general, each of the ingredients is supplied in a unit dose form separately or all of the ingredients are supplied in a unit dose form in a mixed state. In either case, the ingredients are supplied, for example, in the form of a lyophilized powder or water-free concentrate in a hermetically sealed container such as an ampoule or sachet that indicates an amount of an active agent(s). Note that as described above, the cancer therapeutic agent need not necessarily be arranged such that IL-18 and the one or more antibodies are mixed with each other. Therefore, IL-18 and the one or more antibodies can be supplied separately.

In a case where the cancer therapeutic agent is administered by infusion, the cancer therapeutic agent can be dispensed via an infusion bottle which contains sterile pharmaceutical grade water or sterile physiological saline solution. In a case where the cancer therapeutic agent is administered by injection, an ampoule of sterile water for injection or sterile physiological saline solution can be supplied, so that the ingredients can be mixed prior to administration.

The cancer therapeutic agent according to an embodiment of the present invention can be formulated as solution or lyophilized powder for parenteral administration. Such powder can be reconstituted by addition of a suitable diluent or other pharmaceutically acceptable carrier prior to use. A liquid formulation can be a buffered isotonic aqueous solution. Examples of the suitable diluent include normal isotonic physiological saline solution, and standard 5% dextrose in water or sodium acetate buffer solution or ammonium acetate buffer solution.

The above formulation is suitable for parenteral administration, but can also be used for oral administration. Further, the formulation can also be contained in a metered-dose inhaler or nebulizer for inhalation. In some cases, it is desirable to add, to the cancer therapeutic agent, an excipient such as polyvinylpyrrolidone, gelatin, hydroxy cellulose, acacia gum, polyethylene glycol, mannitol, sodium chloride, or sodium citrate.

The cancer therapeutic agent can be encapsulated, tableted or prepared in emulsion or syrup for oral administration. A pharmaceutically acceptable solid or liquid carrier can be added so as to enhance or stabilize the cancer therapeutic agent or to facilitate preparation of the cancer therapeutic agent.

The solid carrier includes starch, lactose, calcium sulfate dihydrate, terra alba, magnesium stearate or stearic acid, talc, pectin, acacia gum, agar, or gelatin.

Examples of the liquid carrier include syrup, peanut oil, olive oil, physiological saline solution, and water. The carrier can also contain a sustained-release material such as glyceryl monostearate or glyceryl distearate alone or with a wax.

The amount of the solid carrier varies, but the amount is approximately 20 mg to approximately 1 g per unit dose. In a case where a pharmaceutical formulation is in a tablet form, the pharmaceutical formulation is prepared in accordance with a conventional pharmaceutical method including milling, mixing, granulating, and compressing, if the method is suitable. Meanwhile, in a case where the pharmaceutical formulation is in a hard gelatin capsule form, the pharmaceutical formulation is prepared in accordance with a conventional pharmaceutical method including milling, mixing and filling.

In a case where the liquid carrier is used, the formulation is in the form of syrup, elixir, emulsion, or an aqueous or non-aqueous suspension. Such a liquid formulation can be administered directly through the mouth (p.o.) or in a state in which the liquid formulation is filled in a soft gelatin capsule.

The cancer therapeutic agent according to an embodiment of the present invention can be used in the form of an aqueous suspension or solution which is prepared for injection and which contains the cancer therapeutic agent having been buffered at physiological pH. It is possible to use, as an aqueous carrier, a variety of aqueous carriers such as 0.4% physiological saline solution or 0.3% glycine. These solutions are sterile and generally free of particulate substances.

The aqueous suspension or solution can be further sterilized by a conventional sterilization method (e.g., filtration) known to the public. The cancer therapeutic agent according to an embodiment of the present invention can contain a pharmaceutically acceptable auxiliary substance(s), such as a pH adjusting agent and/or a buffering agent, which is required to approximate physiological conditions.

The concentration of the cancer therapeutic agent according to an embodiment of the present invention in such a pharmaceutical formulation that contains a carrier, an auxiliary substance(s), etc. should be selected in accordance with a fluid content, a viscosity, etc., according to a concrete administration method selected.

Embodiment 2: Administration of Cancer Therapeutic Agent According to Embodiment of Present Invention A cancer therapeutic agent according to an embodiment of the present invention can be administered to a patient through any appropriate route in the body of the patient.

An administration method can be, for example, any of various conventional methods known to the public which are disclosed in Patent Literature 3. In other words, the cancer therapeutic agent according to an embodiment of the present invention can be administered through any of various delivery systems. Examples of such delivery systems include encapsulation in liposomes, microparticles, microcapsules, recombinant cells capable of expressing compounds, receptor-mediated endocytosis (see, e.g., Wu, et al., J. Biol. Chem. vol. 262, pp. 4429-4432 (1987)), and construction of a nucleic acid as part of a retroviral vector or other vector.

An introduction method includes any of an intradermal route, an intramuscular route, an intraperitoneal route, an intravenous route, a subcutaneous route, an intranasal route, an epidural route, and an oral route, but the introduction method is not limited to the method including the above route.

The cancer therapeutic agent can be administered via any suitable route, for example, by infusion or bolus injection, or by absorption through an epithelial or mucocutaneous lining (e.g., oral mucosa, rectal mucosa, intestinal mucosa, or the like). Meanwhile, the cancer therapeutic agent can be administered together with other biologically active agent(s).

The cancer therapeutic agent according to an embodiment of the present invention can be administrated systematically or locally. In addition, in some cases, it is desirable to introduce the cancer therapeutic agent according to an embodiment of the present invention into the central nervous system via any suitable route. In such cases, for example, intraventricular injection or intrathecal injection is included. The intraventricular injection can be facilitated by, for example, an intraventricular catheter which is attached to a reservoir such as an Ommaya reservoir. Alternatively, pulmonary administration can be employed, for example, by use of an inhaler or nebulizer, and a formulation which includes an aerosolizing agent.

As described above, it is desirable to carry out administration such that, in regard to respective doses of active ingredients (IL-18 and one or more antibodies) per kg of body weight of a patient at one administration, the dose of IL-18 is 0.1 mg/kg while the dose of the one or more antibodies is 1 mg/kg to 20 mg/kg and more preferably 2.5 mg/kg to 5.0 mg/kg or 3.0 mg/kg to 5.0 mg/kg.

Embodiment 3: Antitumor Effect of Cancer Therapeutic Agent According to Embodiment of Present Invention As described above, a cancer therapeutic agent according to an embodiment of the present invention uses, as active ingredients, IL-18 and a predetermined antibody (or predetermined antibodies) in combination. As shown in Examples described later, administration of the cancer therapeutic agent according to an embodiment of the present invention with such combined use led to an effect of achieving a synergistic and remarkable improvement of a survival rate of mice inoculated with large intestine cancer cells which develop peritoneal metastasis, in comparison with administration with use of IL-18 alone and administration with use of the predetermined antibody alone.

Figure 4:
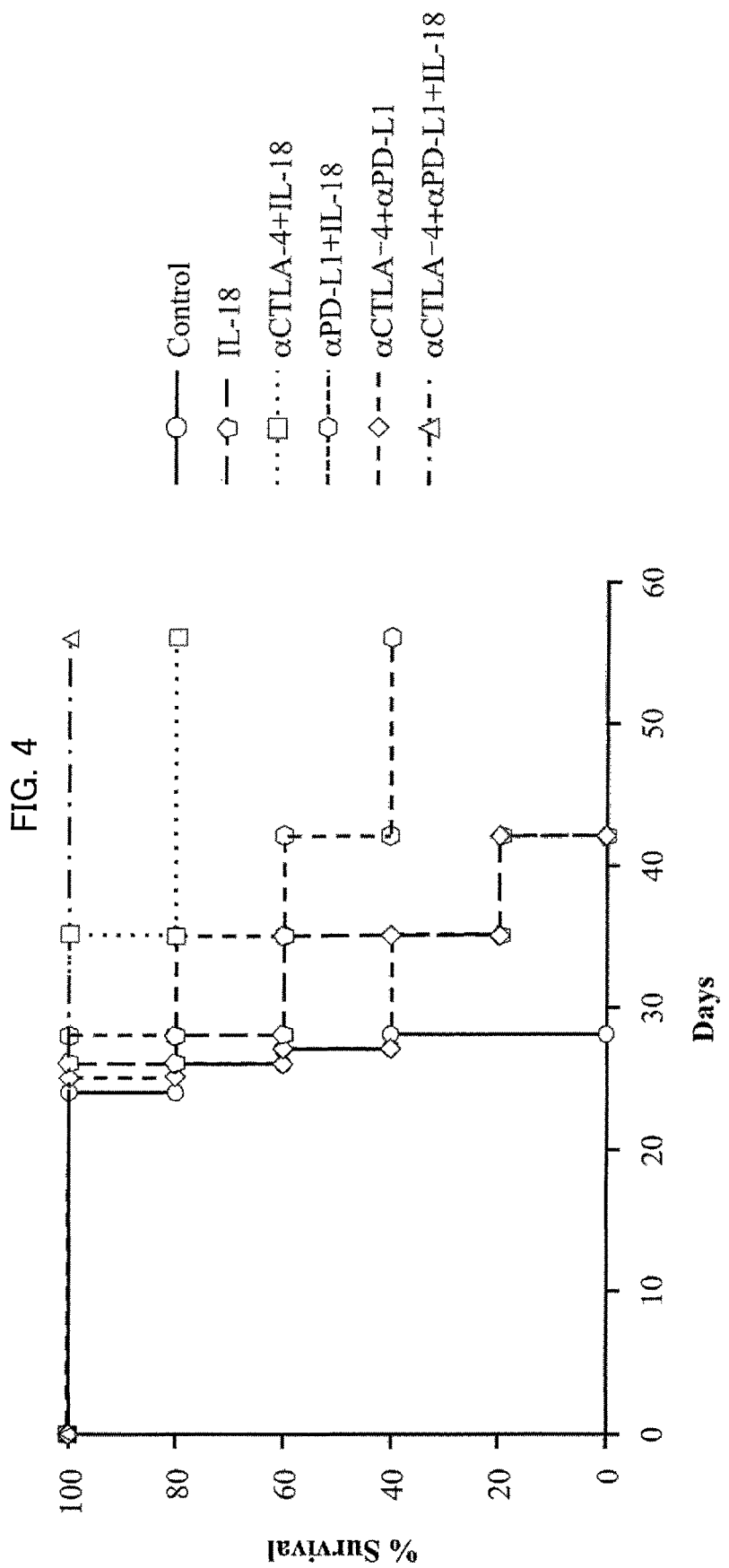
FIG. 4 is a graph showing, as survival rates of the mice, effects obtained by administrations of the therapeutic agent containing the anti-CTLA-4 antibody, the anti-PD-L1 antibody, and IL-18 and other therapeutic agents four times in total, i.e., a first administration of each therapeutic agent 7 days after the day of inoculation of the CT-26 cells, and additional three administrations of each therapeutic agent every 4 days.

In the Examples, such an effect was very strong in a case where intraperitoneal administration to mice was carried out such that a mass ratio of IL-18 and an anti-CTLA-4 antibody was arranged to be 1:25 to 1:50 while IL-18 was 2 µg/25 g and the anti-CTLA-4 antibody was in a range of 50 µg/25 g to 100 µg/25 g (FIG. 2 described later) and in a case where IL-18, an anti-PD-L1 antibody, and the anti-CTLA-4 antibody were intraperitoneally administered to mice (FIG. 4 described later).

In other words, even when 60 days had elapsed after inoculation of large intestine cancer cells to experimental mice, all the mice survived. Further, neither ascites retention nor autoimmune-like lesion was observed in the mice, and the mice stayed healthy. In other words, no side effect was considered to have occurred.

Moreover, as shown in Examples described later, the use of IL-18 in combination with the predetermined antibody (or the predetermined antibodies) could lead to sustained increase of the number of intraperitoneal exudate cells over a long period of time. Further, the intraperitoneal exudate cells were observed to have a life prolongation effect on the mice. Furthermore, growth and long-lasting presence of active NK cells were observed in the intraperitoneal exudate cells. At the same time, reduction of anti-inflammatory cells such as CD4-positive, CD25-positive T cells was observed in the intraperitoneal exudate cells.

In other words, it is presumed that since IL-18 promotes enhancement of effector cells such as NK cells and leads to a long-lasting presence of activated effector cells while decreasing anti-inflammatory cells, the cancer therapeutic agent according to an embodiment of the present invention enables further enhancement of an antitumor effect of an antibody (or antibodies) used in combination with IL-18.

In addition, though as described earlier, use of the antibody (or antibodies) alone may disadvantageously cause adverse reactions such as onset of an autoimmune disease, the cancer therapeutic agent according to an embodiment of the present invention has an advantage that the cancer therapeutic agent causes fewer adverse reactions.

In view of an excellent antitumor effect of the cancer therapeutic agent according to an embodiment of the present invention, the cancer therapeutic agent according to an embodiment of the present inventions is applicable to treatment of various cancers. Examples of the cancer types to which the cancer therapeutic agent according to an embodiment of the present invention is applicable include squamous carcinomas (e.g., cancers in cervical canal, eyelid, tunica conjunctiva, vagina lung, oral cavity, skin, urinary bladder, tongue, larynx, and gullet), and adenocarcinomas (e.g., cancers in prostate, small intestine, endometrium, cervical canal, large intestine, lung, pancreas, gullet, intestinum rectum, uterus, stomach, breast, and ovary). Further, examples of the cancer types to which the cancer therapeutic agent is applicable also include sarcomas (e.g., myogenic sacroma), leukemias, neuromas, melanomas, and lymphomas.

The invention of the present application encompasses the following inventions.

A cancer therapeutic agent according to an embodiment of the present invention includes: IL-18; and one or more antibodies selected from the group consisting of an anti-PD-L1 antibody, an anti-PD-1 antibody, an anti-PD-L2 antibody, an anti-CTLA-4 antibody, an anti-CD25 antibody, an anti-CD33 antibody, and an anti-CD52 antibody, the IL-18 and the one or more antibodies being active ingredients.

It is inferred, from results shown in Examples described later, that in the above arrangement, an antitumor effect of the one or more antibodies can be remarkably enhanced because IL-18 not only promotes growth, survival, and differentiation of effector cells but also inhibits growth of regulatory T cells. As a result, the cancer therapeutic agent according to an embodiment of the present invention can bring about a very excellent synergistic antitumor effect, in comparison with the one or more antibodies used alone or in comparison with IL-18 used alone. Moreover, the cancer therapeutic agent according to an embodiment of the present invention is very effective in inhibition of peritoneal metastasis which is difficult to treat, while having a possibility of reducing adverse reactions.

Therefore, it is possible to provide a cancer therapeutic agent which not only has a very high degree of therapeutic effect but also significantly reduces patient's pain caused by adverse reactions.

The cancer therapeutic agent according to an embodiment of the present invention is preferably arranged such that the one or more antibodies are the anti-PD-L1 antibody and/or an anti-CTLA-4 antibody.

The above arrangement uses IL-18 in combination with the anti-PD-L1 antibody and/or the anti-CTLA-4 antibody. Accordingly, in comparison with a case where only the anti-PD-L1 antibody and/or the anti-CTLA-4 antibody is/are used, the above arrangement can provide a remarkably excellent antitumor effect. Therefore, it is possible to further enhance the antitumor effect of the above one or more antibodies which have a proven effect in treatment of cancer and thereby to provide a more excellent cancer therapeutic agent.

Further, as shown in Examples described later, in a case where the one or more antibodies are the anti-PD-L1 antibody and the anti-CTLA-4 antibody in the above arrangement, the cancer therapeutic agent according to an embodiment of the present invention can provide not merely an additive effect but a very excellent synergistic antitumor effect in comparison with a cancer therapeutic agent containing IL-18 and the anti-PD-L1 antibody or the anti-CTLA-4 antibody.

Therefore, it is possible to provide a cancer therapeutic agent which not only has a more excellent antitumor effect but also causes fewer adverse reactions.

The cancer therapeutic agent according to an embodiment of the present invention is preferably arranged such that a mass of the IL-18 and a sum of a mass(es) of the one or more antibodies are in a ratio of 1:25 to 1:200.

In the above arrangement, respective doses of IL-18 and the one or more antibodies administered to a living body can be arranged to be appropriate amounts, as shown in Examples described later. Accordingly, the above arrangement is preferable for the purpose of obtaining the very excellent synergistic antitumor effect.

The cancer therapeutic agent according to an embodiment of the present invention is preferably arranged to be a therapeutic agent for one or more cancers selected from the group consisting of gastric cancer, large intestine cancer, ovarian cancer, osteosarcoma, and leukemia.

The above cancers are often associated with tumor peritoneal metastasis. Even in cases where a tumor is excised, the cancers may develop peritoneal metastasis. The above arrangement can provide a high therapeutic effect on peritoneal metastasis, as shown in Examples described later.

Therefore, it is possible to provide a cancer therapeutic agent which is suitable particularly to the above cancers associated with peritoneal metastasis and causes fewer adverse reactions.

The present invention is not limited to the embodiments, but can be altered by a skilled person in the art within the scope of the claims. An embodiment derived from a proper combination of technical means each disclosed in a different embodiment is also encompassed in the technical scope of the present invention. Further, it is possible to form a new technical feature by combining the technical means disclosed in the respective embodiments.

EXAMPLES

The following will describe the present invention in greater detail on the basis of Examples. It should be noted that the present invention is not limited by Examples below.

First, materials and experimental methods used in Examples will be described.

[Materials]
(1) Mice and Cell Line
As mice, BALB/C wild-type mice (6 to 8 weeks old, male) purchased from Japan SLC, Inc. (Hamamatsu-shi, Japan) were used. The mice were kept in a pathogen-free state under conditions of 25° C. and lighting controlled in a 12-hour light/12-hour dark cycle. The mice were fed with water and food pellets ad libitum.

A cell line of CT-26 mouse colon cancer cells was purchased from the American Type Culture Collection and was maintained, at 37° C. and in an atmosphere containing 5% $CO_2$, in RPMI1640 medium (manufactured by Nacalai Tesque, Inc.) containing 10% fetal bovine serum (FBS, BioWest) and penicillin/streptomycin (Gibco BRL, USA).

The cells were treated with $Ca^{2+}/Mg^{2+}$-free Dulbecco's PBS containing 0.05% trypsin and 0.01% EDTA (pH 7.4, manufactured by Nacalai Tesque, Inc., hereinafter referred to as "trypsin-EDTA") and were then collected.

(2) Reagents
Recombinant mouse IL-18 (manufactured by GlaxoSmithKline, item number SB-528775, hereinafter referred to simply as "IL-18") provided by courtesy of GlaxoSmithKline PLC was used.

An anti-mouse CD152/CTLA-4 monoclonal antibody (mAb, clone UC10-4F10-11, hereinafter referred to simply as "anti-CTLA-4 antibody") and an anti-mouse PD-L1 antibody (clone 10F.9G2, hereinafter referred to simply as "anti-PD-L1 antibody") were used. Both of them were purchased from BioXcell. A rabbit anti-asialo GM1 antibody (catalogue number: 014-09801, manufactured by Wako Pure Chemical Industries, Ltd.), an anti-CD8 antibody (catalogue number: SC-18913, manufactured by Santa Cruz), and rabbit IgG (catalogue number: PM035, manufactured by MBL) are all commercially available antibodies.

[Experimental Method]
(1) In Vivo Treatment
The CT-26 cells in a sub-confluent state were collected by detaching them with trypsin-EDTA from a culture vessel, and were then washed twice with PBS. The number of viable cells was counted by Trypan Blue dye exclusion test, and the viable cells were suspended in PBS in various cell concentrations to prepare corresponding suspensions. The cell concentration is $5.0 \times 10^4$ cells per 0.25 ml.

The suspension was intraperitoneally injected in an amount of 0.25 ml into each of the BALB/C wild-type mice. On an appropriate day after inoculation of the CT-26 cells, the anti-CTLA-4 antibody or the anti-PD-L1 antibody were intraperitoneally injected in various amounts (25 to 100 μg), with IL-18 (1 to 2 μg) or without IL-18, into the BALB/C wild-type mice. In order to study possible responsibility of NK cells or T cells in vivo, an anti-NK cell antibody or an anti-T cell antibody was also administered. Specific amounts of antibodies and IL-18 used in Examples and intervals of administration will be described in each Example.

(2) Preparation and Culture of Cells
Peritoneal exudate cells (PECs) of a mouse were collected from the abdominal cavity and washed in 5 ml of PBS three times. Red blood cells were eliminated by ACK lysis buffer (self-made), and the resulting cells were washed three times with PBS.

Lymphocytes were cultured, at 37° C. and in an atmosphere containing 5% $CO_2$, in RPMI1640 medium (manufactured by Nacalai Tesque, Inc.) containing 10% fetal bovine serum, L-glutamine (manufactured by Gibco BRL), penicillin/streptomycin, and 2-mercaptoethanol (M7154 manufactured by Sigma).

(3) Adoptive Cell Transfer
PECs for adoptive cell transfer experiment were prepared from abdominal cavities of mice inoculated with the CT-26 cells. Therapeutic agents prepared from various combinations of the anti-CTLA-4 antibody, the anti-PD-L1 antibody, and IL-18 were intraperitoneally injected into mice 3 days after the day of inoculation of the CT-26 cells. PECs were collected 4 days after the day of intraperitoneal injection of the therapeutic agents. Most of the collected cells were lymphocytes. The lymphocytes were washed and were then suspended in PBS to reach a cell density of $2.5 \times 10^7$ cells/ml. As a result, a cell suspension was prepared. For adoptive cell transfer, the cell suspension was intraperitoneally injected in an amount of 0.2 ml (approximately $5 \times 10^6$ cells per mouse) into each of the mice inoculated with the CT-26 cells, 3 days, 7 days, and 11 days after the day of inoculation.

(4) Flow Cytometry

Cell surface markers of PECs and cell surface markers of splenocytes were analyzed by using flow cytometry. The cell surface markers were stained with a FITC-labeled anti-CD4 antibody (manufactured by eBioscience, clone GK1.5), an APC-labeled anti-CD8 antibody (manufactured by Biolegend, clone 54-6.7), a biotin-labeled anti-CD8 antibody (manufactured by eBioscience, clone 53-6.7), a biotin-labeled anti-CD11c antibody (manufactured by Beckton Dickinson, clone HL3), an APC-labeled anti-CD45R/B220 antibody (manufactured by Biolegend, clone RA3-6B2), and/or a PE-labeled anti-CD49b antibody (manufactured by Beckton Dickinson, clone DX5). The analysis based on flow cytometry was carried out by using a FACS Calibur flow cytometer (manufactured by Beckton Dickinson Biosciences).

That is, the cells were stained with FITC-, PE-, APC-, and biotin-labeled monoclonal antibodies, which are specific to CD4, CD8, CD11c, CD45R/B220, and CD49b, and were then analyzed by using a FACS Calibur flow cytometer.

Further, an anti-mouse CD16/32 antibody (manufactured by eBioscience, clone 93) was used as a Fc blocker. Data was analyzed by using Cell Quest software (registered trademark, manufactured by Beckton Dickinson Biosciences).

Conditions for the flow cytometry herein are fixed ones, which are based on the conditions described in Becton-Dickinson immunocytometry systems, 1995. As used herein, all expression intensities of cell surface markers mean expression intensities measured by flow cytometry.

Example 1: Effect of Cancer Therapeutic Agent Containing Anti-CTLA-4 Antibody and IL-18 on Survival Rate of Mice Intraperitoneally Administered with CT-26 Cells The suspension containing the CT-26 cells described above in (1) of [Experimental method] in cell concentration of $5.0 \times 10^4$ cells per 0.25 ml was inoculated by intraperitoneal injection in an amount of 0.25 ml into each of the BALB/C wild-type mice.

The mice were divided into the following groups: a control group to which 100 µg of rabbit IgG was to be administered as a therapeutic agent; a group to which 2 µg of IL-18 alone was to be administered as a therapeutic agent; a group to which 100 µg of anti-CTLA-4 antibody alone was to be administered as a therapeutic agent; and a group to which 100 µg of anti-CTLA-4 antibody and 2 µg of IL-18 were to be administered as a therapeutic agent. Each group was made up of five mice. The therapeutic agents were intraperitoneally injected into the mice four times in total, i.e., 3 days, 7 days, 10 days, and 14 days after the day of injection of the CT-26 cells. Hereinafter, in all of the Examples, the experiment was repeated three times.

It should be noted that each dose (µg) of the rabbit IgG antibody, the anti-CTLA-4 antibody, and IL-18 is a dose per 25 g of body weight of a mouse.

FIG. 1 is a graph showing results of monitoring, as a survival rate of mice, an effect resulting from administration of the cancer therapeutic agent containing the anti-CTLA-4 antibody and IL-18 3 days and later days after the day of inoculation of the CT-26 cells. In FIG. 1, a horizontal axis represents the number of days elapsed from the day of inoculation (intraperitoneal injection) of the CT-26 cells, while a vertical axis represents a survival rate of the mice.

As shown in FIG. 1, the control group had a survival rate that began to decrease 24 days after the day of inoculation of the CT-26 cells, and all the mice in the control group died within 27 days after the day of inoculation of the CT-26 cells. Further, the group administered with IL-18 alone and the group administered with the anti-CTLA-4 antibody alone showed a similar tendency toward a decreased survival rate, and all the mice in the group administered with IL-18 alone died within 42 days after the day of inoculation of the CT-26 cells, and all the mice in the group administered with the anti-CTLA-4 antibody alone died within 49 days after the day of inoculation of the CT-26 cells.

In contrast, in the group administered with the anti-CTLA-4 antibody and IL-18, no retained ascites and no death of the mice were observed. All the mice in that group survived even after 60 days from the day of inoculation of the CT-26 cells. Moreover, the mice in that group stayed healthy without showing deterioration.

The above results revealed that, in the group administered with the anti-CTLA-4 antibody and IL-18, a very excellent synergistic antitumor effect is provided rather than merely an additive antitumor effect provided by IL-18 and the anti-CTLA-4 antibody. In other words, it was revealed that the use of IL-18 in combination with the anti-CTLA-4 antibody enables dramatic enhancement of the antitumor effect of the anti-CTLA-4 antibody.

Example 2: Dose Effect of Anti-CTLA-4 Antibody and IL-18

The suspension containing the CT-26 cells described above in (1) of [Experimental method] in cell concentration of $5.0 \times 10^4$ cells per 0.25 ml was inoculated by intraperitoneal injection in an amount of 0.25 ml into each of the BALB/C wild-type mice.

The mice were divided into the following groups: a control group to which 100 µg of rabbit IgG was to be administered as a therapeutic agent; a group to which 25 µg of anti-CTLA-4 antibody and 2 µg of IL-18 were to be administered as a therapeutic agent; a group to which 50 µg of anti-CTLA-4 antibody and 2 µg of IL-18 were to be administered as a therapeutic agent; a group to which 100 µg of anti-CTLA-4 antibody and 2 µg of IL-18 were to be administered as a therapeutic agent; and a group to which 100 µg of anti-CTLA-4 antibody and 1 µg of IL-18 were to be administered as a therapeutic agent. Each group was made up of five mice. The therapeutic agents were intraperitoneally injected into the mice four times in total, i.e., 3 days, 7 days, 10 days, and 14 days after the day of injection of the CT-26 cells.

It should be noted that each dose (µg) of the rabbit IgG antibody, the anti-CTLA-4 antibody, and IL-18 is a dose per 25 g of body weight of a mouse.

Figure 2:
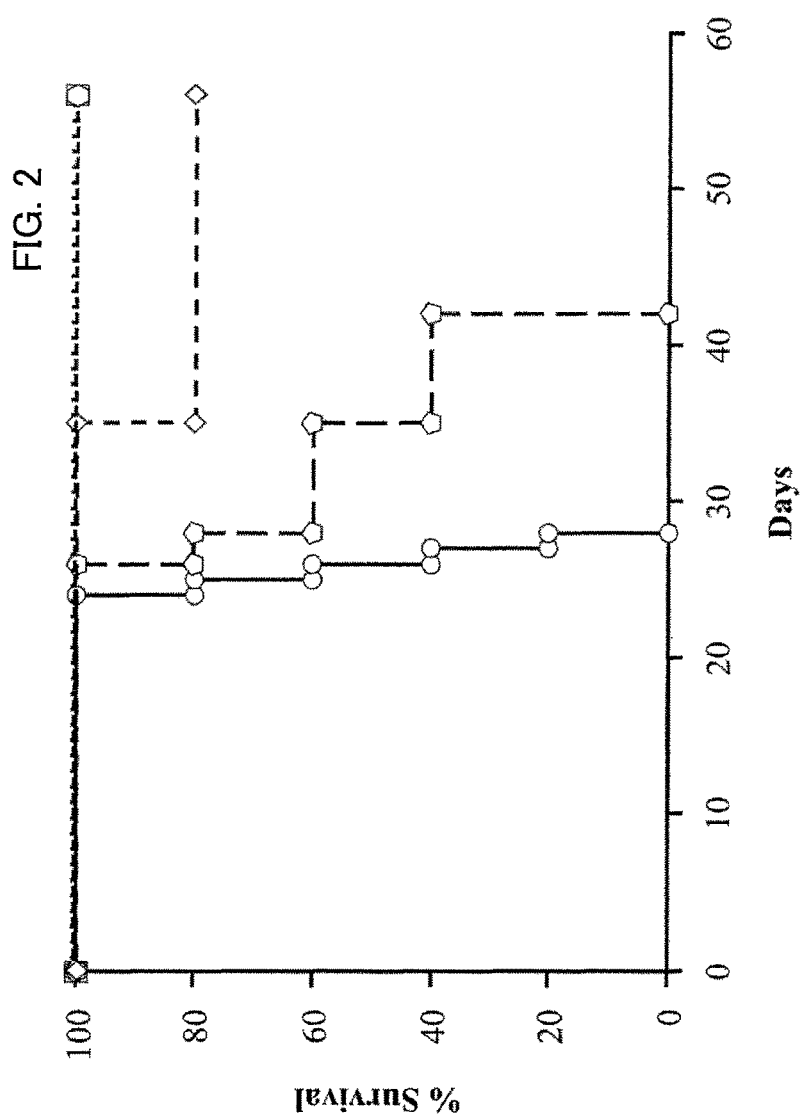
FIG. 2 is a graph showing a dose effect of the anti-CTLA-4 antibody and IL-18, as in Example 1, as a survival rate of the mice intraperitoneally administered with the CT-26 cells.

FIG. 2 is a graph showing a dose effect of the anti-CTLA-4 antibody and IL-18, as in Example 1, as a survival rate of the mice intraperitoneally administered with the CT-26 cells. Horizontal and vertical axes are the same as those in FIG. 1.

As shown in FIG. 2, the control group had a survival rate that began to decrease 24 days after the day of inoculation of the CT-26 cells, and all the mice in the control group died within 28 days after the day of inoculation of the CT-26 cells.

In contrast, in the groups administered with the anti-CTLA-4 antibody and IL-18, the group administered with 25 µg of anti-CTLA-4 antibody and 2 µg of IL-18 had a survival rate that began to decrease 28 days after the day of inoculation of the CT-26 cells, and all the mice in that group died within 42 days after the day of inoculation of the CT-26 cells. The group administered with 25 µg of anti-CTLA-4 antibody and 2 µg of IL-18, however, showed a life prolongation effect, in comparison with the control group.

The group administered with 100 µg of anti-CTLA-4 antibody and 1 µg of IL-18 had a survival rate that decreased to 80% 35 days after the day of inoculation of the CT-26 cells but maintained that level even after 60 days from the day of inoculation of the CT-26 cells. The surviving mice were in good health.

In the group administered with 50 µg of anti-CTLA-4 antibody and 2 µg of IL-18 and the group administered with 100 µg of anti-CTLA-4 antibody and 2 µg of IL-18, all the mice survived even after 60 days from the day of the administration. The mice were in good health.

As described above, the use of the anti-CTLA-4 antibody in combination with IL-18 achieved a very excellent antitumor effect in three of the four administration groups. As a result, a high degree of therapeutic effect was obtained. Further, it was confirmed that the group administered with 25 µg of anti-CTLA-4 antibody and 2 µg of IL-18 also provided a life prolongation effect.

Example 3: Effect of Therapeutic Agent Containing Anti-PD-L1 Antibody and IL-18 on Survival Rate of Mice Intraperitoneally Inoculated with CT-26 Cells The suspension containing the CT-26 cells in the same cell concentration ($5.0\times10^4$ cells per 0.25 ml) as that used in Example 1 was inoculated by intraperitoneal injection in an amount of 0.25 ml into each of the BALB/C wild-type mice.

The mice were divided into the following groups: a control group to which 100 µg of rabbit IgG was to be administered as a therapeutic agent; a group to which 2 µg of IL-18 alone was to be administered as a therapeutic agent; a group to which 100 µg of anti-PD-L1 antibody alone was to be administered as a therapeutic agent; and a group to which 100 µg of anti-PD-L1 antibody and 2 µg of IL-18 were to be administered as a therapeutic agent. Each group was made up of five mice. The therapeutic agents were intraperitoneally injected into the mice four times in total, i.e., 3 days, 7 days, 10 days, and 14 days after the day of injection of the CT-26 cells. It should be noted that each of the doses is an amount per 25 g of body weight of a mouse.

Figure 3:
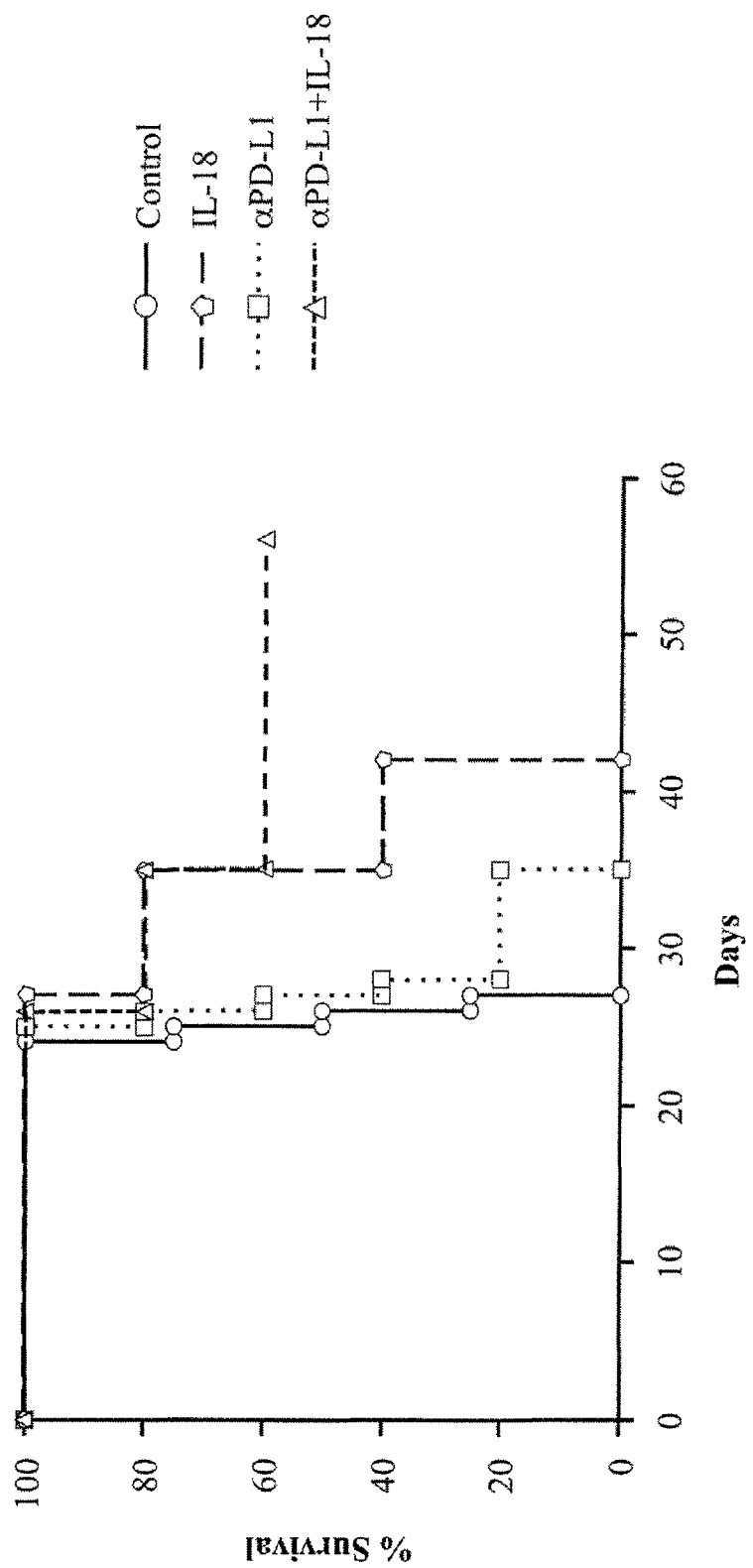
FIG. 3 is a graph showing an effect of a cancer therapeutic agent containing an anti-PD-L1 antibody and IL-18, as in Example 1, as a survival rate of the mice.

FIG. 3 is a graph showing an effect of the cancer therapeutic agent containing the anti-PD-L1 antibody and IL-18, as in Example 1, as a survival rate of the mice. Horizontal and vertical axes are the same as those in FIG. 1.

As shown in FIG. 3, the control group and the group administered with IL-18 alone had survival rates that changed in the same way as in Example 1. The group administered with the anti-PD-L1 antibody and IL-18 showed the same tendency as that of the group administered with IL-18 alone before the elapse of 35 days from the day of inoculation of the CT-26 cells. However, after the elapse of 35 days from the day of inoculation of the CT-26 cells, all the mice in the group administered with IL-18 alone died within 42 days after the day of inoculation of the CT-26 cells, whereas the group administered with the anti-PD-L1 antibody and IL-18 maintained a 60% survival rate even after the elapse of 60 days. Moreover, the surviving mice were in good health.

The survival rate of the group administered with the anti-PD-L1 antibody alone was lower than that of the group administered with IL-18 alone. The above results revealed that the administration of the anti-PD-L1 antibody and IL-18, that is, the use of the therapeutic agent containing the anti-PD-L1 antibody and IL-18 provides a very excellent synergistic antitumor effect rather than merely an additive antitumor effect provided by IL-18 and the anti-PD-L1 antibody.

In other words, it was revealed that the use of IL-18 in combination with the anti-PD-L1 antibody enables dramatic enhancement of the antitumor effect of the anti-PD-L1 antibody. Further, the anti-PD-L1 antibody is known to cause fewer adverse reactions than the anti-CTLA-4 antibody. Consequently, thanks to the synergistic antitumor effect, it is possible to provide a cancer therapeutic agent that has a high degree of antitumor effect and causes fewer adverse reactions.

Example 4: Effect 1 of Cancer Therapeutic Agent Containing Anti-PD-L1 Antibody, Anti-CTLA-4 Antibody, and IL-18 on Survival Rate of Mice Intraperitoneally Inoculated with CT-26 Cells The suspension containing the CT-26 cells in the same cell concentration ($5.0\times10^4$ cells per 0.25 ml) as that used in Example 1 was inoculated by intraperitoneal injection in an amount of 0.25 ml into each of the BALB/C wild-type mice.

The mice were divided into the following groups: a control group to which 100 µg of rabbit IgG was to be administered as a therapeutic agent; a group to which 2 µg of IL-18 alone was to be administered as a therapeutic agent; a group to which 100 µg of anti-CTLA-4 antibody and 2 µg of IL-18 were to be administered as a therapeutic agent; a group to which 100 µg of anti-PD-L1 antibody and 2 µg of IL-18 were to be administered as a therapeutic agent; and a group to which 100 µg of anti-CTLA-4 antibody, 100 µg of anti-PD-L1 antibody, and 2 µg of IL-18 were to be administered as a therapeutic agent. Each group was made up of five mice. Intraperitoneal injection of each therapeutic agent was carried out four times in total. That is, a first intraperitoneal injection of each of the therapeutic agents was carried out 7 days after the day of injection of the CT-26 cells. Thereafter, additional three intraperitoneal injections of each therapeutic agent were carried out every 4 days.

FIG. 4 is a graph showing, as survival rates of the mice, effects obtained by administrations of the therapeutic agent containing the anti-CTLA-4 antibody, the anti-PD-L1 antibody, and IL-18 and other therapeutic agents four times in total, i.e., a first administration of each therapeutic agent 7 days after the day of inoculation of the CT-26 cells, and additional three administrations of each therapeutic agent every 4 days. Horizontal and vertical axes are the same as those in FIG. 1. It should be noted that each of the doses is an amount per 25 g of body weight of a mouse.

Example 4, unlike Examples 1 to 3, initiated the administration of the therapeutic agents 7 days after the day of intraperitoneal inoculation of the CT-26 cells. That is, the administration of the therapeutic agents was initiated after tumors were grown more relative to Examples 1 to 3. As shown in FIG. 4, the group administered with the anti-CTLA-4 antibody and IL-18 and the group administered with the anti-PD-L1 antibody and IL-18 showed very high survival rates in comparison with the group administered with the anti-CTLA-4 antibody and the anti-PD-L1 antibody. Moreover, the surviving mice were in good health.

Further, in the group administered with the anti-CTLA-4 antibody, the anti-PD-L1 antibody, and IL-18, a notable result was obtained. That is, although the administration was initiated after 7 days from intraperitoneal inoculation (tumor transplantation) of the CT-26 cells, all the mice survived even after 60 days from the administration. Moreover, the surviving mice were in very good health.

Figure 5:
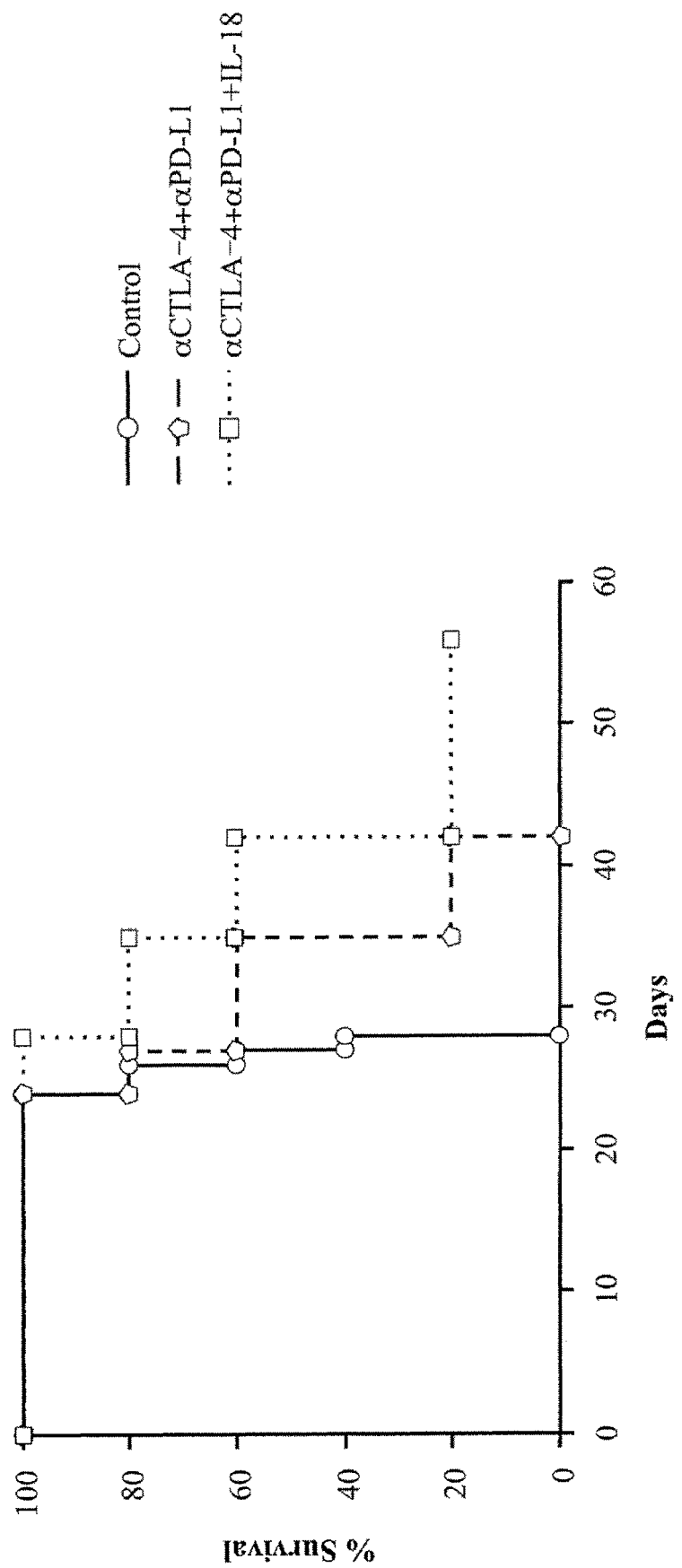
FIG. 5 is a graph showing, as survival rates of the mice, effects obtained by administrations of the therapeutic agent containing the anti-CTLA-4 antibody, the anti-PD-L1 antibody, and IL-18 and other therapeutic agents 14 days after the day of inoculation of the CT-26 cells.

Example 5: Effect 2 of Cancer Therapeutic Agent Containing Anti-PD-L1 Antibody, Anti-CTLA-4 Antibody, and IL-18 on Survival Rate of Mice Intraperitoneally Inoculated with CT-26 Cells FIG. 5 is a graph showing, as survival rates of the mice, effects obtained by administrations of the therapeutic agent containing the anti-CTLA-4 antibody, the anti-PD-L1 antibody, and IL-18 and other therapeutic agents 14 days after the day of inoculation of the CT-26 cells. Horizontal and vertical axes are the same as those in FIG. 1.

An experiment was carried out as in Example 4, except that Example 5 used the following therapeutic agents used in Example 4: 100 μg of the control; 100 μg of anti-CTLA-4 antibody and 100 μg of anti-PD-L1 antibody; and 100 μg of anti-CTLA-4 antibody, 100 μg of anti-PD-L1 antibody, and 2 μg of IL-18, and the therapeutic agents were intraperitoneally injected 14 days after the day of intraperitoneal inoculation of the CT-26 cells. It should be noted that each of the above doses is an amount per 25 g of a body weight of a mouse.

As shown in FIG. 5, it can be seen that administration of the anti-CTLA-4 antibody, the anti-PD-L1 antibody, and IL-18 as a cancer therapeutic agent provides a higher survival rate in comparison with administration of the anti-CTLA-4 antibody and the anti-PD-L1 antibody.

In Example 5, administration of the cancer therapeutic agent was initiated 14 days after the tumor transplantation. For this reason, tumor masses were formed by the time the cancer therapeutic agent was administered, and retained ascites was also observed. Despite that fact, in a case where the anti-CTLA-4 antibody, the anti-PD-L1 antibody, and IL-18 were used, an apparent life prolongation effect was observed. This suggests that the therapeutic agent containing the anti-CTLA-4 antibody, the anti-PD-L1 antibody, and IL-18 is capable of achieving a therapeutic effect even in a case where the therapeutic agent is administered after tumor masses have been formed.

Example 6: Changes in Number of Peritoneal Exudate Cells

Example 6 shows that the anti-CTLA-4 antibody and IL-18; the anti-PD-L1 antibody and IL-18; and the anti-CTLA-4 antibody, the anti-PD-L1 antibody, and IL-18 enable an increase in number of peritoneal exudate cells (PECs) of mice inoculated with CT-26 cells.

The suspension containing the CT-26 cells in the same cell concentration ($5.0 \times 10^4$ cells per 0.25 ml) as that used in Example 1 was intraperitoneally injected in an amount of 0.25 ml into each of the BALB/C wild-type mice. Three days after the day of the injection, therapeutic agents listed below were intraperitoneally injected into the mice. Sixteen mice were prepared for each type of therapeutic agent. One to four days after the day of administration of each therapeutic agent, PECs were collected from 4 mice for each day and were counted by using a counter, and an average value of the number of PECs of the 4 mice was then determined.

Figure 6:
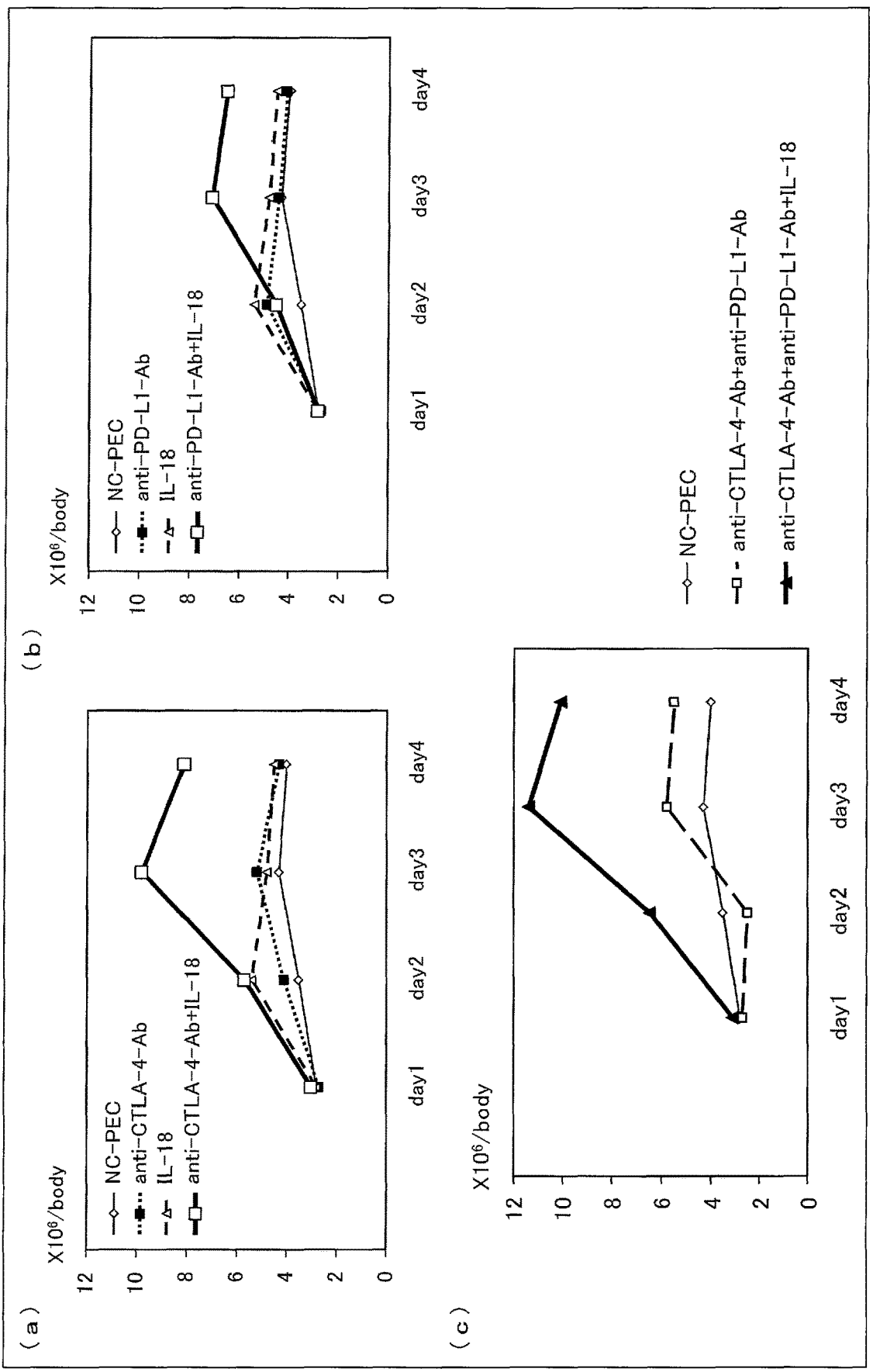
FIG. 6 is a set of graphs showing 4-day changes in number of peritoneal exudate cells (PECs) of the mice individually administered with a) the anti-CTLA-4 antibody and IL-18;b) the anti-PD-L1 antibody and IL-18; and c) the anti-CTLA-4 antibody, the anti-PD-L1 antibody, and IL-18 3 days after the day of inoculation of the CT-26 cells.

FIG. 6 is a set of graphs showing 4-day changes in number of peritoneal exudate cells (PECs) of the mice individually administered with the anti-CTLA-4 antibody and IL-18; the anti-PD-L1 antibody and IL-18; and the anti-CTLA-4 antibody, the anti-PD-L1 antibody, and IL-18 3 days after the day of inoculation of the CT-26 cells. A horizontal axis represents the number of days elapsed from the day of administration of the therapeutic agents, while a vertical axis represents the number of PECs per mouse (average value of the number of PECs of 4 mice).

(a) of FIG. 6 shows changes in number of PECs in the following groups: a control group administered with 100 μg of rabbit IgG as a therapeutic agent; a group administered with 100 μg of anti-CTLA-4 antibody alone as a therapeutic agent; a group administered with 2 μg of IL-18 alone as a therapeutic agent; and a group administered with 100 μg of anti-CTLA-4 antibody and 2 μg of IL-18 as a therapeutic agent.

(b) of FIG. 6 shows changes in number of PECs in the following groups: the control group administered with 100 μg of rabbit IgG as a therapeutic agent; a group administered with 100 μg of anti-PD-L1 antibody alone as a therapeutic agent; a group administered with 2 μg of IL-18 alone as a therapeutic agent; and a group administered with 100 μg of anti-PD-L1 antibody and 2 μg of IL-18 as a therapeutic agent.

(c) of FIG. 6 shows changes in number of PECs in the following groups: the control group administered with 100 μg of rabbit IgG as a therapeutic agent; a group administered with 100 μg of anti-CTLA-4 antibody and 100 μg of anti-PD-L1 antibody as a therapeutic agent; and a group administered with 100 μg of anti-CTLA-4 antibody, 100 μg of anti-PD-L1 antibody, and 2 μg of IL-18 as a therapeutic agent. In (a), (b), and (c) of FIG. 6, "NE-PEC" indicates peritoneal exudate cells of the mice administered with rabbit IgG as a control. It should be noted that each of the above doses is an amount per 25 g of a body weight of a mouse.

From all of (a) to (c) of FIG. 6, it can be seen that administration of the antibody (antibodies) and IL-18 enables a significant increase in number of PECs in comparison with administration of the antibody (antibodies) alone.

Further, 4 days after the administration of the following cancer therapeutic agents: the anti-CTLA-4 antibody and the anti-PD-L1 antibody; the anti-CTLA-4 antibody and IL-18; the anti-PD-L1 antibody and IL-18; and the anti-CTLA-4 antibody, the anti-PD-L1 antibody, and IL-18, an additional administration of these cancer therapeutic agents to the mice was carried out, and changes in number of PECs of the mice were also monitored. Doses of the cancer therapeutic agents in the first and second administrations are equal to those as shown in FIG. 6.

Figure 7:
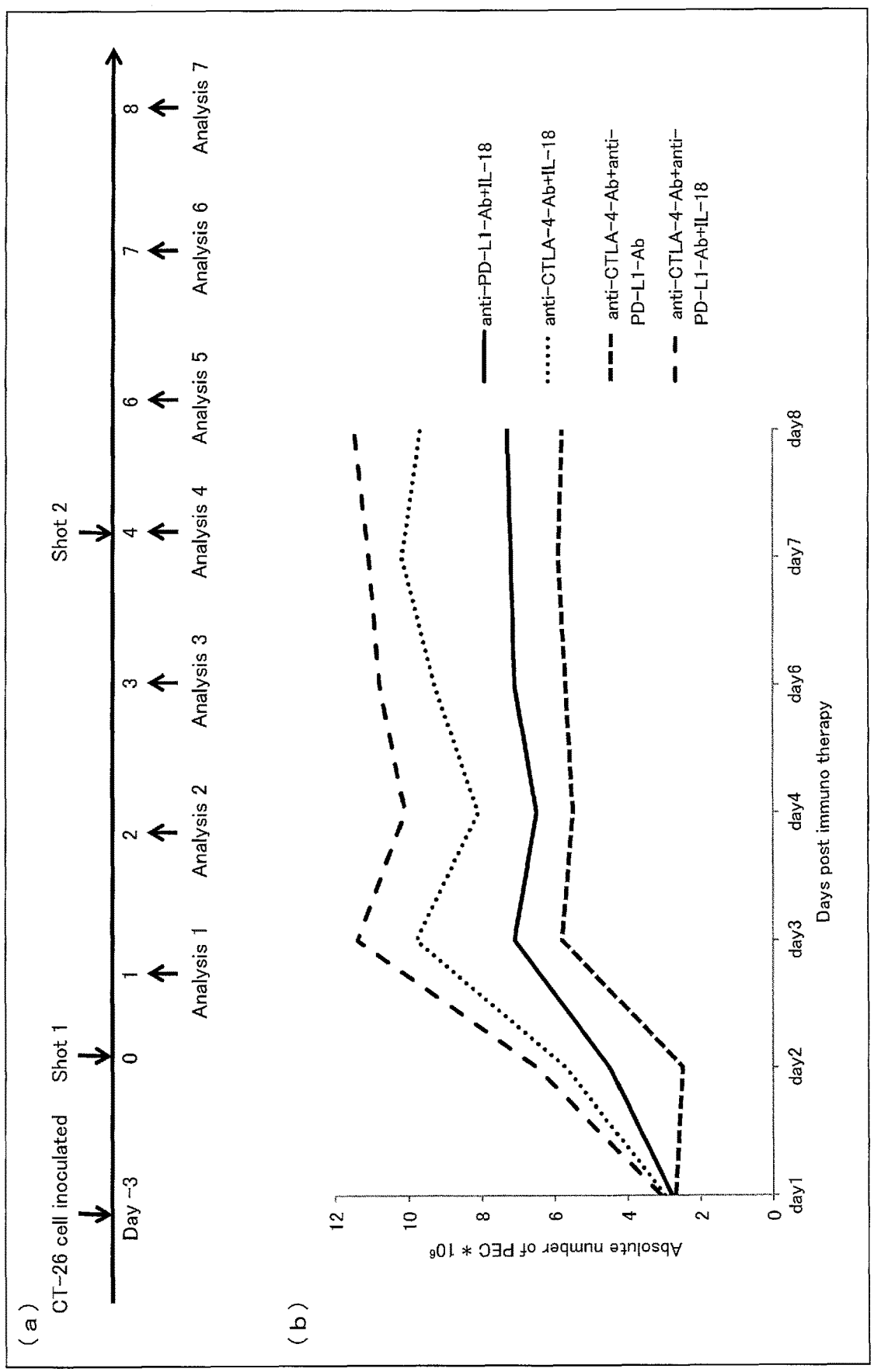
FIG. 7 shows a) the day of the first administration of the cancer therapeutic agents as the 0th day (indicated as "Shot 1" in FIG. 7a), the day on which the CT-26 cells were intraperitoneally inoculated (indicated as "CT-26 cell inoculated" in FIG. 7a), the days on which PECs were collected and analyzed (indicated as "1" to "8" and "Analysis 1" to "Analysis 7", respectively, in FIG. 7a), and the day of the second administration of the cancer therapeutic agents (indicated as "Shot 2" in FIG. 7a); and b a graph showing changes in number of PECs of the mice individually administered with the following cancer therapeutic agents: the anti-CTLA-4 antibody and the anti-PD-L1 antibody; the anti-CTLA-4 antibody and IL-18; the anti-PD-L1 antibody and IL-18; and the anti-CTLA-4 antibody, the anti-PD-L1 antibody, and IL-18, and additionally administrated with these cancer therapeutic agents 4 days after the previous administration.

FIG. 7 shows the results. (a) of FIG. 7 shows the day of the first administration of the cancer therapeutic agents as the 0th day (indicated as "Shot 1" in FIG. 7), the day on which the CT-26 cells were intraperitoneally inoculated (indicated as "CT-26 cell inoculated" in FIG. 7), the days on which PECs were collected and analyzed (indicated as "1" to "8" and "Analysis 1" to "Analysis 7", respectively, in FIG. 7), and the day of the second administration of the cancer therapeutic agents (indicated as "Shot 2" in FIG. 7).

(b) of FIG. 7 shows the number of PECs per mouse (average value of the number of PECs of 4 mice) on the 0th to 8th days shown in (a) of FIG. 7. The results on the 1st to 4th days are identical to those shown in FIG. 6.

From (b) of FIG. 7, it can be seen that the number of PECs had begun to decrease 4 days after the day of administration of the cancer therapeutic agent, but showed an upward tendency again as a result of the additional administration of the cancer therapeutic agents on the same day. Further, the number of PECs was increased more in a case where the antibodies and IL-18 were used in combination than a case where the anti-CTLA-4 antibody and the anti-PD-L1 antibody were used. The number of PECs was increased most in a case where the anti-CTLA-4 antibody, the anti-PD-L1 antibody, and IL-18 were used.

Example 7: Life Prolongation Effect of Peritoneal Exudate Cells

The suspension containing the CT-26 cells in the same cell concentration ($5.0 \times 10^4$ cells per 0.25 ml) as that used in Example 1 was inoculated by intraperitoneal injection in an amount of 0.25 ml into each of the BALB/C wild-type mice. Then, as described above in (3) of [Experimental method], cancer therapeutic agents were intraperitoneally injected 3 days after the day of inoculation of the CT-26 cells. As the cancer therapeutic agents, rabbit IgG; the anti-CTLA-4 antibody and the anti-PD-L1 antibody; and the anti-CTLA-4 antibody, the anti-PD-L1 antibody, and IL-18 were used in amounts described in the section that mentioned (c) of FIG. 6 in Example 6.

As described above in (3) of [Experimental method], PECs were collected 4 days after the day of intraperitoneal injection of the therapeutic agents, and cell suspensions of the PECs were prepared. Three days, 7 days, and 11 days after the day of the inoculation, each of the cell suspensions (approximately $5.0 \times 10^6$ cells per mouse) was intraperitoneally injected in an amount of 0.2 ml into the mice inoculated with the CT-26 cells.

Figure 8:
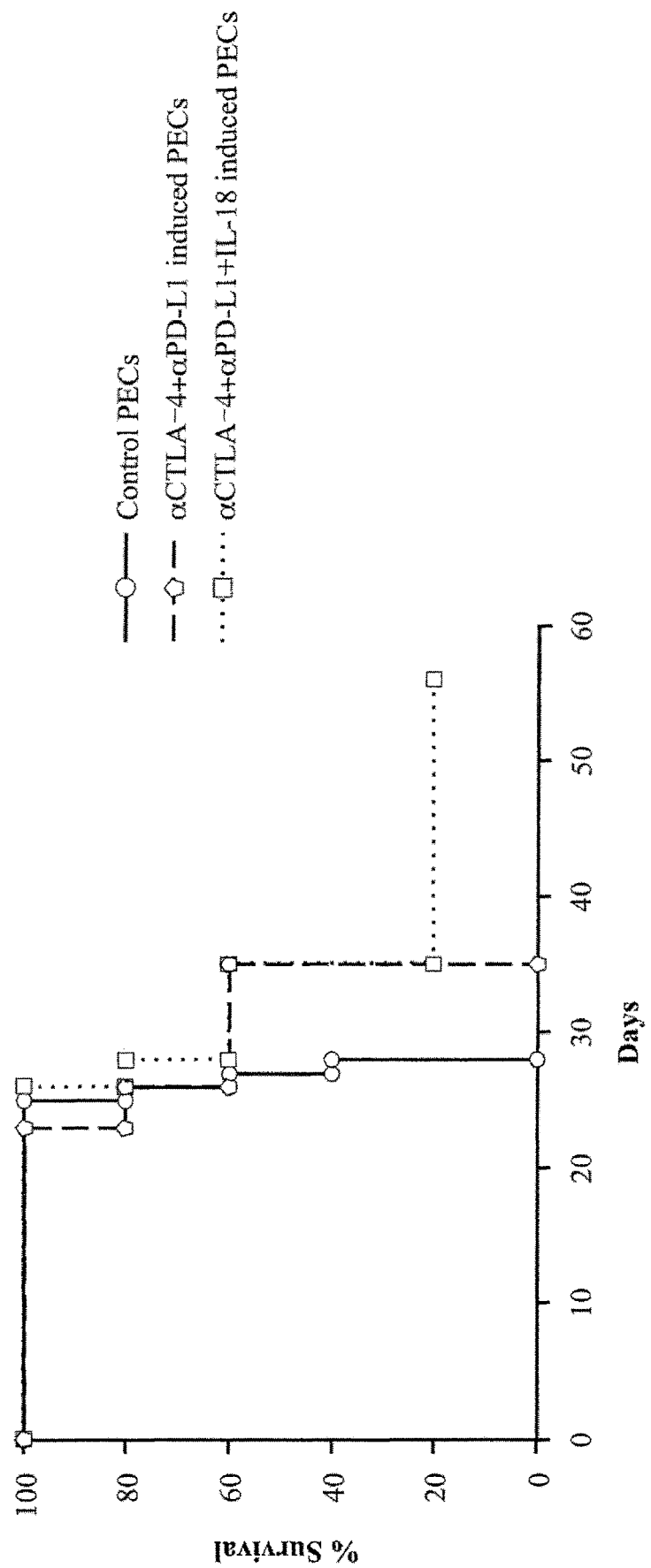
FIG. 8 is a graph showing a life prolongation effect obtained by adoptive cell transfer of PECs into the tumor-bearing mice, the PECs being induced by the anti-CTLA-4 antibody, the anti-PD-L1 antibody, and IL-18.

FIG. 8 is a graph showing a life prolongation effect obtained by adoptive cell transfer of PECs into the tumor-bearing mice, the PECs being induced by the anti-CTLA-4 antibody, the anti-PD-L1 antibody, and IL-18. The horizontal axis represents the number of days elapsed from the day of intraperitoneal administration of PECs, while the vertical axis represents the survival rate of the mice.

In addition, the legend "control PECs" indicates the result of the PECs obtained by administration of the rabbit IgG as a therapeutic agent. The legend "αCTLA-4+αPD-L1 induced PECs" indicates the result of the PECs (hereinafter referred to as "PEC-1" in this section) induced by administration of the anti-CTLA-4 antibody and the anti-PD-L1 antibody as a therapeutic agent. The legend "αCTLA-4+αPD-L1+IL-18 induced PECs" indicates the result of the PECs (hereinafter referred to as "PEC-2" in this section) induced by administration of the anti-CTLA-4 antibody, the anti-PD-L1 antibody, and IL-18 as a therapeutic agent.

As can be seen from FIG. 8, all the mice in the control died within 28 days after the day of intraperitoneal administration of the PECs. The mice administered with PEC-1 showed a higher life prolongation effect in comparison with the control, but all of the mice administered with PEC-1 died within 35 days after the day of intraperitoneal administration of PEC-1. On the other hand, the mice administered with PEC-2 showed a 20% survival rate even after 58 days from the day of PEC-2 administration and showed a slightly higher life prolongation effect in comparison with the mice administered with PEC-1.

That is, it is presumed that the use of the anti-CTLA-4 antibody and the anti-PD-L1 antibody in combination with IL-18 enabled PECs having a more excellent antitumor effect to be induced, and consequently achieved a more excellent life prolongation effect than the use of the anti-CTLA-4 antibody and the anti-PD-L1 antibody.

Example 8: Enhancement of NK Cells in Peritoneal Exudate Cells

In Example 8, flow cytometry was used to examine traits of the peritoneal exudate cells induced by intraperitoneally administrating to the mice in the same manner as in Example 6 the following therapeutic agents out of the therapeutic agents used in Example 6: the anti-PD-L1 antibody alone; IL-18 alone; the anti-PD-L1 antibody and IL-18; the anti-CTLA-4 antibody and the anti-PD-L1 antibody; and the anti-CTLA-4 antibody, the anti-PD-L1 antibody, and IL-18. The peritoneal exudate cells subjected to flow cytometry were cells collected from 5 mice for each therapeutic agent 4 days after the day of administration of the therapeutic agents.

Flow cytometry was carried out using an APC-labeled anti-CD45R/B220 antibody (manufactured by Biolegend, clone RA3-6B2), an anti-NKG2D antibody (BD-pharmingem562347), and a PE-labeled anti-CD49b antibody (manufactured by Beckton Dickinson, clone DX5) by the method provided above in (4) of [Experimental method].

Figure 9:
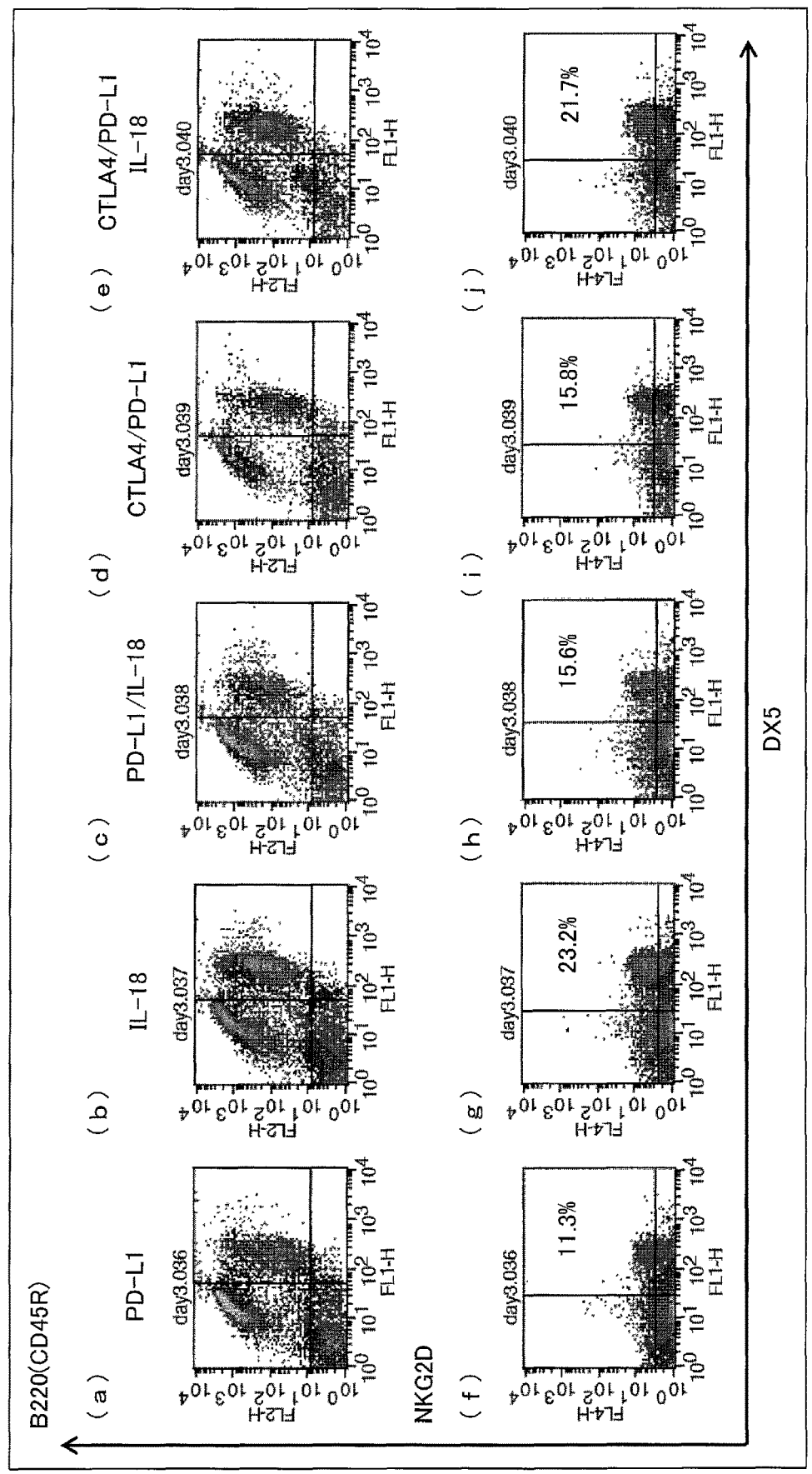
FIG. 9 is a set of graphs showing results of a study on expression intensities of B220 (CD45R), NKG2D, and DX5 (CD49b) on PECs induced by intraperitoneally administrating to the mice the following cancer therapeutic agents: the anti-PD-L1 antibody alone; IL-18 alone; the anti-PD-L1 antibody and IL-18; the anti-CTLA-4 antibody and the anti-PD-L1 antibody; and the anti-CTLA-4 antibody, the anti-PD-L1 antibody, and IL-18. The horizontal axis of each of (a) to (j) indicates the expression intensity of DX5. The vertical axis of each of (a) to (e) indicates the expression intensity of B220 (CD45R). The vertical axis of each of (f) to (j) indicates the expression intensity of NKG2D. (a) and (f) each show the result of a case involving use of the anti-PD-L1 antibody alone. (b) and (g) each show the result of a case involving use of IL-18 alone. (c) and (h) each show the result of a case involving use of the anti-PD-L1 antibody and IL-18. (d) and (i) each show the result of a case involving use of the anti-CTLA-4 antibody and the anti-PD-L1 antibody. (e) and (j) each show the result of a case involving use of the anti-CTLA-4 antibody, the anti-PD-L1 antibody, and IL-18.

FIG. 9 is a set of graphs showing results of a study on expression intensities of surface markers B220 (CD45R), NKG2D, and DX5 (CD49b). Horizontal axes in (a) to (j) represent expression intensities of DX5, vertical axes in (a) to (e) represent expression intensities of B220 (CD45R), and vertical axes in (f) to (j) represent expression intensities of NKG2D. Notations such as "day 3.036" in (a) to (j) indicate that PECs collected 3 days after the day of administration of the therapeutic agents were analyzed.

As shown in FIG. 9, (a) to (e) of FIG. 9 each have four separate areas. It can be said that cells present in the upper right area have higher B220 (CD45R) expression intensities and higher DX5 expression intensities. Meanwhile, (f) to (j) of FIG. 9 each have four separate areas. It can be said that cells present in the upper right area have higher NKG2D expression intensities and higher DX5 expression intensities.

Comparison of (a) and (b) of FIG. 9 with (c) of FIG. 9 shows that the use of the anti-PD-L1 antibody and IL-18 (shown in (c) of FIG. 9) results in a larger number of cells present in the upper right area. Further, comparison of (d) of FIG. 9 with (e) of FIG. 9 shows that the use of the anti-CTLA-4 antibody, the anti-PD-L1 antibody, and IL-18 (shown in (e) of FIG. 9) results in a larger number of cells present in the upper right area.

Then, as shown in (h) of FIG. 9, the use of the anti-PD-L1 antibody and IL-18 results in a lower percentage of the cells present in the upper right area than the use of IL-18 alone shown in (g). However, as can be seen by comparison between (i) and (j) of FIG. 9, the use of the anti-CTLA-4 antibody, the anti-PD-L1 antibody, and IL-18 results in a higher percentage of the cells present in the upper right area than the use of the anti-CTLA-4 antibody and the anti-PD-L1 antibody. Therefore, it can be seen that the use of the antibodies in combination with IL-18 further enhances intraperitoneal induction of NK cells by the antibodies.

Thus, the results shown in (a) to (j) of FIG. 9 revealed that the use of the antibodies in combination with IL-18 enhances intraperitoneal induction of NK cells having high B220 (CD45R), NKG2D, and DX5 expression intensities, i.e., active NK cells, among all NK cells. This is considered Example 9: Maintenance of NK Cells Intraperitoneally Induced into Mice In Example 9, a study was conducted on whether administration of the anti-CTLA-4 antibody, the anti-PD-L1 antibody, and IL-18 as a cancer therapeutic agent enables intraperitoneally induced NK cells to be maintained even after a long time period has elapsed since the administration.

The suspension containing the CT-26 cells in the same cell concentration ($5.0 \times 10^4$ cells per 0.25 ml) as that used in Example 1 was intraperitoneally injected in an amount of 0.25 ml into each of the BALB/C wild-type mice. Three days after the day of the injection, therapeutic agents listed below were intraperitoneally injected.

The following therapeutic agents: the anti-CTLA-4 antibody and the anti-PD-L1 antibody; and the anti-CTLA-4 antibody, the anti-PD-L1 antibody, and IL-18 were intraperitoneally administered to the mice in the same manner as in Example 6. PECs collected 11 days after the day of the administration were analyzed.

Flow cytometry was carried out using the APC-labeled anti-CD45R/B220 antibody (manufactured by Biolegend, clone RA3-6B2), the PE-labeled anti-CD49b antibody (manufactured by Beckton Dickinson, clone DX5), and the anti-NKG2D antibody (BD-pharmingem562349) by the method provided above in (4) of [Experimental method].

Figure 10:
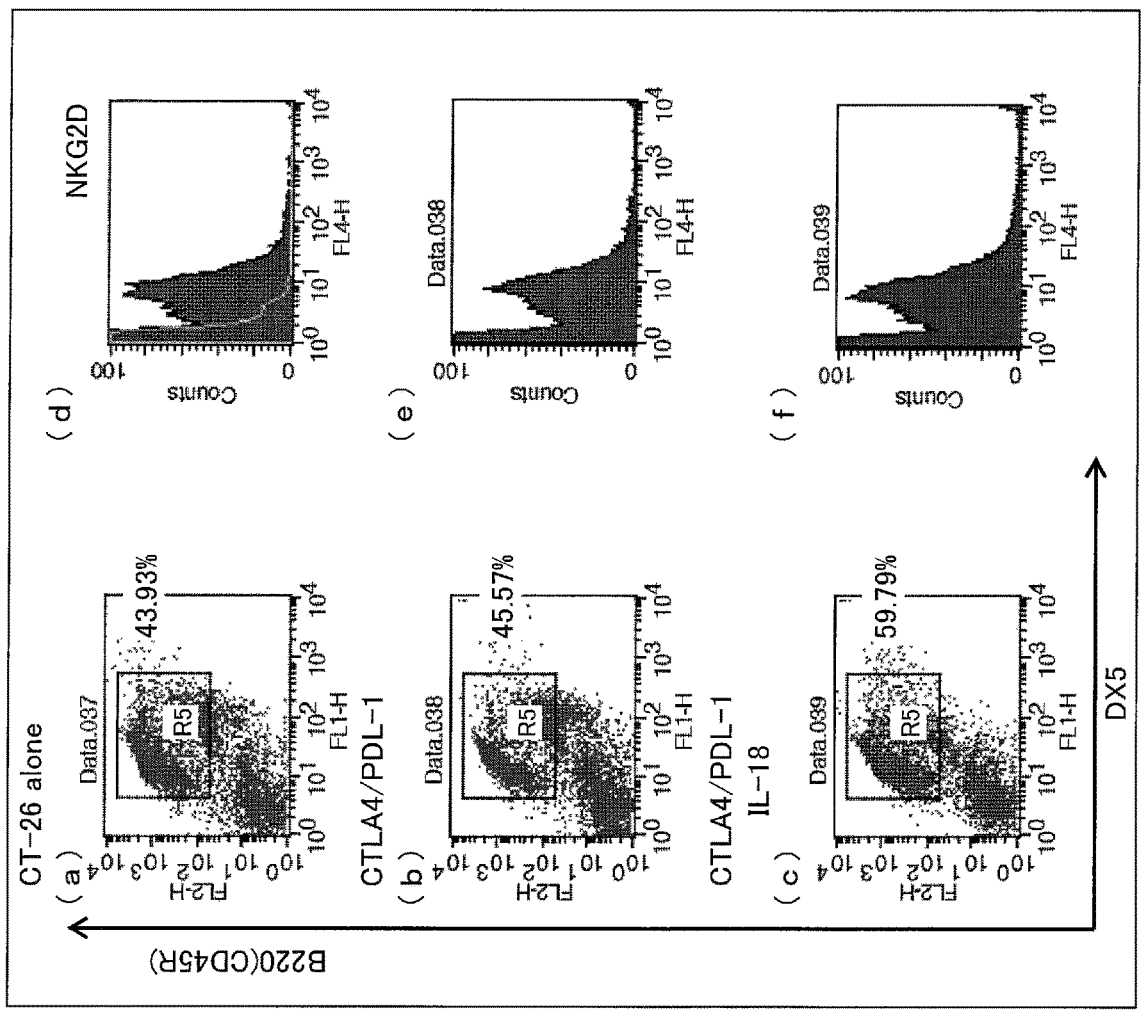
FIG. 10 is a set of graphs showing results of a study on expression intensities of B220 (CD45R), NKG2D, and DX5 (CD49b) on PECs induced by intraperitoneally administrating to the mice the following cancer therapeutic agents: the anti-CTLA-4 antibody and the anti-PD-L1 antibody; and the anti-CTLA-4 antibody, the anti-PD-L1 antibody, and IL-18. The horizontal axis of each of (a) to (c) of FIG. 10 indicates the expression intensity of DX5, whereas the vertical axis thereof indicates the expression intensity of B220 (CD45R). The horizontal axis of each of (d) to (f) indicates the expression intensity of NKG2D, whereas the vertical axis thereof indicates the number of cells. (a) and (d) each show data on a PEC as a control into which CT-26 cells were inoculated and which was then recovered without administration of a therapeutic agent. (b) and (e) each show data on a PEC for a case involving use of the anti-CTLA-4 antibody and the anti-PD-L1 antibody as therapeutic agents. (c) and (f) each show data on a PEC for a case involving use of the anti-CTLA-4 antibody, the anti-PD-L1 antibody, and IL-18 as therapeutic agents.

FIG. 10 is a set of graphs showing results of a study on expression intensities of surface markers B220 (CD45R), NKG2D, and DX5 (CD49b) on the PECs. In (a) to (c) of FIG. 10, horizontal axes represent expression intensities of DX5, while vertical axes represent expression intensities of B220 (CD45R).

(a) and (d) of FIG. 10 show data of PECs, as a control, collected from the mice inoculated with the CT-26 cells without having been administered with any therapeutic agents. (b) and (e) of FIG. 10 show data of PECs in the case of using, as a therapeutic agent, the anti-CTLA-4 antibody and the anti-PD-L1 antibody. (c) and (f) of FIG. 10 show data of PECs in the case of using, as a therapeutic agent, the anti-CTLA-4 antibody, the anti-PD-L1 antibody, and IL-18.

In (a) to (c) of FIG. 10, a region enclosed in a frame and represented by "R5" indicates PECs that are high in both DX5 expression intensity and B220 (CD45R) expression intensity. In the control ((a) of FIG. 10) administered with none of the therapeutic agents, the percentage of such PECs of all the cells was 43.93%. The percentage of such PECs collected 11 days after the day of administration of the anti-CTLA-4 antibody and the anti-PD-L1 antibody was 45.57% ((b) of FIG. 10), which is not very different from the percentage of the PECs in the control. In contrast, the percentage of such PECs collected 11 days after the day of administration of the anti-CTLA-4 antibody, the anti-PD-L1 antibody, and IL-18 was as high as 59.79% ((c) of FIG. 10).

In (d) to (f) of FIG. 10, horizontal axes represent expression intensities of NKG2D, while vertical axes represent cell counts. The relationship between the expression intensity of NKG2D and the cell count does not vary greatly in (d) to (f) of FIG. 10.

The above results revealed that the administration of the anti-CTLA-4 antibody, the anti-PD-L1 antibody, and IL-18 as a therapeutic agent enables the intraperitoneally induced active NK cells (cells that are high in both DX5 expression intensity and B220 (CD45R) expression intensity) to be maintained even after a long time period of 11 days has elapsed since the administration.

That is, it was revealed that the therapeutic agent according to an embodiment of the present invention enables enhancement and long-lasting presence of effector cells that attack and destroy tumor cells.

Example 10: Reduction of CD4-Positive, CD25-Positive T Cells

In Example 10, a study was conducted on changes in number of CD4-positive, CD25-positive T cells in the mice administered with the cancer therapeutic agent according to an embodiment of the present invention.

The suspension of the CT-26 cells in the same cell concentration ($5.0 \times 10^4$ cells per 0.25 ml) as that used in Example 1 was inoculated by intraperitoneal injection in an amount of 0.25 ml into each of the BALB/C wild-type mice. Then, therapeutic agents listed below were intraperitoneally injected 3 days after the day of the injection.

As therapeutic agents, the anti-PD-L1 antibody alone; IL-18 alone; the anti-PD-L1 antibody and IL-18; the anti-CTLA-4 antibody and the anti-PD-L1 antibody; and the anti-CTLA-4 antibody, the anti-PD-L1 antibody, and IL-18 were used. PECs collected 7 days after the day of the administration were analyzed. The doses are equal to those in Example 6.

Figure 11:
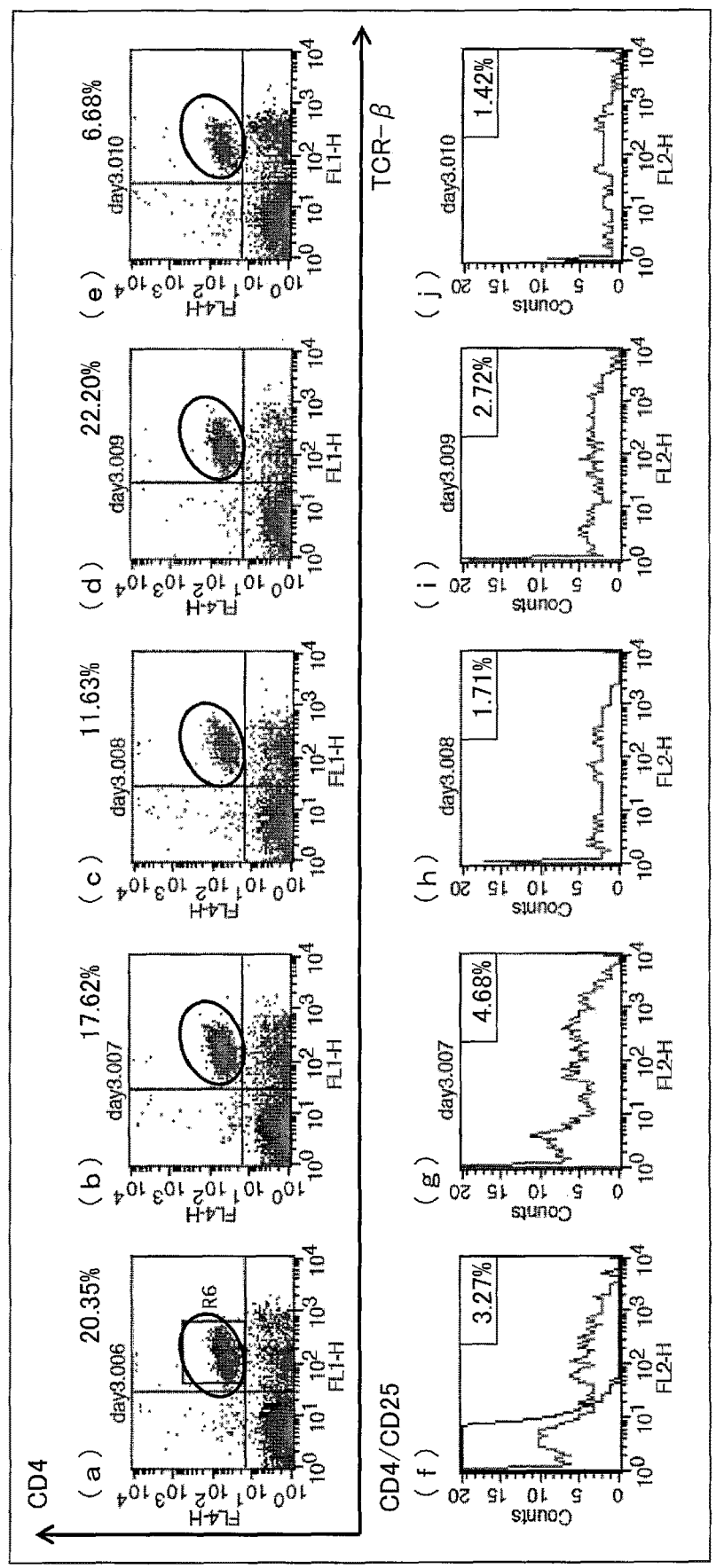
FIG. 11 is a set of graphs showing a confirmed result that the therapeutic agent according to an embodiment of the present invention reduces the number of CD4-positive, CD25-positive T cells. (a) and (f) each show the result of a case involving use of the anti-PD-L1 antibody as a therapeutic agent. (b) and (g) each show the result of a case involving use of IL-18 as a therapeutic agent. (c) and (h) each show the result of a case involving use of the anti-PD- L1 antibody and IL-18 as therapeutic agents. (d) and (i) each show the result of a case involving use of the anti-CTLA-4 antibody and the anti-PD-L1 antibody as therapeutic agents. (e) and (j) each show the result of a case involving use of the anti-CTLA-4 antibody, the anti-PD-L1 antibody, and IL-18 as therapeutic agents. (a) to (e) each show the result of determination of the percentage of CD4-positive T cells of all the PECs recovered in Example 10. The horizontal axis of each of (a) to (e) indicates the expression intensity of TCR-β (T cell receptor μ), whereas the vertical axis thereof indicates the expression intensity of CD4. (f) to (j) each show the result of detection of CD4-positive, CD25-positive T cells. The horizontal axis of each of (f) to (j) indicates the expression intensity of CD4-positive, CD25-positive T cells, whereas the vertical axis thereof indicates the number of CD4-positive, CD25-positive T cells.

FIG. 11 is a graph showing a confirmed result that the therapeutic agent according to an embodiment of the present invention reduces the number of CD4-positive, CD25-positive T cells.

(a) to (e) and (f) to (j) of FIG. 11 show results obtained in a case where the following therapeutic agents: the anti-PD-L1 antibody; IL-18; the anti-PD-L1 antibody and IL-18; the anti-CTLA-4 antibody and the anti-PD-L1 antibody; and the anti-CTLA-4 antibody, the anti-PD-L1 antibody, and IL-18 were individually used. (a) to (e) of FIG. 11 show results of determination of the percentage of CD4-positive T cells of all the PECs.

In (a) to (e), horizontal axes represent expression intensities of TCR-β (T cell receptor β), while vertical axes represent expression intensities of CD4. In (a) to (e) of FIG. 11, a region enclosed in a circle is a region where CD4-positive T cells are present. For example, the numeral "20.35%" in (a) of FIG. 11 is a percentage of CD4-positive T cells, of all the PECs, present in the region enclosed in the circle in (a) of FIG. 11.

(f) to (j) of FIG. 11 show results of detection of CD4-positive, CD25-positive T cells, wherein horizontal axes represent expression intensities of CD4-positive, CD25-positive T cells, while vertical axes represent cell counts of CD4-positive, CD25-positive T cells. Numeral values in (f) to (j) of FIG. 11 indicate percentages of CD4-positive, CD25-positive T cells of the CD4-positive T cells present in the regions enclosed in the circles in (a) to (e) of FIG. 11.

The CD4-positive T cells and CD25-positive T cells are regulatory lymphocytes (Tregs) that have a function to inhibit immune responses and inflammatory responses when cancer cells grow. In other words, increasing those cells would help the growth of cancer cells.

From (a) to (c) of FIG. 11, it can be seen that the use of the anti-PD-L1 antibody and IL-18 leads to fewer CD4-positive cells in comparison with the use of the anti-PD-L1 antibody alone and the use of IL-18 alone. Further, from (d) and (e) of FIG. 11, it can be seen that the use of the anti-CTLA-4 antibody, the anti-PD-L1 antibody, and IL-18 leads to fewer CD4-positive cells in comparison with the use of the anti-CTLA-4 antibody and the anti-PD-L1 antibody.

From (f) to (j) of FIG. 11, it can be seen that the use of the anti-PD-L1 antibody and IL-18 leads to a lower percentage of CD4-positive, CD25-positive T cells in comparison with the use of the anti-PD-L1 antibody alone and the use of IL-18 alone, and that the use of the anti-CTLA-4 antibody, the anti-PD-L1 antibody, and IL-18 leads to a lower percentage of CD4-positive, CD25-positive T cells in comparison with the use of the anti-CTLA-4 antibody and the anti-PD-L1 antibody.

From the above results, it can be seen that the cancer therapeutic agent according to an embodiment of the present invention further inhibits the growth of regulatory lymphocytes in comparison with the antibody (antibodies) used alone. This is presumed to occur because IL-18 used in combination further enhanced an inhibition effect of the antibody (antibodies) on the growth of regulatory lymphocytes.

Further, the cancer therapeutic agent according to an embodiment of the present invention enables promoting enhancement and growth of effector cells, as described earlier. Thus, it is presumed that since the cancer therapeutic agent according to an embodiment of the present invention enables inhibiting the growth of regulatory lymphocytes and promoting enhancement and growth of effector cells, the cancer therapeutic agent according to an embodiment of the present invention exerts a very high degree of antitumor effect.

Example 11: Importance of NK Cells on Antitumor Effect

In Example 11, a study on a roll that NK cells play in the antitumor effect of the cancer therapeutic agent according to an embodiment of the present invention was conducted by using the anti-asialo GM1 antibody, which is an antibody against NK cells.

50 µl of rabbit anti-asialo GM1 antibody or 50 µg of rabbit IgG was diluted to 250 µl with PBS, and a resulting diluent was intraperitoneally injected into mice on the day before inoculation of the CT-26 cells. The diluent of the rabbit anti-asialo GM1 antibody or rabbit IgG was intraperitoneally injected again in an amount of 250 µl 3 days after the day of the intraperitoneal injection. Thereafter, two additional intraperitoneal injections of the diluent in the amount of 250 µl were performed every 4 days. In other words, the intraperitoneal injections were performed on the day before the inoculation of the CT-26 cells and 2 days, 6 days, and 10 days after the inoculation of the CT-26 cells.

The mice were divided into the following groups: a control group to which 50 µg of rabbit IgG was to be administered as a therapeutic agent; and a group to which 100 µg of anti-CTLA-4 antibody, 100 µg of anti-PD-L1 antibody, and 2 µg of IL-18 was to be administered as a therapeutic agent. Each group was made up of five mice.

On the day after the first intraperitoneal injection of the anti-asialo GM1 antibody or rabbit IgG, the suspension of the CT-26 cells in the same cell concentration ($5.0 \times 10^4$ cells per 0.25 ml) as that used in Example 1 was intraperitoneally injected in an amount of 0.25 ml into each of the BALB/C wild-type mice. Then, intraperitoneal injection of each of the therapeutic agents was carried out four times in total. That is, a first intraperitoneal injection of each therapeutic agent was carried out 3 days after the day of the inoculation of the CT-26 cells. Thereafter, additional three intraperitoneal injections of each of the therapeutic agents were carried out every 4 days (i.e., 3 days, 7 days, 11 days, and 15 days after the day of the inoculation of the CT-26 cells).

Figure 12:
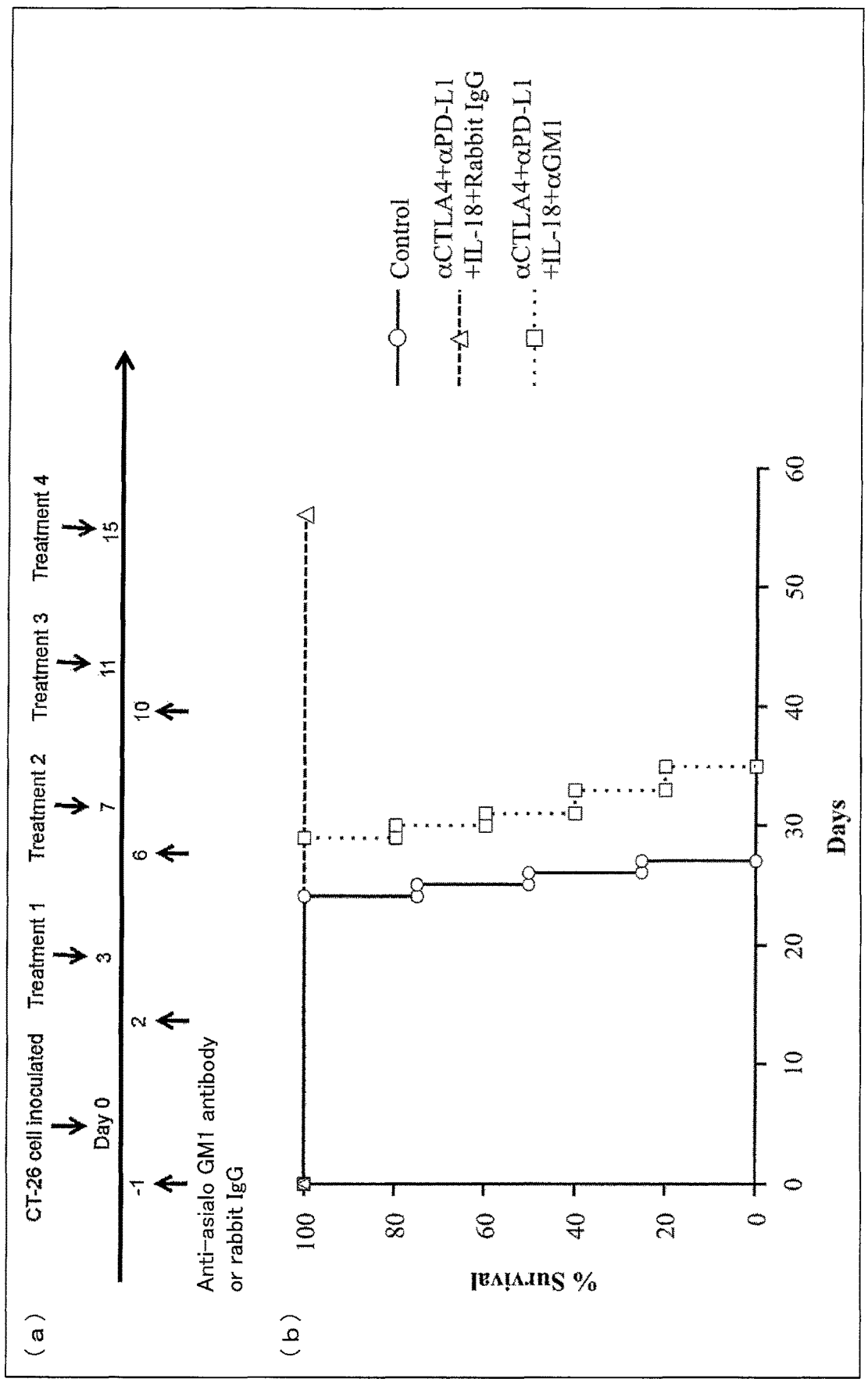
FIG. 12 is a view illustrating an influence of an anti-asialo GM1 antibody, which destroys and eliminates natural killer (NK) cells, on a survival rate of mice administered with the therapeutic agent according to an embodiment of the present invention. (a) illustrates schedules for administration of the rabbit anti-asialo GM1 antibody or rabbit IgG and for administration of the therapeutic agents. (b) shows the experimental results of Example 11.

FIG. 12 is a view illustrating an influence of the anti-asialo GM1 antibody, which destroys and eliminates natural killer (NK) cells, on a survival rate of the mice administered with the cancer therapeutic agent according to an embodiment of the present invention. (a) of FIG. 12 is a view illustrating schedules for administration of the aforementioned rabbit anti-asialo GM1 antibody or rabbit IgG and for administration of the therapeutic agents. (b) of FIG. 12 shows experimental results.

In (a) of FIG. 12, an upper row shows a schedule in which, assuming that the day of the inoculation of the CT-26 cells is the 0th day, the therapeutic agent is administered 3 days, 7 days, 11 days, and 15 days after the day of the inoculation of the CT-26 cells, as described above. In (a) of FIG. 12, a lower row shows a schedule in which, the rabbit anti-asialo GM1 antibody or rabbit IgG is administered on the day before the inoculation of the CT-26 cells and 2 days, 6 days, and 10 days after the inoculation of the CT-26 cells, as described above.

In (b) of FIG. 12, open circles indicate results for the control (to which rabbit IgG was administered on the day before the inoculation of the CT-26 cells and 2 days, 6 days, and 10 days after the inoculation of the CT-26 cells, and another rabbit IgG as a therapeutic agent was then administered in a manner as described above). Triangles indicate results for the group to which rabbit IgG was administered on the day before the inoculation of the CT-26 cells and 2 days, 6 days, and 10 days after the inoculation of the CT-26 cells, and the anti-CTLA-4 antibody, the anti-PD-L1 antibody, and IL-18 were then administered as a therapeutic agent in a manner as described above (hereinafter referred to as "group 1"). Squares indicate results of the group to which, instead of rabbit IgG, the anti-asialo GM1 antibody was administered in an experiment similar to the experiment by which the results indicated by the triangles were obtained (hereinafter referred to as "group 2"). In (b) of FIG. 12, a horizontal axis represents the number of days elapsed from the day of administration of the CT-26 cells, while a vertical axis represents a survival rate of the mice.

Like the mice shown in, for example, Example 4, all the mice in the group 1 survived even after the elapse of 60 days from the day of the inoculation of the CT-26 cells. The mice were in good health. In contrast, the mice in the group 2 shows a greater life prolongation effect than the control, but greatly falls behind the group 1 in terms of life prolongation effect although the anti-CTLA-4 antibody, the anti-PD-L1 antibody, IL-18 were used for the group 2. All the mice in the group 2 died within 35 days after the day of inoculation of the CT-26 cells.

As demonstrated in Example 8, the cancer therapeutic agent according to an embodiment of the present invention promotes intraperitoneal induction of active NK cells. This is presumed to occur because IL-18 promotes the induction caused by the antibodies. In contrast, for the group 2 administered with the anti-asialo GM1 antibody, the result shown in FIG. 12 was obtained because the anti-asialo GM1 antibody is presumed to reduce NK cells. Thus, it has been suggested that active NK cells induced by the antibodies and IL-18 play an important role on the antitumor effect resulting from the cancer therapeutic agent according to an embodiment of the present invention.

Example 12: Changes in Number of NK Cells of Mice Administered with Anti-Asialo GM1 Antibody In Example 12, PECs of mice administered with the anti-asialo GM1 antibody were analyzed by flow cytometry to study changes in number of NK cells.

Five mice each from the groups 1 and 2 in Example 11 were prepared. Administration of the anti-asialo GM1 antibody or rabbit IgG, inoculation of the CT-26 cells, and administration of a therapeutic agent were performed on the same schedule as in Example 11. Then, PECs were collected 4 days after the day of the administration of the therapeutic agent and were then subjected to flow cytometry.

Flow cytometry was carried out using the APC-labeled anti-CD45R/B220 antibody (manufactured by Biolegend, clone RA3-6B2) and the PE-labeled anti-CD49b antibody (manufactured by Beckton Dickinson, clone DX5) by the method provided above in (4) of [Experimental method].

Figure 13:
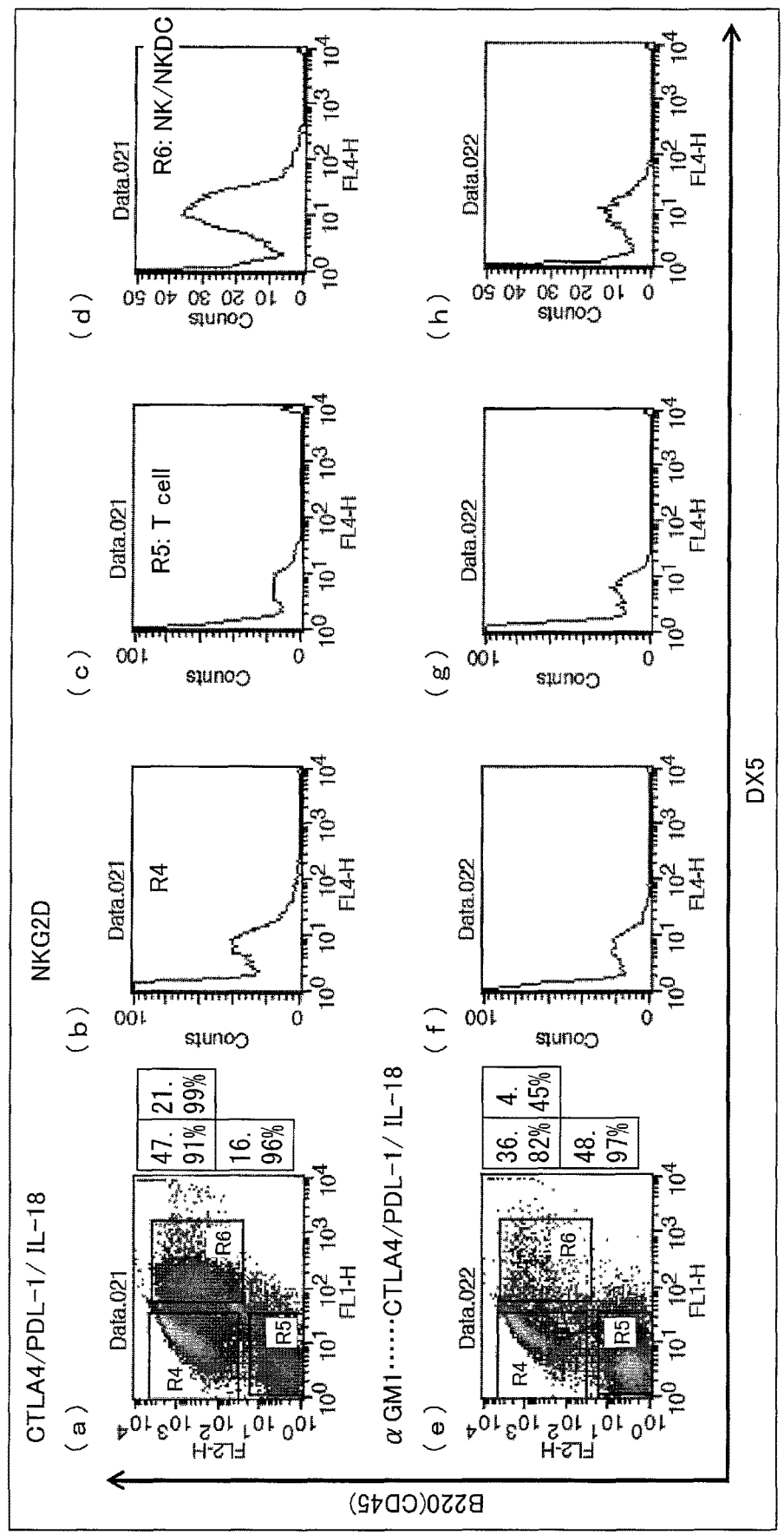
FIG. 13 is a view illustrating differences between results of analysis of PECs derived from mice to which the anti-asialo GM1 antibody was administered and PECs derived from mice to which the anti-asialo GM1 antibody was not administered. (a) to (d) show results of analysis of the PECs derived from the mice (group 1 in Example 11) to which the anti-asialo GM1 antibody was not administered. (e) to (h) show results of analysis of the PECs derived from the mice (group 2 in Example 11) to which the anti-asialo GM1 antibody was administered.

FIG. 13 is a view illustrating differences between results of analysis of the PECs derived from the mice to which the anti-asialo GM1 antibody was administered and the PECs derived from the mice to which the anti-asialo GM1 antibody was not administered. (a) to (d) of FIG. 13 show results of analysis of the PECs derived from the mice (the above group 1) to which the anti-asialo GM1 antibody was not administered. (e) to (h) of FIG. 13 show results of analysis of the PECs derived from the mice (the above group 2) to which the anti-asialo GM1 antibody was administered.

In (a) and (e) of FIG. 13, horizontal axes represent expression intensities of DX5, while vertical axes represent expression intensities of B220 (CD45). R4 represents cells on which NKG2D is expressed, R5 represents T cells, and R6 represents NK cells (including Pre-mMK).

In (a) of FIG. 13, R4 is 47.91%, R5 is 21.99%, and R6 is 16.96%. Further, in (e) of FIG. 13, R4 is 36.82%, R5 is 48.97%, and R6 is 4.45%.

(b) and (f) of FIG. 13 show the number of cells on which NKG2D is expressed, which cells are present in R4 in (a) and (e), respectively. (c) and (g) of FIG. 13 show the number of T cells which are present in R5 in (a) and (e), respectively. (d) and (h) of FIG. 13 show the number of NK cells (including Pre-mMK) which are present in R6 in (a) and (e), respectively.

From FIG. 13, it can be seen that, in the PECs derived from the group 2, the percentage of NK cells is significantly decreased, whereas the percentage of T cells is increased. The reduction of the NK cells is presumed to have led to the results shown in FIG. 12. That is, active NK cells induced by the antibodies and IL-18 are presumed to play an important role on the antitumor effect resulting from the cancer therapeutic agent according to an embodiment of the present invention.

Example 13: Changes of Expression of Cell Surface Markers Specific to NK Cells by Administration of Anti-Asialo GM1 Antibody In Example 13, PECs of mice administered with the anti-asialo GM1 antibody were analyzed by flow cytometry to study changes of expression of cell surface markers specific to NK cells.

As in Example 12, PECs were collected from the mice in the groups 1 and 2 and were then subjected to flow cytometry. Flow cytometry was carried out using the biotin-labeled anti-CD11c antibody (manufactured by Beckton Dickinson, clone HL3), a PE-labeled anti-NK1.1 antibody (manufactured by BD Bioscience, clone PK136), an APC-labeled anti-CD62L antibody (manufactured by BD Bioscience, clone MEL-14), a PE-labeled anti-CD69 antibody (manufactured by eBiocience, clone H1.2F3), and the PE-labeled anti-CD49b antibody (manufactured by Beckton Dickinson, clone DX5) by the method provided above in (4) of [Experimental method].

Figure 14:
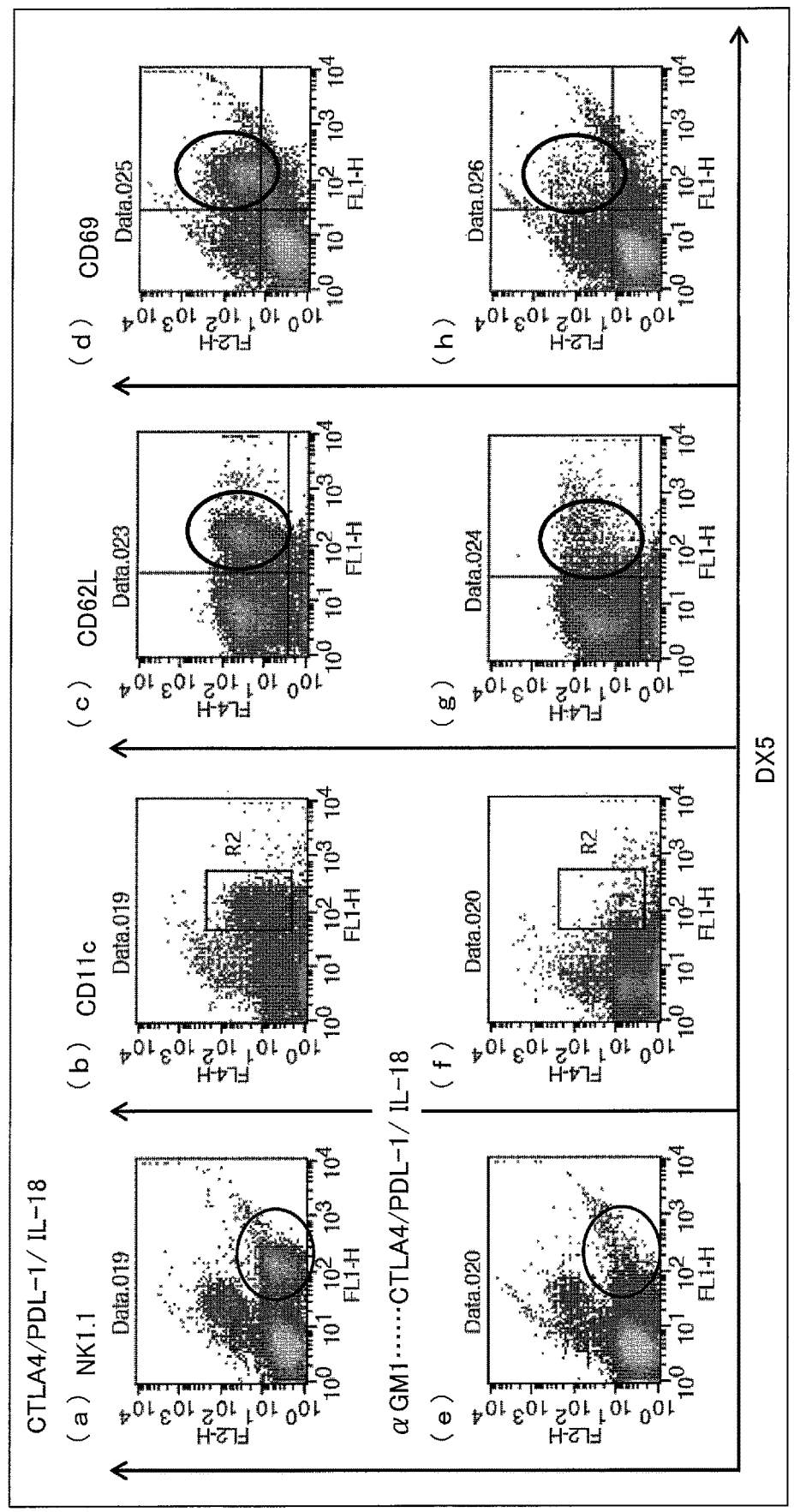
FIG. 14 is a view illustrating differences between results of surface marker analysis of the PECs derived from the mice to which the anti-asialo GM1 antibody was administered and the PECs derived from the mice to which the anti-asialo GM1 antibody was not administered. (a) to (d) show results of surface marker analysis of the PECs derived from the mice (group 1 in Example 11) to which the anti-asialo GM1 antibody was not administered. (e) to (h) show results of surface marker analysis of the PECs derived from the mice (group 2 in Example 11) to which the anti-asialo GM1 antibody was administered.

FIG. 14 is a view illustrating differences between results of surface marker analysis of the PECs derived from the mice to which the anti-asialo GM1 antibody was administered and the PECs derived from the mice to which the anti-asialo GM1 antibody was not administered. (a) to (d) of FIG. 14 show results of surface marker analysis of the PECs derived from the mice (the above group 1) to which the anti-asialo GM1 antibody was not administered. (e) to (h) of FIG. 14 show results of surface marker analysis of the PECs derived from the mice (the above group 2) to which the anti-asialo GM1 antibody was administered. Horizontal axes represent expression intensities of DX5, while vertical axes represent expression intensities of each surface marker.

NK1.1, CD11c, CD62L, and CD69 shown in FIG. 14 are all surface markers specific to NK cells (including Pre-mMK). From comparison of (a) to (d) of FIG. 14 and (e) to (h) of FIG. 14, it can be seen that fewer cells on which any of the above surface markers are expressed are present in the PECs derived from the group 2. Such reduction of the NK cells is presumed to have led to the results shown in FIG. 12. That is, active NK cells induced by the antibodies and IL-18 are presumed to play an important role on the antitumor effect resulting from the cancer therapeutic agent according to an embodiment of the present invention.

Example 14: Increase of CD4-Positive, CD25-Positive T Cells by Administration of Anti-Asialo GM1 Antibody In Example 14, PECs of mice administered with the anti-asialo GM1 antibody were analyzed by flow cytometry to study changes in number of CD4-positive, CD25-positive T cells.

As in Example 12, PECs were collected from the mice in the groups 1 and 2 and were then subjected to flow cytometry.

Flow cytometry was carried out using the FITC-labeled anti-CD4 antibody (manufactured by eBioscience, clone GK1.5), the APC-labeled anti-CD8 antibody (manufactured by Biolegend, clone 54-6.7), and a PE-labeled anti-CD25 antibody (manufactured by BD Bioscience, clone PC-61) by the method provided above in (4) of [Experimental method].

Figure 15:
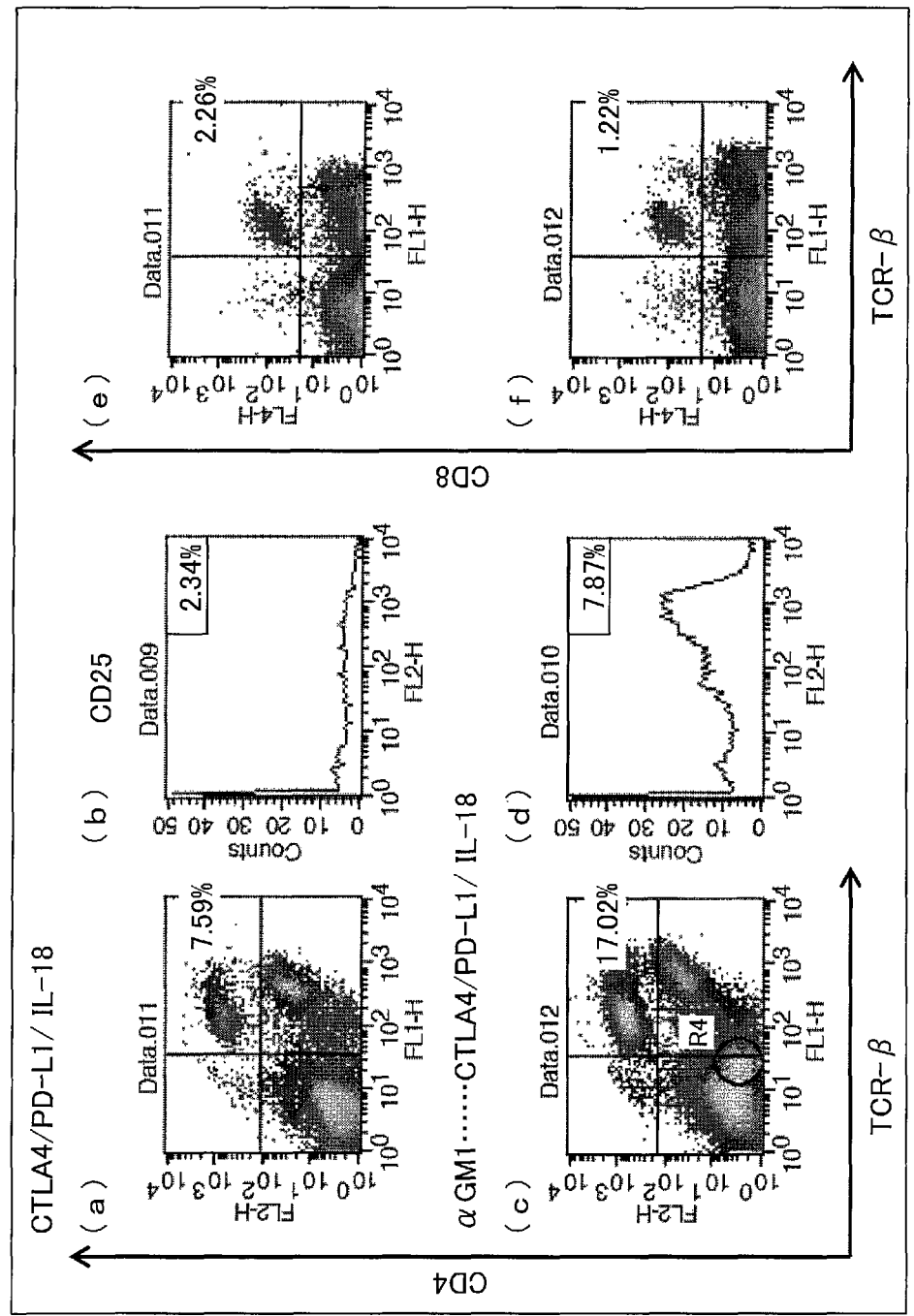
FIG. 15 is a view illustrating results of determination of (i) expression intensities of CD4-positive T cells and CD8-positive T cells and (ii) the number of CD25-positive T cells in the PECs derived from the mice to which the anti-asialo GM1 antibody was administered and the PECs derived from the mice to which the anti-asialo GM1 antibody was not administered. The horizontal axis of each of (a) and (c) indicates the expression intensity of TCR-β, whereas the vertical axis thereof indicates the expression intensity of CD4. The horizontal axis of each of (b) and (d) indicates the expression intensity of CD25, whereas the vertical axis thereof indicates the number of CD4-positive, CD25-positive T cells. The horizontal axis of each of (e) and (f) indicates the expression intensity of TCR-β, whereas the vertical axis thereof indicates the expression intensity of CD8. (a), (b), and (e) each show the result of the case of the administration of the anti-asialo GM1 antibody. (c), (d), and (f) each show the result of the case of no administration of the anti-asialo GM1 antibody.

FIG. 15 is a view illustrating results of determination of (i) expression intensities of CD4-positive T cells and CD8-positive T cells and (ii) the number of CD25-positive T cells in the PECs derived from the mice to which the anti-asialo GM1 antibody was administered and the PECs derived from the mice to which the anti-asialo GM1 antibody was not administered.

In (a) and (c) of FIG. 15, horizontal axes represent expression intensities of TCR-β, while vertical axes represent expression intensities of CD4. In (b) and (d) of FIG. 15, horizontal axes represent expression intensities of CD25, while vertical axes represent the number of CD4-positive, CD25-positive T cells. In (e) and (f) of FIG. 15, horizontal axes represent expression intensities of TCR-β, while vertical axes represent expression intensities of CD8.

The CD4-positive T cells and CD25-positive T cells are regulatory lymphocytes, as mentioned earlier. Increasing those cells would help the growth of cancer cells. In contrast, the CD8-positive T cells are cells that have an antitumor effect.

From comparison of (a) of FIG. 15 and (c) of FIG. 15, it can be seen that, in the case of the administration of the anti-asialo GM1 antibody, the percentage of CD4-positive T cells, of all the PECs, present in the upper right area in (a) and (c) of FIG. 15 was increased from 7.59% to 17.02%.

Further, comparison of (b) of FIG. 15 and (d) of FIG. 15 shows that the percentage of CD4-positive, CD25-positive cells of all the PECs was also significantly increased from 2.34% to 7.87%. In contrast, from comparison of (e) of FIG. 15 and (f) of FIG. 15, it can be seen that the percentage of CD8-positive T cells of all the PECs was decreased nearly one-half from 2.26% to 1.22%.

This result shows that even though the anti-CTLA-4 antibody, the anti-PD-L1 antibody, and IL-18 are administered to the mice to which the anti-asialo GM1 antibody has been administered previously, regulatory lymphocytes are increased and CD8-positive T cells are reduced. NK cells are known to activate CD8-positive T cells. Reduction of NK cells causes reduction of CD8-positive T cells.

Thus, the results in Example 15 suggest that the cancer therapeutic agent according to an embodiment of the present invention provides an excellent antitumor effect by activating NK cells, sustaining the NK cells as active NK cells for a long period of time, and activating CD8-positive T cells as a result.

Example 15: Therapeutic Effect on Retention of Ascites

In Example 15, a study was conducted on an effect of a cancer therapeutic agent according to an embodiment of the present invention on retention of ascites in mice inoculated with tumor cells.

A suspension of CT-26 cells ($5.0 \times 10^4$ cells per 0.25 ml) was intraperitoneally injected in an amount of 0.25 ml into each of the BALB/C wild-type mice. The mice were divided into the following groups: a control group to which 100 μg of rabbit IgG was to be administered as a therapeutic agent; a group to which 100 μg of anti-CTLA-4 antibody was to be administered as a therapeutic agent; and a group to which 100 μg of anti-CTLA-4 antibody and 2 μg of IL-18 were to be administered as a therapeutic agent. Each of the groups was made up of five mice. Intraperitoneal injection of each of the therapeutic agents was carried out four times in total. That is, a first intraperitoneal injection of each of the therapeutic agents was carried out 3 days after the day of the inoculation of the CT-26 cells. Thereafter, additional three intraperitoneal injections of each of the therapeutic agents were carried out every 4 days. Then, 21 days after the day of inoculation of the CT-26 cells, a therapeutic effect on retention of ascites was studied.

Figure 16:
FIG. 16 is an external view photograph showing whether, 21 days after the day of inoculation of the CT-26 cells, ascites is present or absent in the control or in the mice in the groups administered with the therapeutic agents.

FIG. 16 is an external view photograph showing whether, 21 days after the day of inoculation of the CT-26 cells, ascites is present or absent in the mice in each of the above groups.

Figure 17:
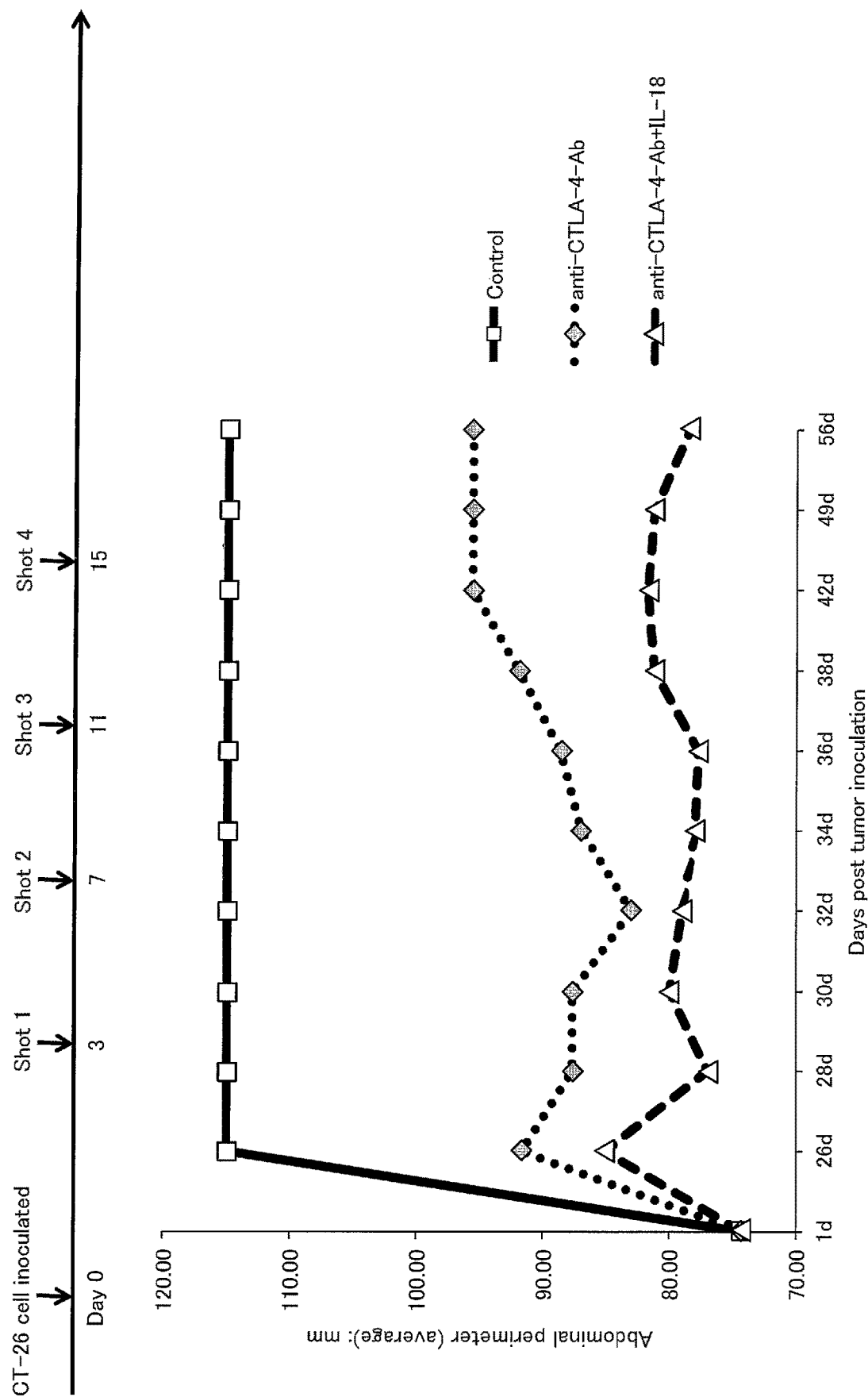
FIG. 17 is a graph showing changes in abdominal circumference of the mice in the control or in the groups administered with the therapeutic agents.

FIG. 17 is a graph showing changes in abdominal circumference of the mice in each of the groups. A horizontal axis represents the number of days elapsed from the day of inoculation of the CT-26 cells, while a vertical axis represents an abdominal circumference (mm). The abdominal circumferences of the mice making up each of the groups were measured, and an average value thereof was calculated for each of the groups.

As shown in FIG. 17, the abdominal circumference of the control was remarkably increased with retention of ascites and reached 115 mm 26 days after the inoculation of the CT-cells. Thereafter, the abdominal circumference was maintained at 115 mm. In contrast, the abdominal circumference of the mice administered with the anti-CTLA-4 antibody and IL-18 remained at a level as low as about 80 mm and little changed from the abdominal circumference on the first day after the inoculation of the CT-26 cells, even on the 56th day after the inoculation. Moreover, the abdominal circumference of the mice administered with the anti-CTLA-4 antibody and IL-18 was greatly diminished in comparison with the mice administered with the anti-CTLA-4 antibody alone, and retention of ascites was not observed.

Figure 18:
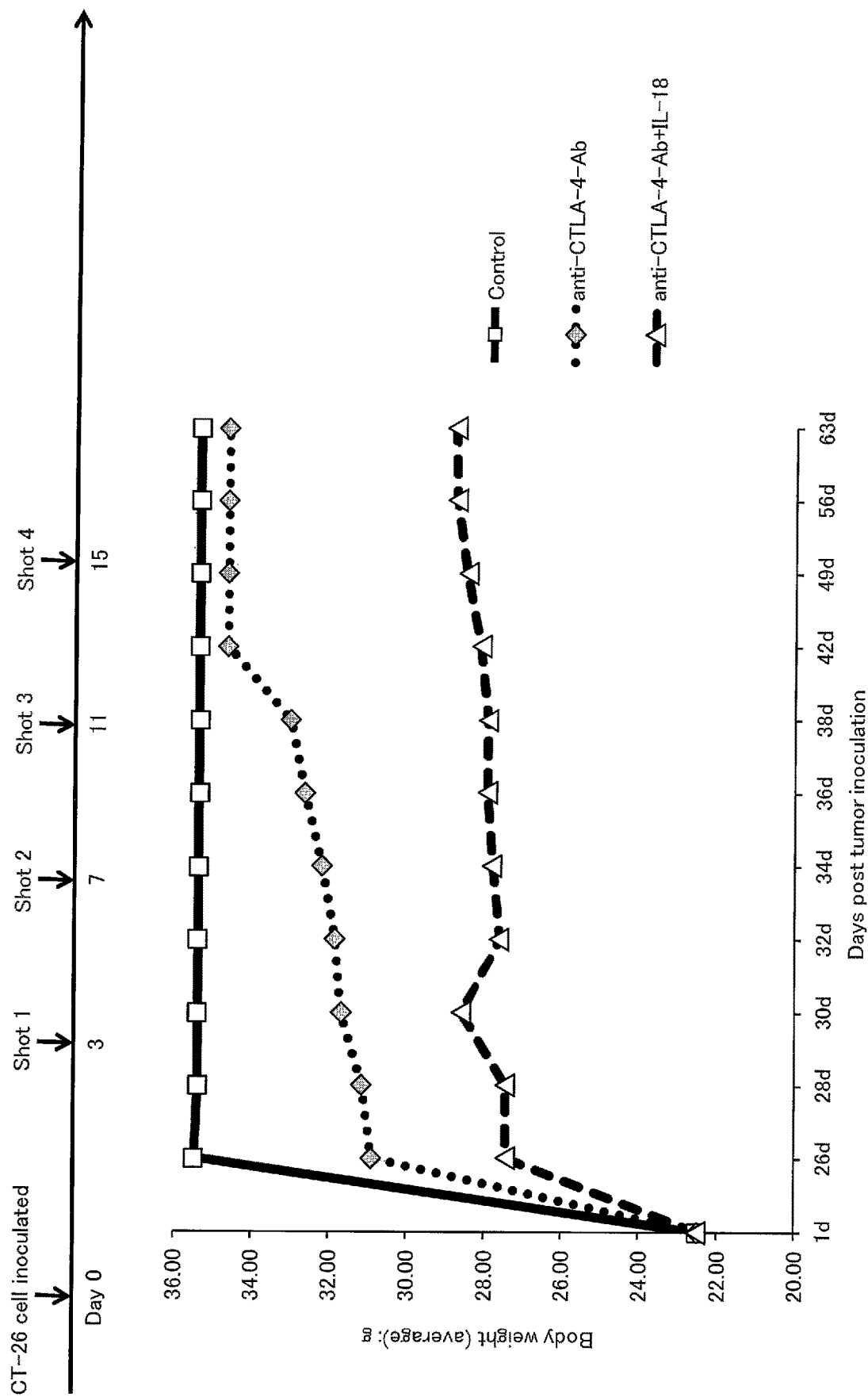
FIG. 18 is a graph showing changes in body weight of the mice in the control or in the groups administered with the therapeutic agents.

FIG. 18 is a graph showing changes in body weight of the mice in each of the groups. A horizontal axis is the same as that in FIG. 17, while a vertical axis represents a body weight (g). Body weights of the mice making up each of the groups were measured, and an average value thereof was calculated for each of the groups.

The control group showed remarkable increase in body weight caused by retained ascites. Similarly, the body weight of the mice administered with the anti-CTLA-4 antibody alone was increased to a body weight which does not greatly differ from that of the control, on the 42th and later days after the inoculation of CT-26 cells.

In contrast, in the mice administered with the anti-CTLA-4 antibody and IL-18, retention of ascites was not observed. As is apparent from FIG. 18, the body weight was held down and was maintained at a low level.

Figure 19:
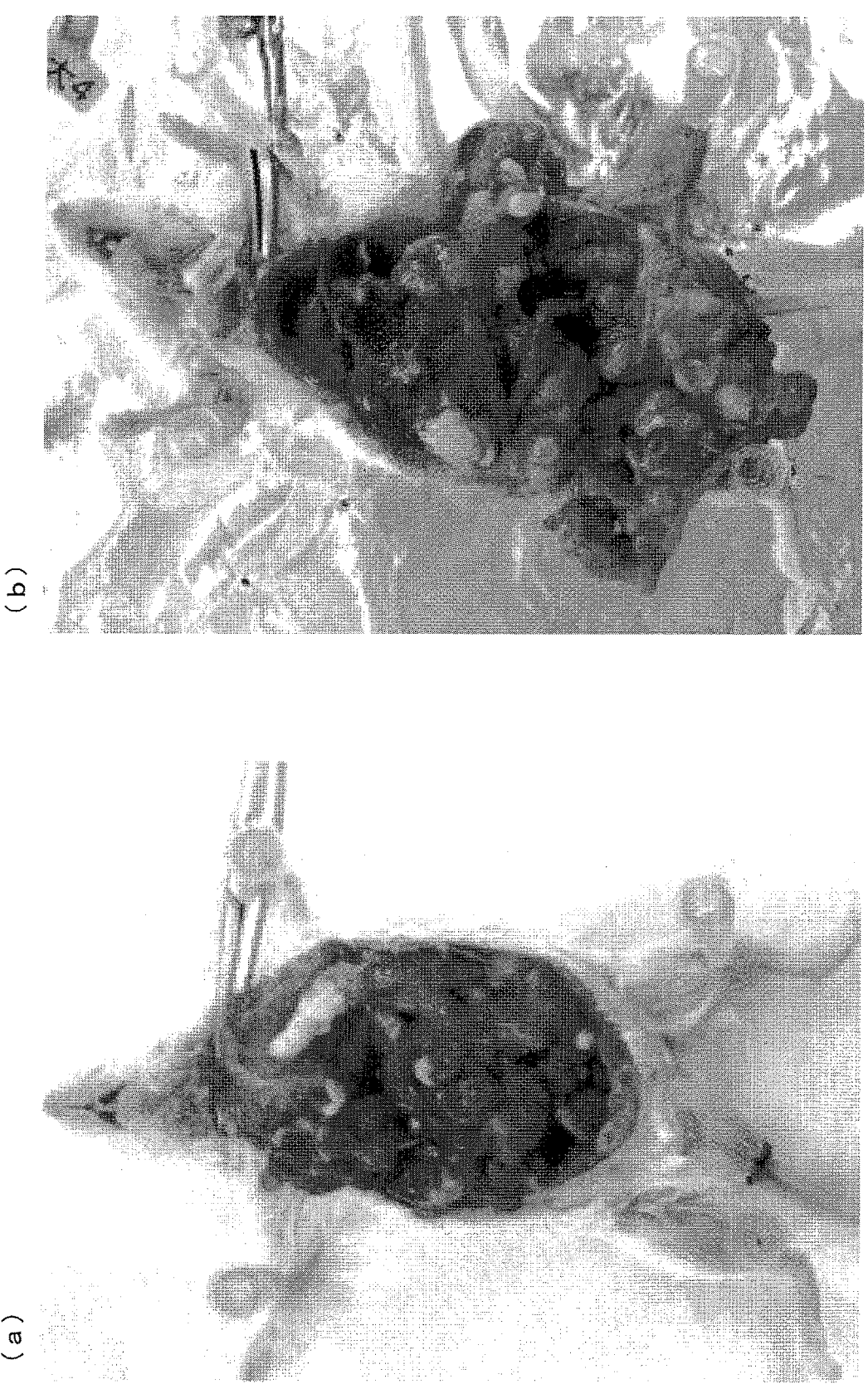
FIG. 19 is a view showing states of abdominal cavities, 21 days after the day of inoculation of the CT-26 cells, of the control and the mouse administered with the anti-CTLA-4 antibody. (a) shows the result of a control. (b) shows the result for a mouse administered the anti-CTLA-4 antibody.

FIG. 19 is a view showing states of abdominal cavities, 21 days after the day of inoculation of the CT-26 cells, of the control ((a) of FIG. 19) and the mouse administered with the anti-CTLA-4 antibody ((b) of FIG. 19). As shown in FIG. 19, many tumor masses and adhesion of organs were found in both of them.

Figure 20:
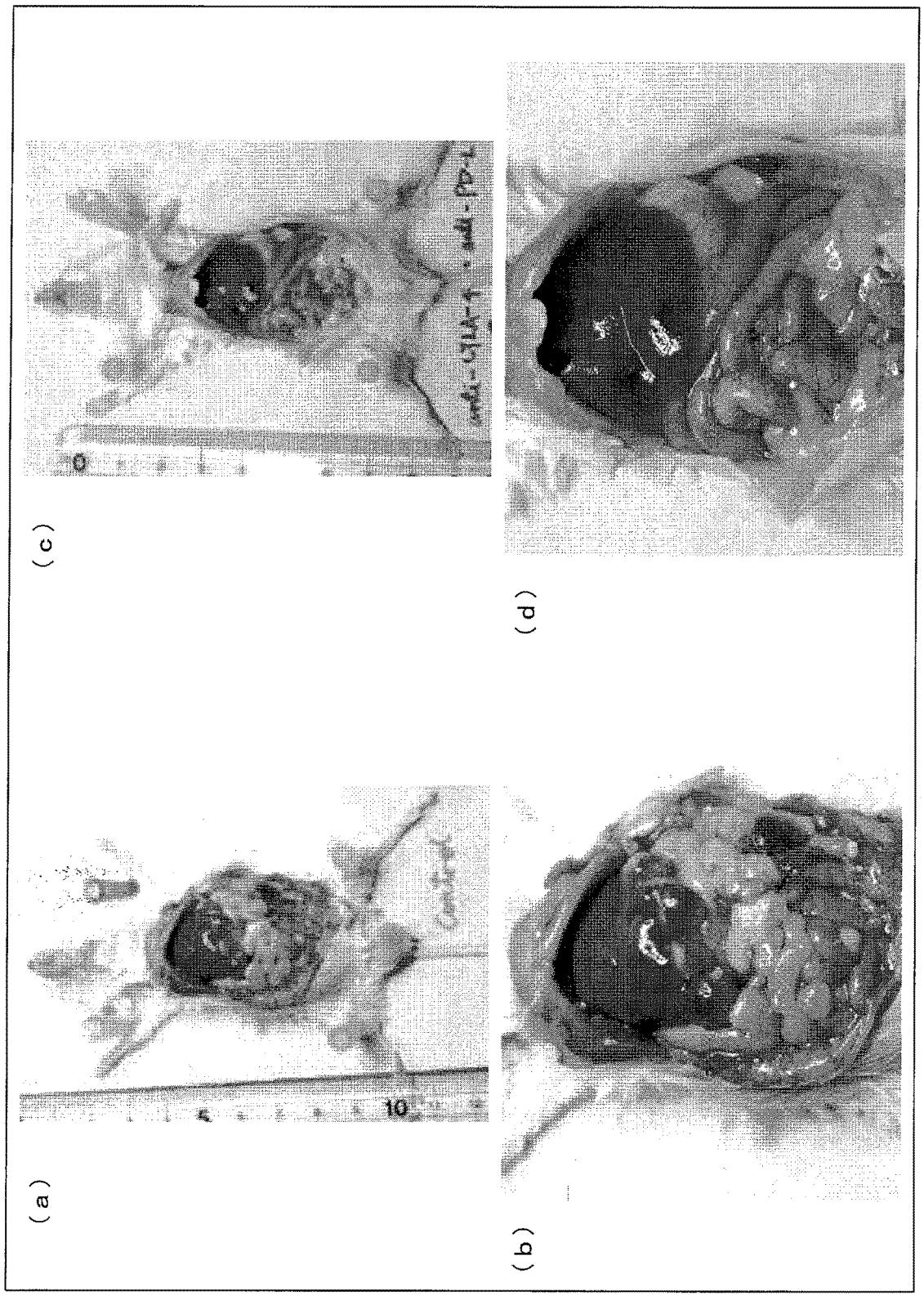
FIG. 20 is a view showing states of abdominal cavities, 21 days after the day of inoculation of CT-26 cells, of the control and the mouse administered with the anti-CTLA-4 antibody, the anti-PD-L1 antibody, and IL-18. (a) shows the result of a control. (b) is an enlarged view of (a). (c) shows the result for a mouse administered the anti-CTLA-4 antibody, the anti-PD-L1 antibody, and IL-18. (d) is an enlarged view of (c).

FIG. 20 is a view showing states of abdominal cavities, 21 days after the day of inoculation of CT-26 cells, of the control ((a) of FIG. 20 and (b) of FIG. 20, which is an enlarged view thereof) and the mouse administered with the anti-CTLA-4 antibody, the anti-PD-L1 antibody, and IL-18 ((c) of FIG. 20 and (d) of FIG. 20, which is an enlarged view thereof). In the mouse administered with the anti-CTLA-4 antibody, the anti-PD-L1 antibody, and IL-18, neither tumor masses nor adhesion of organs was found. Moreover, their organs were kept in very good states.

Figure 21:
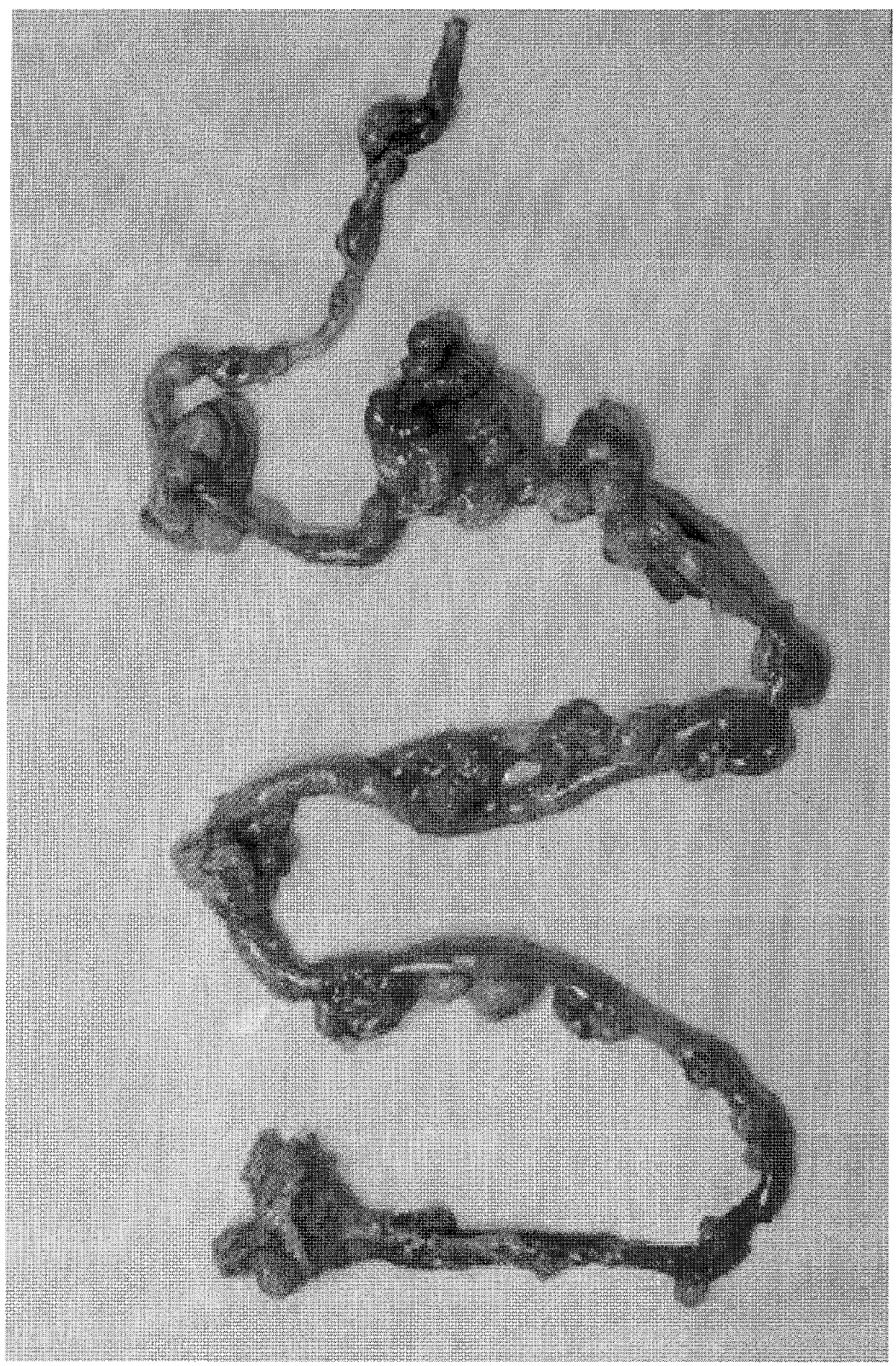
FIG. 21 is a view showing external appearance of small intestine of the mouse in the control 21 days after the day of inoculation of CT-26 cells.
Figure 22:
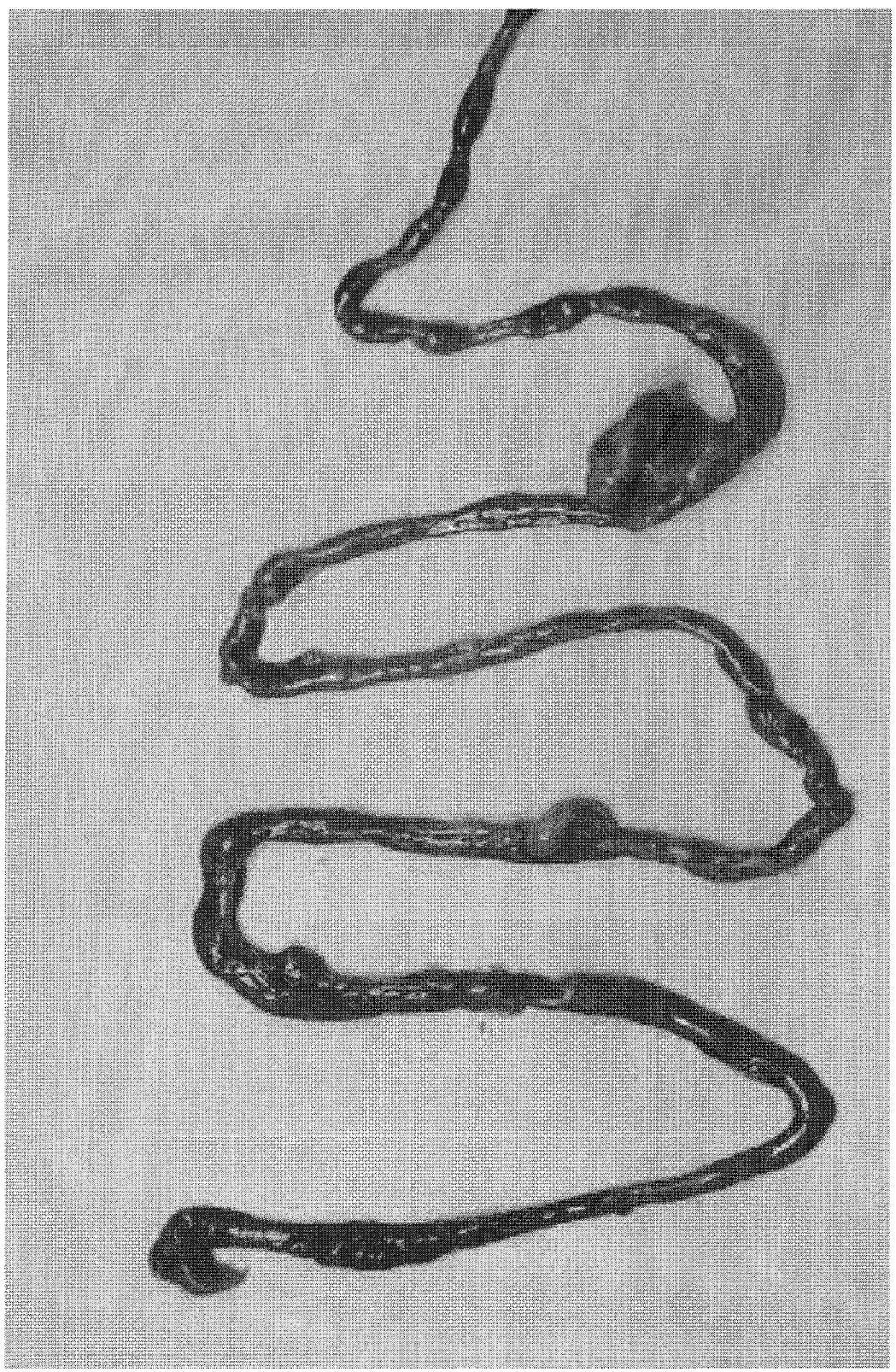
FIG. 22 is a view showing external appearance of small intestine, 21 days after the day of inoculation of CT-26 cells, of the mouse administered with the anti-CTLA-4 antibody, the anti-PD-L1 antibody, and IL-18.

FIG. 21 is a view showing external appearance of small intestine of the control 21 days after the day of inoculation of CT-26 cells. FIG. 22 is a view showing external appearance of small intestine, 21 days after the day of inoculation of CT-26 cells, of the mouse administered with the anti-CTLA-4 antibody, the anti-PD-L1 antibody, and IL-18. As is apparent from comparison between both of them, many tumor masses were formed in the control, whereas almost no tumor masses were observed in the mouse administered with the anti-CTLA-4 antibody, the anti-PD-L1 antibody, and IL-18.

Figure 23:
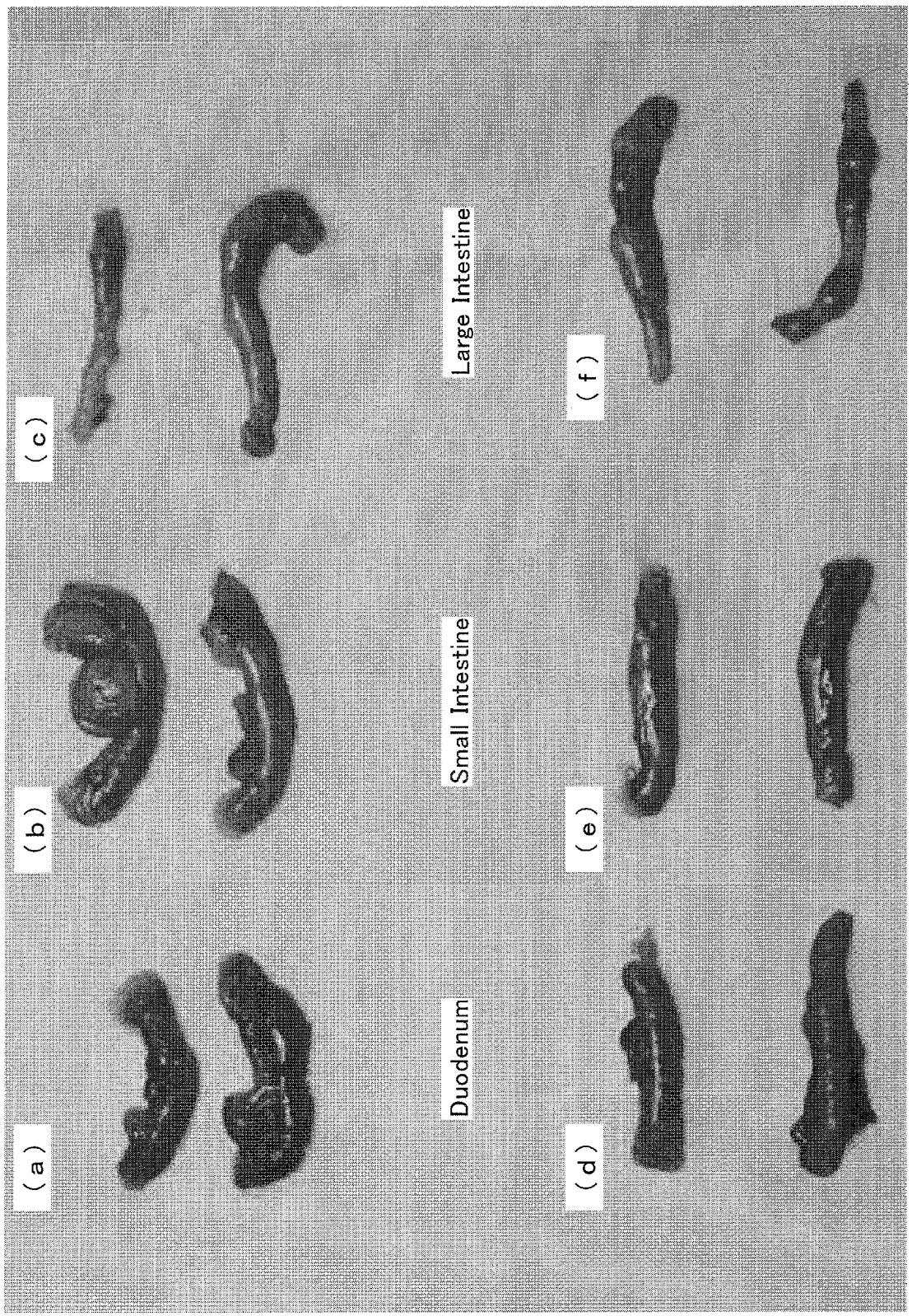
FIG. 23 is a view showing external appearances of parts of duodenums, parts of small intestines, and parts of large intestines, 21 days after the day of inoculation of CT-26 cells, of the control and the mouse administered with the anti-CTLA-4 antibody, the anti-PD-L1 antibody, and IL-18. (a) to (c) each show the result of a control. (d) to (f) each show the result for a mouse administered with the anti-CTLA-4 antibody, the anti-PD-L1 antibody, and IL-18. (a) and (d) each show duodenums 21 days after the day of inoculation of CT-26 cells. (b) and (e) each show small intestines 21 days after the day of inoculation of CT-26 cells. (c) and (f) each show large intestines 21 days after the day of inoculation of CT-26 cells.

FIG. 23 is a view showing external appearances of parts of duodenums ((a) and (d) of FIG. 23), parts of small intestines ((b) and (e) of FIG. 23), and parts of large intestines ((c) and (f) of FIG. 23), 21 days after the day of inoculation of CT-26 cells, of the control ((a) to (c) of FIG. 23) and the mouse administered with the anti-CTLA-4 antibody, the anti-PD-L1 antibody, and IL-18 ((d) to (f) of FIG. 23).

From FIG. 23, the large intestine of the control was not greatly different from that of the mouse administered with the anti-CTLA-4 antibody, the anti-PD-L1 antibody, and IL-18. However, the duodenum and small intestine were kept nicely in the mouse administered with the anti-CTLA-4 antibody, the anti-PD-L1 antibody, and IL-18, while the duodenum and small intestine of the control had tumor masses.

As shown in (c) and (d) of FIG. 20, FIG. 22, and (d) to (f) of FIG. 23, stronger autoimmune-like lesions were not appeared in the intestines and other organs. Further, the mouse administered with the anti-CTLA-4 antibody and/or the anti-PD-L1 antibody, and IL-18 was in good health as far as it was observed, and did not show body weight loss or other symptom.

From the above results, it can be seen that the use of the anti-CTLA-4 antibody, the anti-PD-L1 antibody, and IL-18 sufficiently inhibits peritoneal dissemination caused by inoculation of CT-26 cells, which are murine large intestine cancer cells. It is known that cancers such as gastric cancer, large intestine cancer, ovarian cancer, osteosarcoma, and leukemia develop peritoneal metastasis which is difficult to treat. Since the cancer therapeutic agent according to an embodiment of the present invention enables effectively inhibiting peritoneal metastasis, it can be said that the cancer therapeutic agent according to an embodiment of the present invention is a therapeutic agent that is very effective in treating those cancers.

Example 16: Study on Adverse Reactions Caused by Cancer Therapeutic Agent According to Embodiment of Present Invention In Example 15, neither strong autoimmune-like lesions nor body weight loss or any other symptoms were found in the mice administered with the cancer therapeutic agent according to an embodiment of the present invention. This suggested that the cancer therapeutic agent according to an embodiment of the present invention reduced adverse reactions. In view of this, in Example 16, a more detailed study was conducted on adverse reactions caused by the cancer therapeutic agent according to an embodiment of the present invention. Specifically, a study was conducted on the possibility that IL-18 may aggravate adverse reactions caused by the antibody (antibodies) which serve as active ingredients of the cancer therapeutic agent.

As in Example 1, a suspension of CT-26 cells (in a cell concentration of $5.0 \times 10^4$ cells per 0.25 ml) was inoculated by intraperitoneal injection in an amount of 0.25 ml into each of the BALB/C wild-type mice.

The mice were divided into the following groups: a control group to which 0.25 ml of PBS was to be administered as a therapeutic agent (group 1); a group to which 100 μg of anti-CTLA-4 antibody and 200 μg of anti-PD-L1 antibody were to be administered as a therapeutic agent (group 2); a group to which 100 μg of anti-CTLA-4 antibody, 200 μg of anti-PD-L1 antibody, and IL-18 (2 μg) were to be administered as a therapeutic agent (group 3); and a group to which 100 μg of anti-CTLA-4 antibody, 200 μg of anti-PD-L1 antibody, and IL-18 (100 μg) were to be administered as a therapeutic agent (group 4). Each of the groups was made up of five mice. It should be noted that each of the doses (μg) of the PBS, the anti-CTLA-4 antibody, the anti-PD-L1 antibody, and IL-18 is a dose per 25 g of a body weight of a mouse.

Every 4 days from 3 days after the day of injection of the CT-26 cells, each of the therapeutic agents was intraperitoneally injected into the mice four times in total. Blood and tissue samples were collected 18 days after the day of injection of the CT-26 cells, and were inspected not only for liver function and renal function but also for lesions in the tissues such as intestines, liver, and kidney. The experiment was repeated three times.

Figure 24:
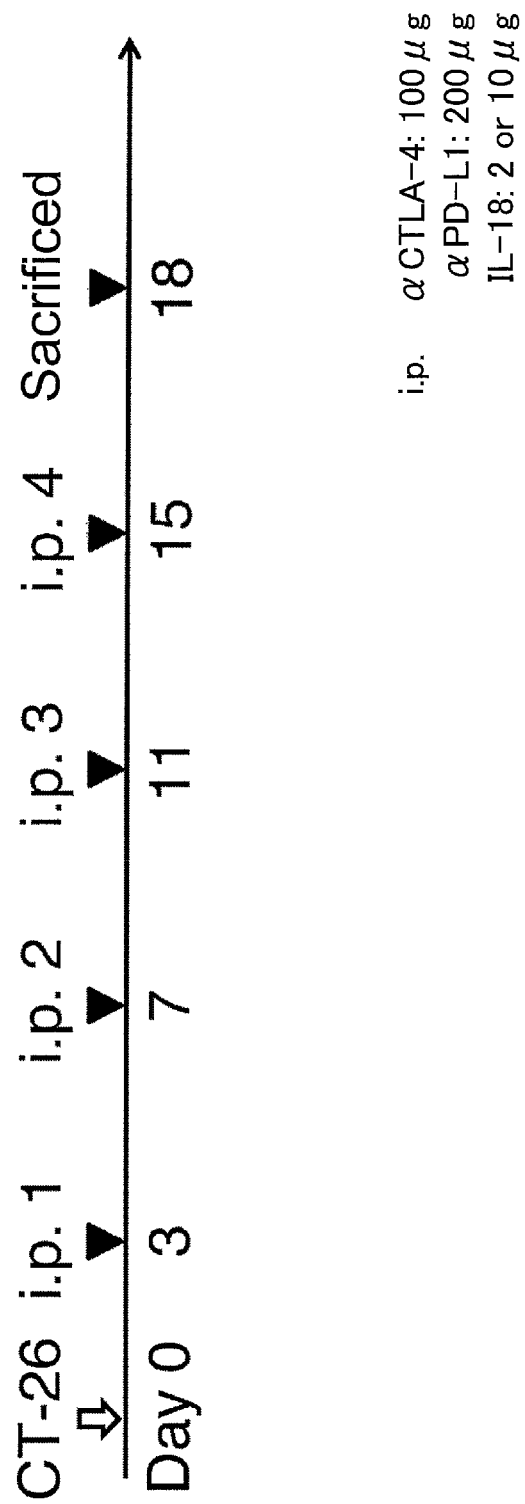
FIG. 24 is a view illustrating schedules for inoculation of the CT-26 cells and for administration of each of the therapeutic agents in Example 16.

FIG. 24 is a view illustrating schedules for the aforementioned inoculation of the CT-26 cells and for the administration of each of the therapeutic agents, and illustrating that each of the therapeutic agents was intraperitoneally administered 3 days, 7 days, 11 days, and 15 days after "Day 0", which is the day of inoculation of the CT-26 cells, and the mice were sacrificed 18 days after "Day 0".

Figure 25:
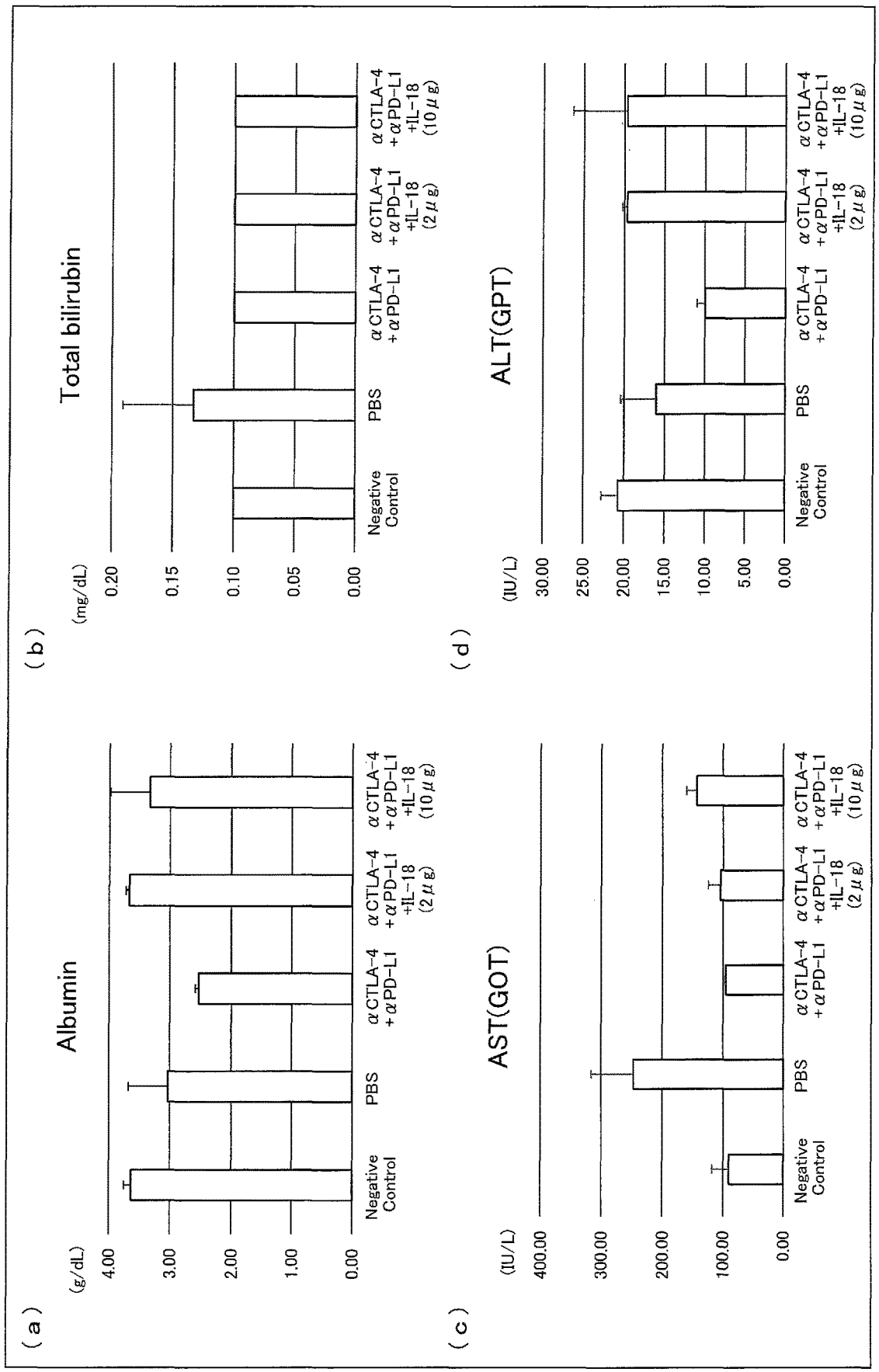
FIG. 25 is a set of graphs showing results of measurements of albumin concentration in blood ((a) of FIG. 25), total bilirubin concentration in blood ((b) of FIG. 25), AST (GOT) concentration in blood ((c) of FIG. 25), and ALT (GPT) concentration in blood ((d) of FIG. 25) in Example 16.
Figure 26:
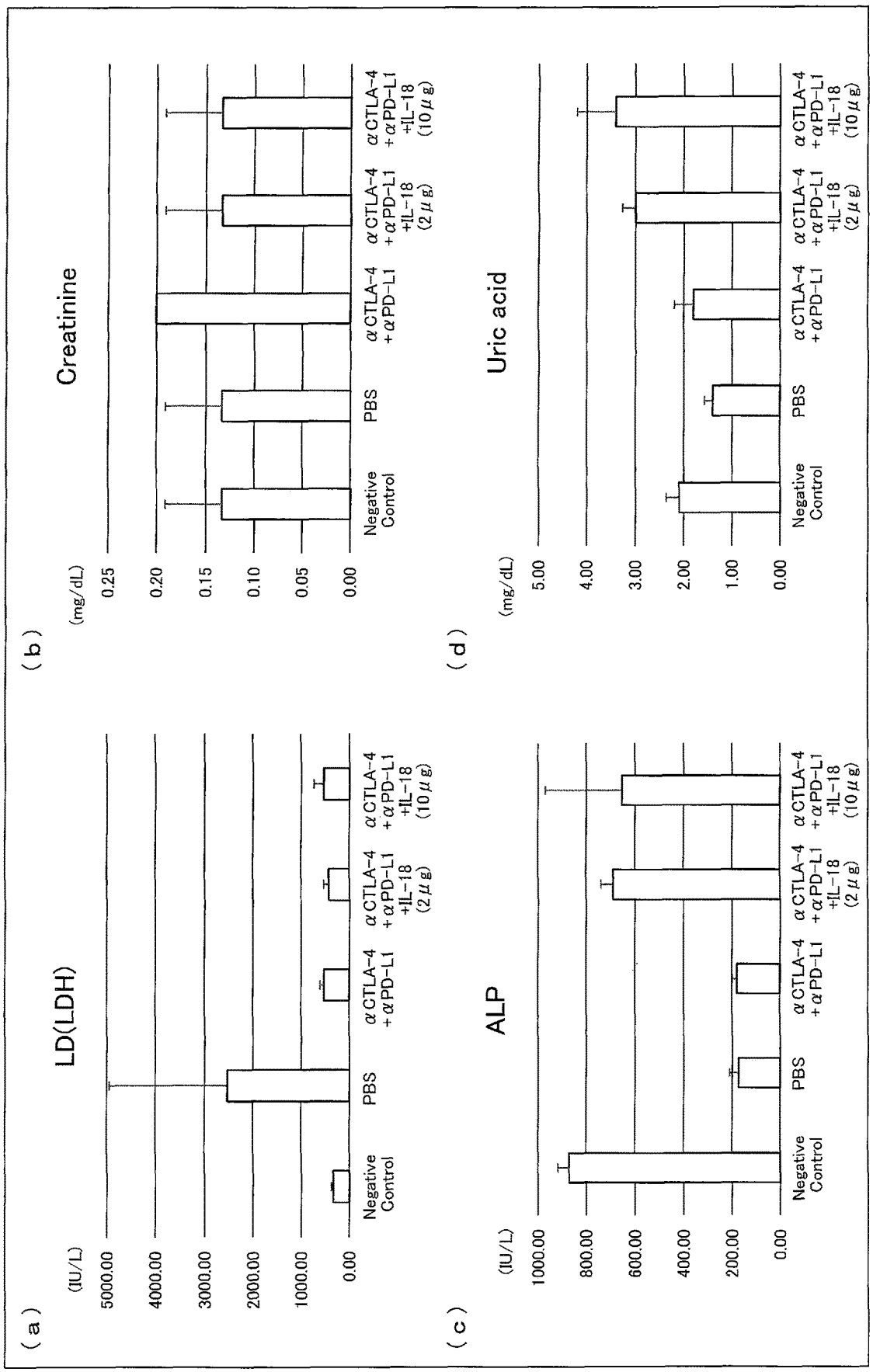
FIG. 26 is a set of graphs showing results of measurements of LD (LDH) concentration in blood ((a) of FIG. 26), creatinine concentration in blood ((b) of FIG. 26), ALP concentration in blood ((c) of FIG. 26), and uric acid concentration in blood (FIG. 26 of (d)) in Example 16.
Figure 27:
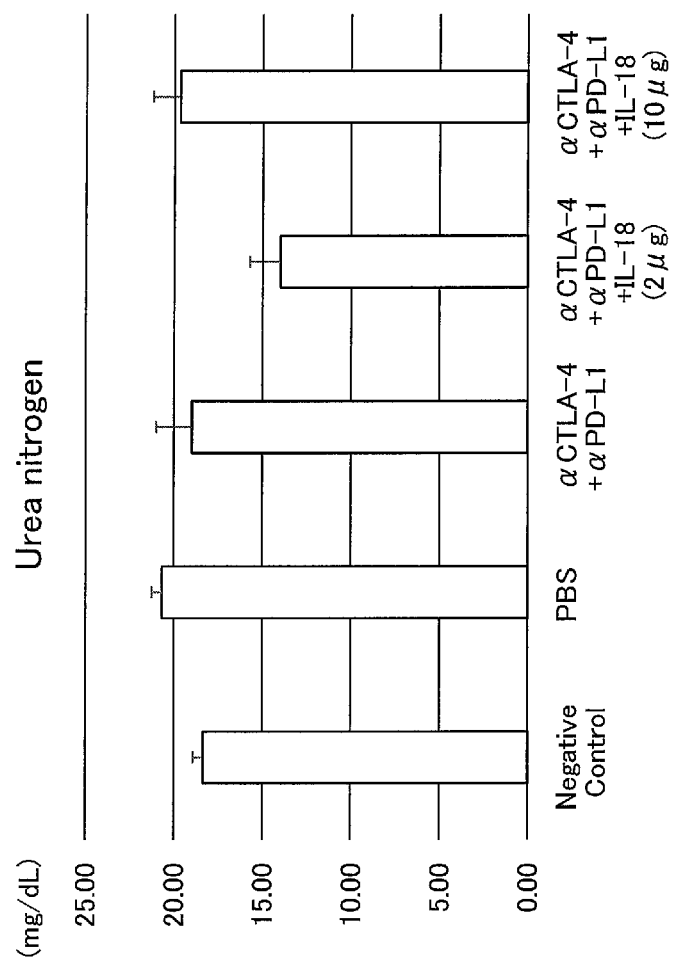
FIG. 27 is a graph showing results of measurement of urea nitrogen concentration in blood in Example 16.

FIG. 25 is a set of graphs showing results of measurements of albumin concentration in the blood ((a) of FIG. 25), total bilirubin concentration in the blood ((b) of FIG. 25), AST (GOT) concentration in the blood ((c) of FIG. 25), and ALT (GPT) concentration in the blood ((d) of FIG. 25). FIG. 26 is a set of graphs showing results of measurements of LD (LDH) concentration in the blood ((a) of FIG. 26), creatinine concentration in the blood ((b) of FIG. 26), ALP concentration in the blood ((c) of FIG. 26), and uric acid concentration in the blood (FIG. 26 of (d)). FIG. 27 is a graph showing results of measurement of urea nitrogen concentration in the blood. It should be noted that the results for "Negative Control" in FIGS. 25, 26, and 27 are results obtained by using blood of healthy mice which were neither inoculated with the CT-26 cells nor administered with the therapeutic agents (hereinafter referred to as "healthy control group").

As shown by "αCTLA-4+αPD-L1" in (a) of FIG. 25, the blood albumin concentration in the group 2, which had been administered with 100 μg of anti-CTLA-4 antibody and 200 μg of anti-PD-L1 antibody, was significantly low in comparison with that in the healthy control group. (a) to (d) of FIG. 28 are views showing results of tissue staining of livers of the mice in the groups 1 to 4 with hematoxylin eosin (HE) at a 200-fold magnification.

Figure 28:
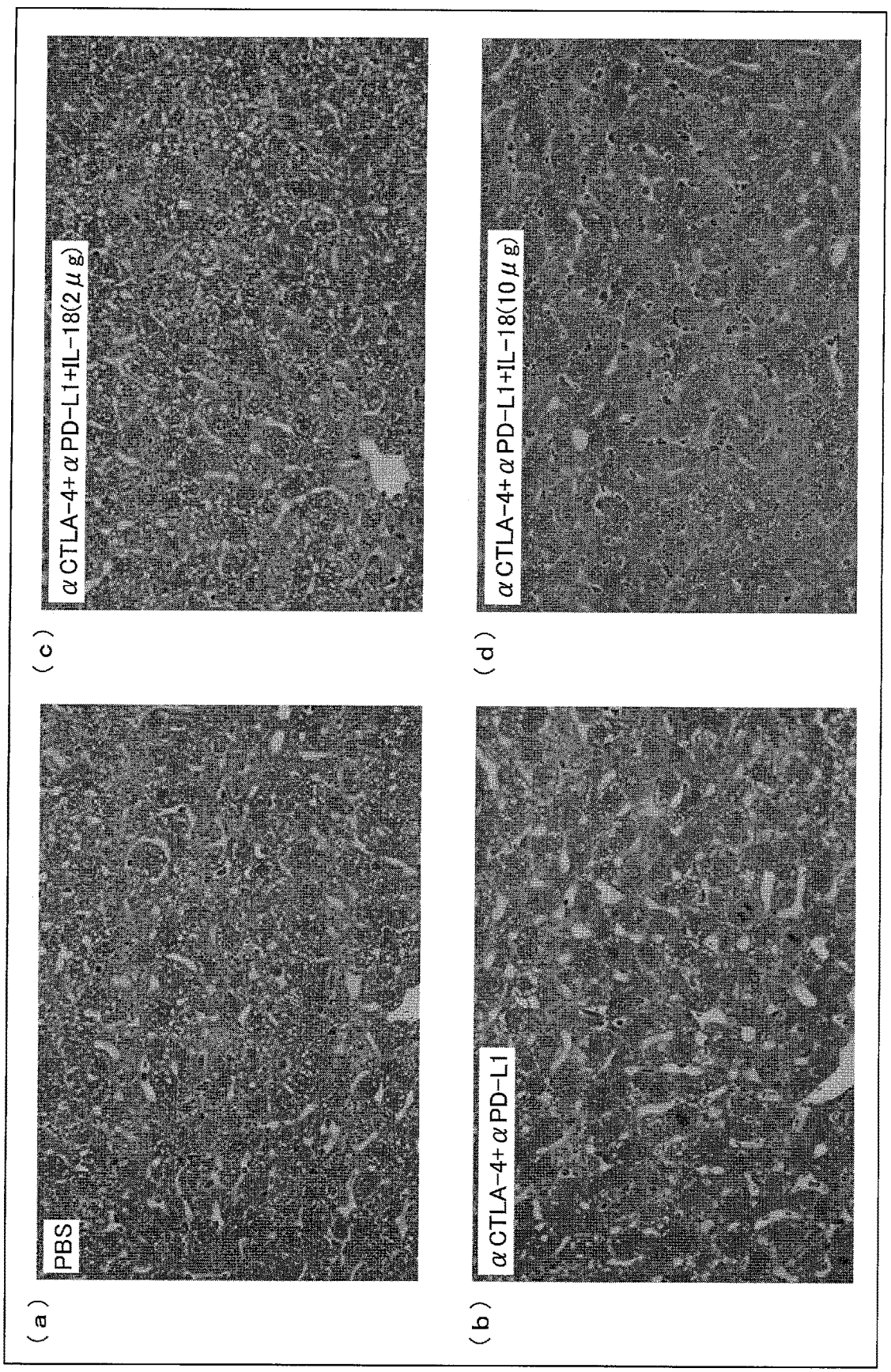
FIG. 28 is a view showing results of tissue staining of livers of the mice in the groups 1 to 4 with hematoxylin eosin (HE) in Example 16. (a) to (d) show results of tissue staining of livers of the mice in the groups 1 to 4, respectively, of Example 16 with hematoxylin eosin (HE).

(b) of FIG. 28 shows results of observations of the liver tissues in the group 2. In all the mice in the group 2, many mitotic figures as in (b) of FIG. 28 were observed. The results shown in (a) of FIG. 25 and (b) of FIG. 28 indicate the possibility that the anti-CTLA-4 antibody and the anti-PD-L1 antibody may produce adverse reactions such as liver tissue disorder.

Further, as shown by "αCTLA-4+αPD-L1" in (b) of FIG. 26, the group 2 exhibits a tendency toward a high blood creatinine concentration. Thus, it is conceivable that the anti-CTLA-4 antibody and the anti-PD-L1 antibody may also have caused a mild disorder of the kidney.

In contrast, the groups administered with a combination of the anti-CTLA-4 antibody, the anti-PD-L1 antibody, and IL-18 (groups 3 and 4) had blood albumin concentration nearly equal to that of the healthy mice, as shown in (a) of FIG. 25. Moreover, as shown in (c) and (d) of FIG. 28, mitotic figures in the liver tissues were not found. Furthermore, as shown in (b) of FIG. 26, the groups 3 and 4 had blood creatinine concentration nearly equal to that of the healthy control group. The group 3 exhibited a tendency toward decreased urea nitrogen in the blood, as shown in FIG. 27.

As shown in (c) of FIG. 26 and (d) of FIG. 25, values of the blood ALP and blood ALT (GPT) were remarkably low in the group inoculated with the cancer cells without being subjected to treatment (the group 1 represented by "PBS" in FIGS. 25 and 26), although the values of the blood ALP and blood ALT (GPT) in the groups 3 and 4 were close to those in the healthy control group. In contrast, the blood ALP in the group 2 was approximately the same as that in the group 1, and the blood ALT (GPT) in the group 2 was remarkably lower than that in the group 1. The results shown in (c) of FIG. 26 and (d) of FIG. 25 suggested that the values of the blood ALP and blood ALT (GPT) were improved by IL-18 in the groups 3 and 4.

The results in Example 16 show the possibility that the combination of the anti-CTLA-4 antibody and the anti-PD-L1 antibody can cause, as adverse reactions, disorders of liver, kidney, and other organs, and suggest that IL-18 can suppress the above adverse reactions or promote repair of the disorders. In the future, a further study will be required to determine, for example, which one of the anti-CTLA-4 antibody and the anti-PD-L1 antibody is associated with tissue disorders.

As described above, albumin, ALT (GPT), and ALP concentrations in blood were much lower in the group 2 than in the healthy control group, and creatinine concentration in blood was much higher in the group 2 than in the healthy control group. In contrast, the groups 3 and 4 exhibited the following tendencies. The group 4 exhibited the tendency toward increased AST (GOT) in comparison with the healthy control group ((c) of FIG. 25), while the group 3 exhibited the tendency toward decreased urea nitrogen in comparison with the healthy control group (FIG. 27). Further, uric acid concentration was higher in the groups 3 and 4 than in the healthy control group ((d) of FIG. 26).

However, of the 9 items shown in FIGS. 25 to 27, 4 items in the group 2 were significantly deviated from those in the healthy control group, and both the group 3 and the group 4 fell behind the healthy control group in terms of uric acid only. With all the things considered, the therapeutic agents used for the groups 3 and 4 are presumed to cause fewer adverse reactions than the therapeutic agent used for the group 2.

Figure 29:
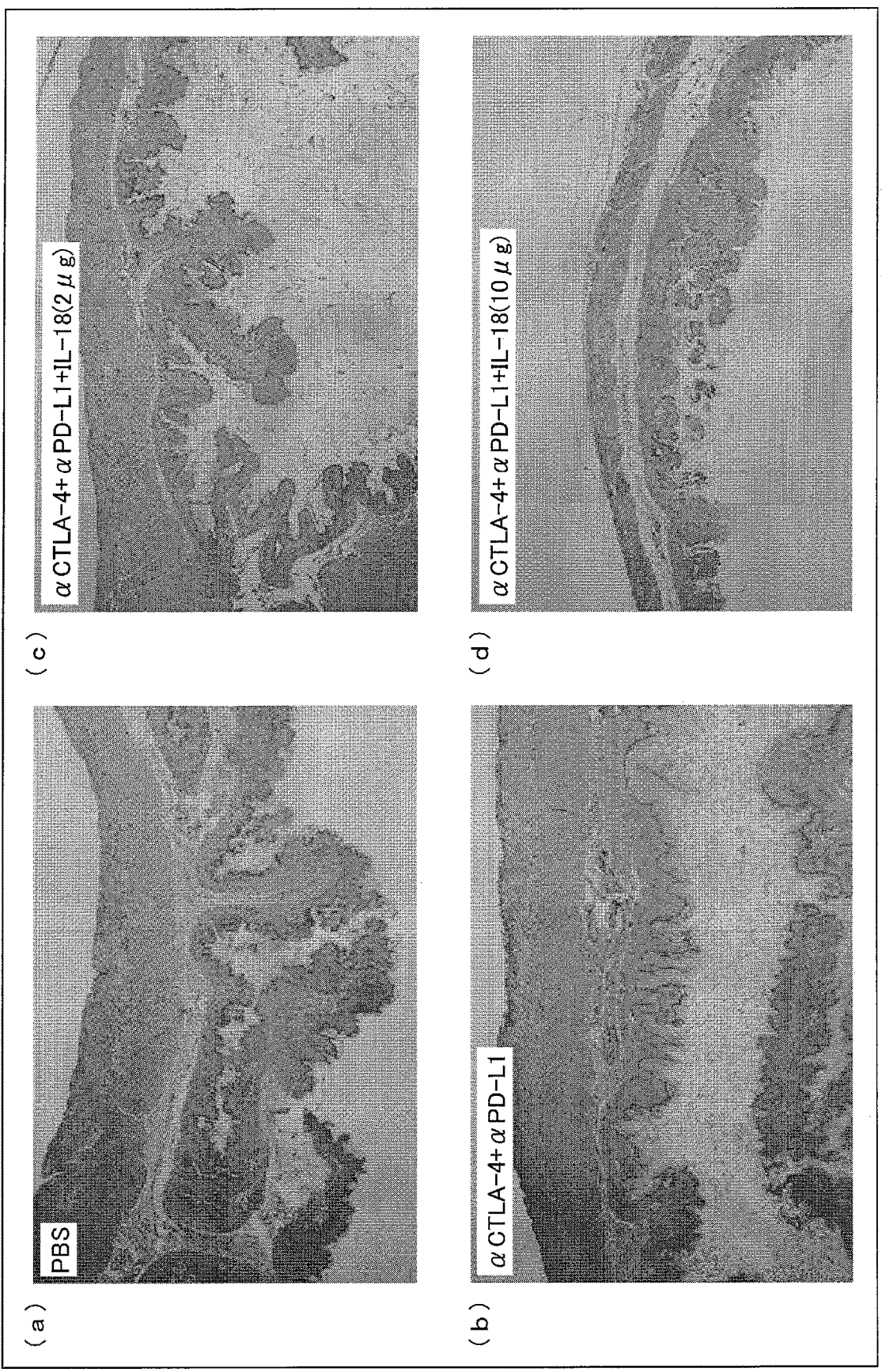
FIG. 29 is a view showing results of tissue staining of stomachs of the mice in the groups 1 to 4 with hematoxylin eosin (HE) in Example 16. (a) to (d) show results of tissue staining of stomachs of the mice in the groups 1 to 4, respectively, of Example 16 with hematoxylin eosin (HE).
Figure 30:
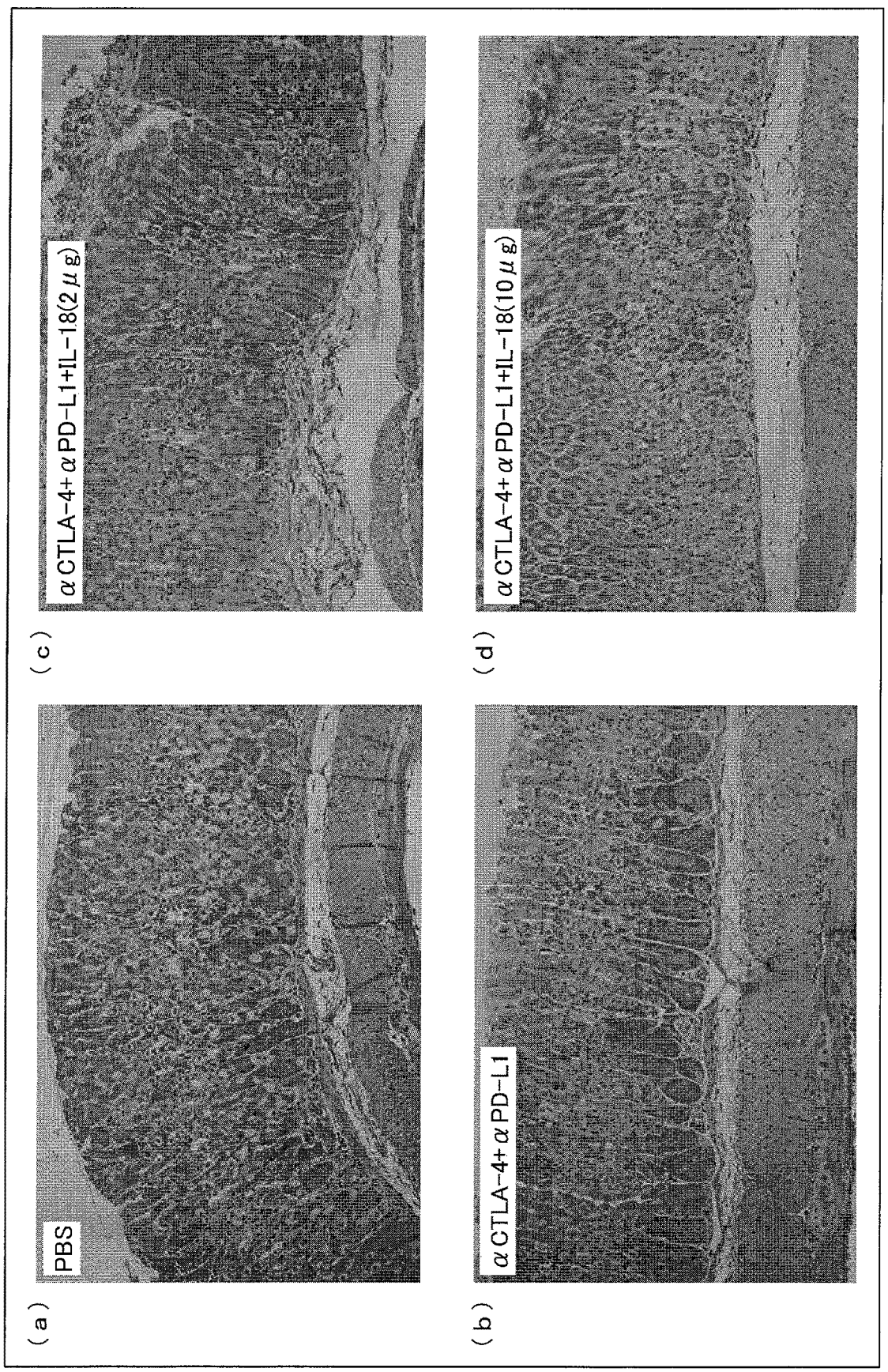
FIG. 30 is a view showing results of tissue staining of stomachs of the mice in the groups 1 to 4 with hematoxylin eosin (HE) in Example 16. (a) to (d) show results of tissue staining of stomachs of the mice in the groups 1 to 4, respectively, of Example 16 with hematoxylin eosin (HE).
Figure 31:
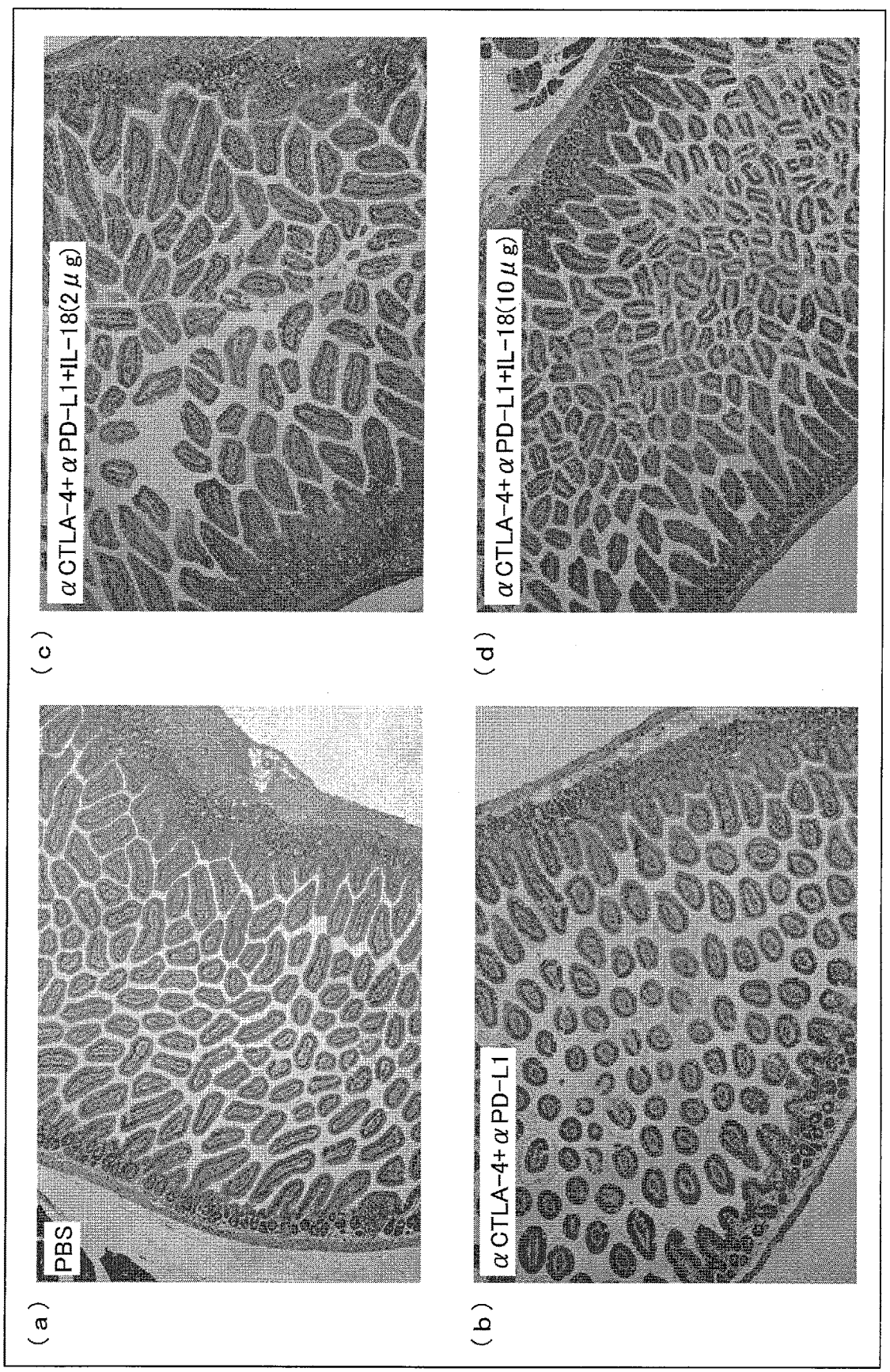
FIG. 31 is a view showing results of tissue staining of duodenums of the mice in the groups 1 to 4 with hematoxylin eosin (HE) in Example 16. (a) to (d) show results of tissue staining of duodenums of the mice in the groups 1 to 4, respectively, of Example 16 with hematoxylin eosin (HE).
Figure 32:
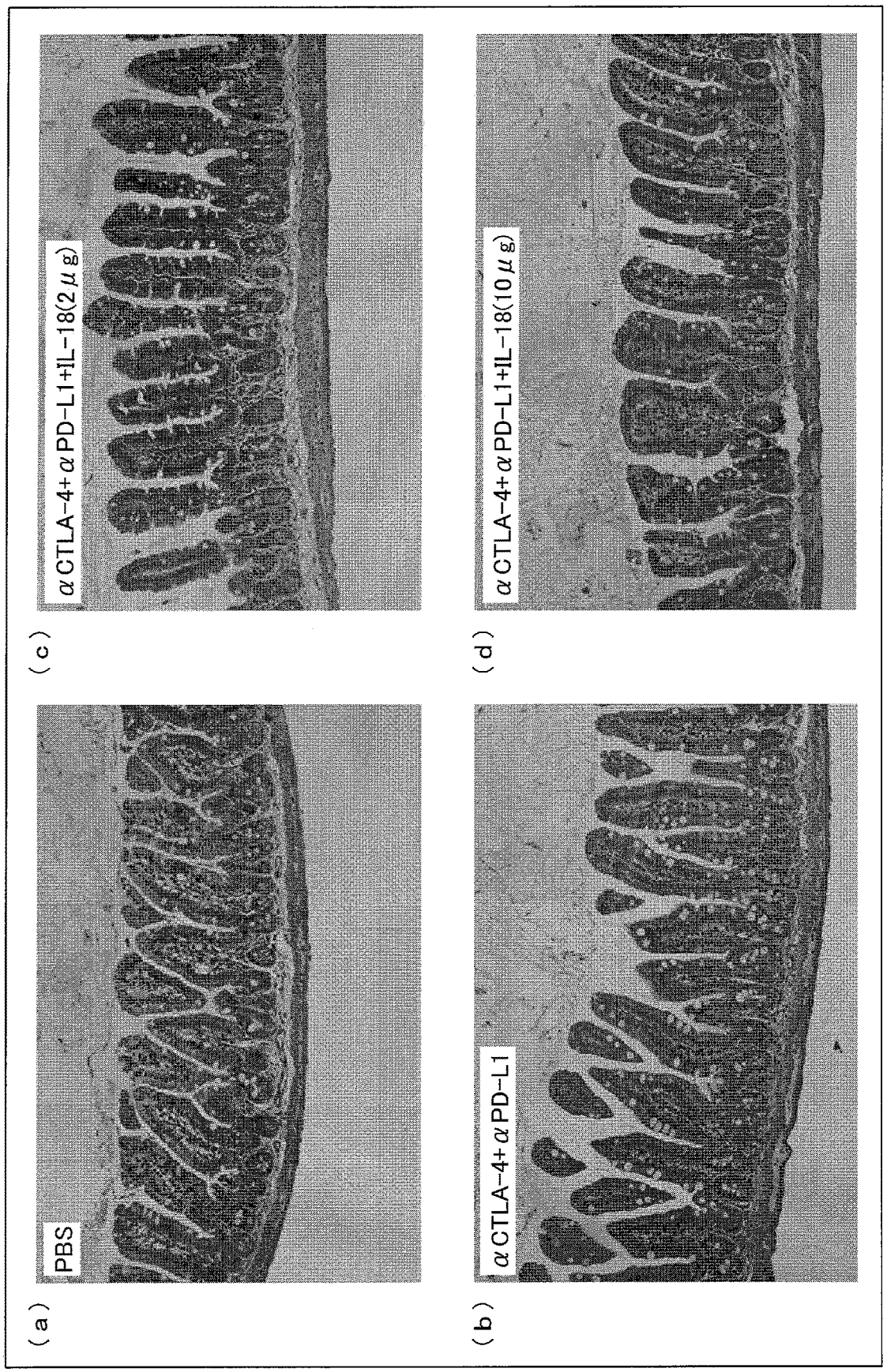
FIG. 32 is a view showing results of tissue staining of small intestines of the mice in the groups 1 to 4 with hematoxylin eosin (HE) in Example 16. (a) to (d) show results of tissue staining of small intestines of the mice in the groups 1 to 4, respectively, of Example 16 with hematoxylin eosin (HE).
Figure 33:
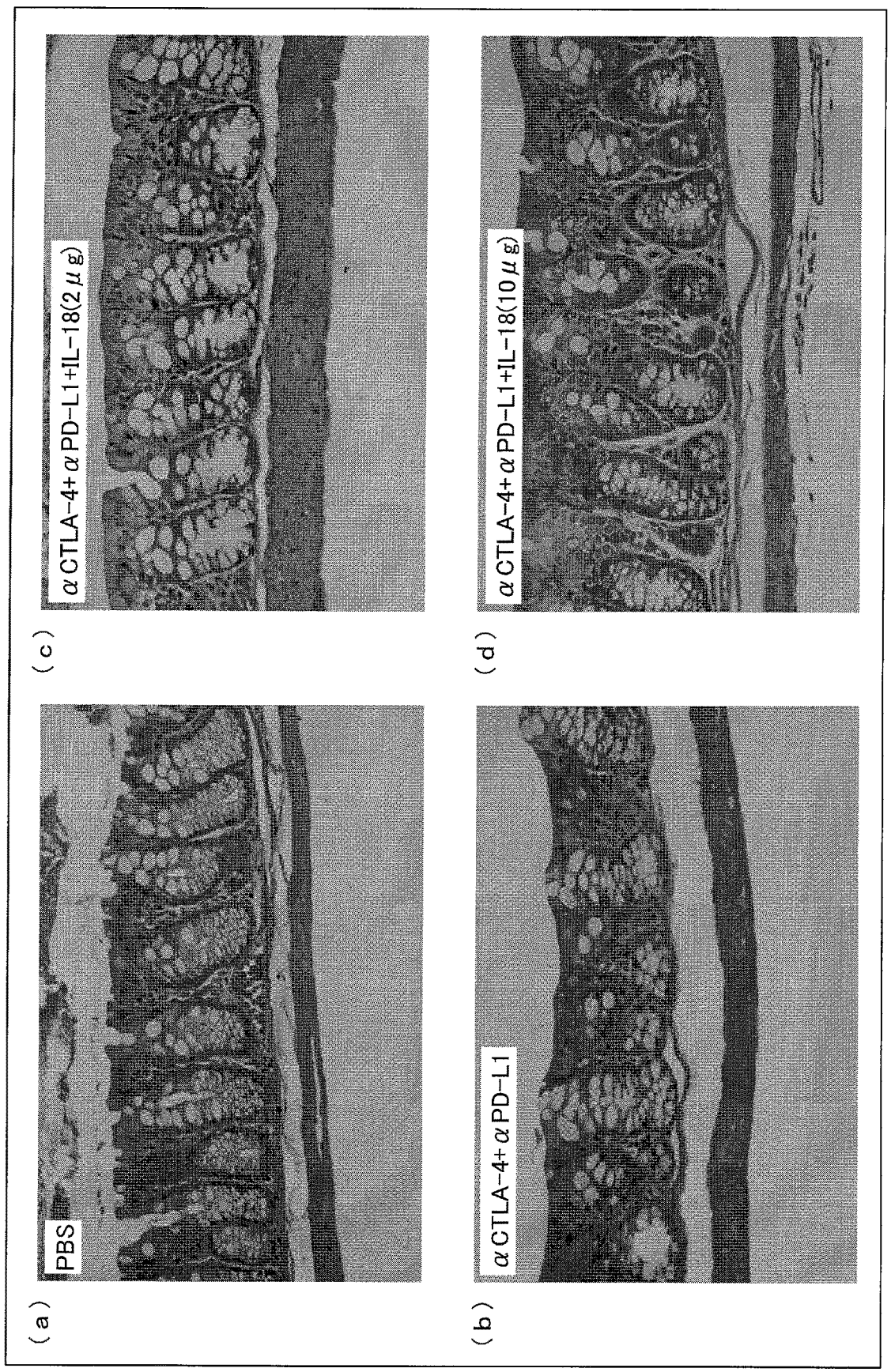
FIG. 33 is a view showing results of tissue staining of large intestines of the mice in the groups 1 to 4 with hematoxylin eosin (HE) in Example 16. (a) to (d) show results of tissue staining of large intestines of the mice in the groups 1 to 4, respectively, of Example 16 with hematoxylin eosin (HE).
Figure 34:
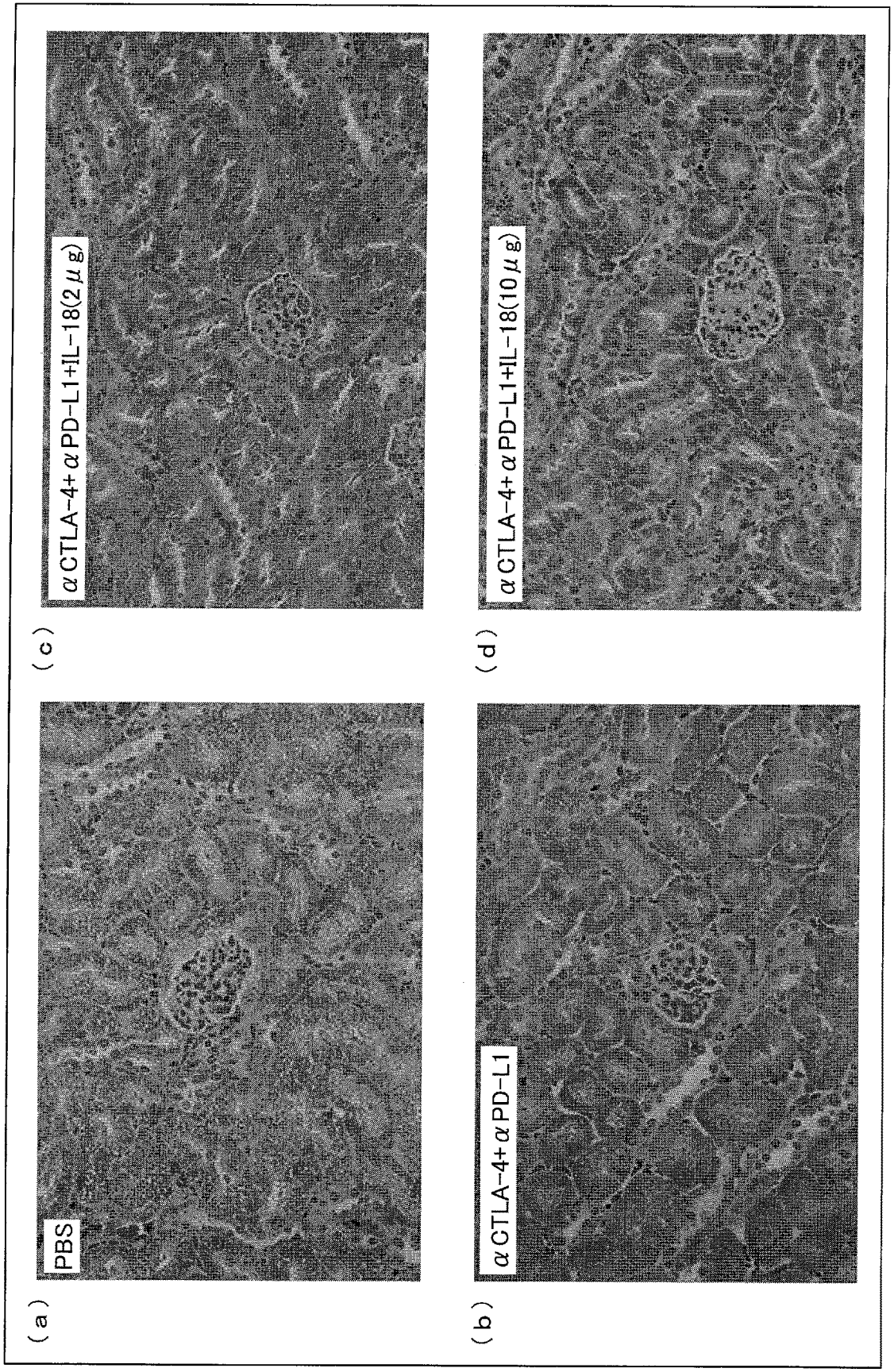
FIG. 34 is a view showing results of tissue staining of kidneys of the mice in the groups 1 to 4 with hematoxylin eosin (HE) in Example 16. (a) to (d) show results of tissue staining of kidneys of the mice in the groups 1 to 4, respectively, of Example 16 with hematoxylin eosin (HE).

FIGS. 29 and 30 show results of tissue staining of stomachs with hematoxylin eosin (HE). FIG. 31 shows results of tissue staining of duodenums with hematoxylin eosin (HE). FIG. 32 shows results of tissue staining of small intestines with hematoxylin eosin (HE). FIG. 33 shows results of tissue staining of large intestines with hematoxylin eosin (HE). FIG. 34 shows results of tissue staining of kidneys with hematoxylin eosin (HE). In FIGS. 29 to 34, (a) to (d) show results of observations of tissues of the mice in the groups 1 to 4, respectively. As can be seen from FIGS. 29 to 34, almost no differences between the groups 1 to 4 were found in the tissues of the stomach, duodenum, small intestine, large intestine, and kidney tissues.

Example 17: Effect of Cancer Therapeutic Agent on Metastasis of B16 Melanoma Cells B16 melanoma cells (melanoma) are often used as a metastasis model of cancer. In Example 17, B16 melanoma cells ($2 \times 10^5$ cells) were transferred into mice (C57BL/6, Japan SLC) from their tail veins. Several weeks later, the degree of metastasis was measured by counting the number of black nodules formed in lungs.

A cell line of B16 melanoma cells purchased from ATCC was used. By a method similar to that described in Example 1, a suspension in a cell concentration of $2 \times 10^5$ cells per 0.25 ml was prepared and was injected into the tail vein of each of the C57BL/6 mice in an amount of 0.25 ml.

The mice were divided into a control group to which 0.25 ml of PBS was to be administered as a therapeutic agent (group 1); a group to which 100 μg of anti-CTLA-4 antibody and 200 μg of anti-PD-L1 antibody were to be administered as a therapeutic agent (group 2); and a group to which 100 μg of anti-CTLA-4 antibody, 200 μg of anti-PD-L1 antibody, and IL-18 (2 μg) were to be administered as a therapeutic agent (group 3). Each of the groups was made up of four mice. It should be noted that each of the doses (μg) of the PBS, the anti-CTLA-4 antibody, the anti-PD-L1 antibody, and IL-18 is a dose per 25 g of a body weight of a mouse.

Figure 35:
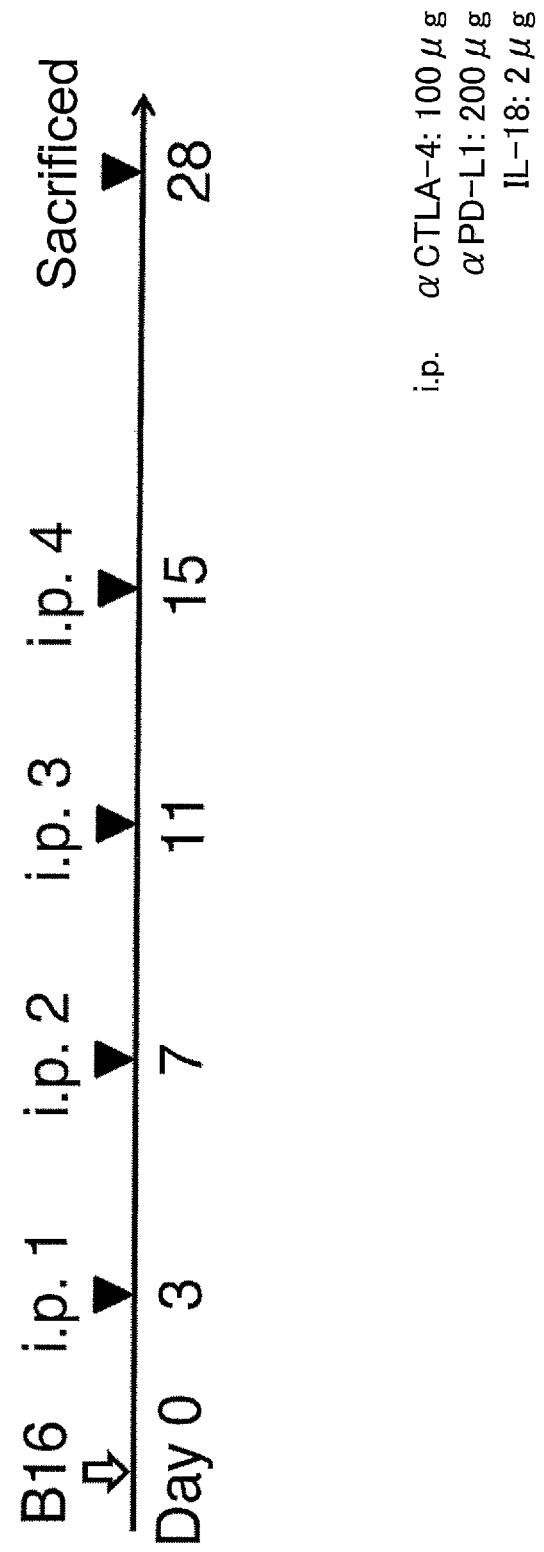
FIG. 35 is a view illustrating schedules, in Example 17, for inoculation of B16 melanoma cells and for administration of each of the therapeutic agents.

FIG. 35 is a view illustrating schedules for the inoculation of the B16 melanoma cells and for the administration of each of the therapeutic agents, and illustrating that each of the therapeutic agents was intraperitoneally administered 3 days, 7 days, 11 days, and 15 days after "Day 0", which is the day of inoculation of the B16 melanoma cells, and the mice were sacrificed 28 days after "Day 0".

Figure 36:
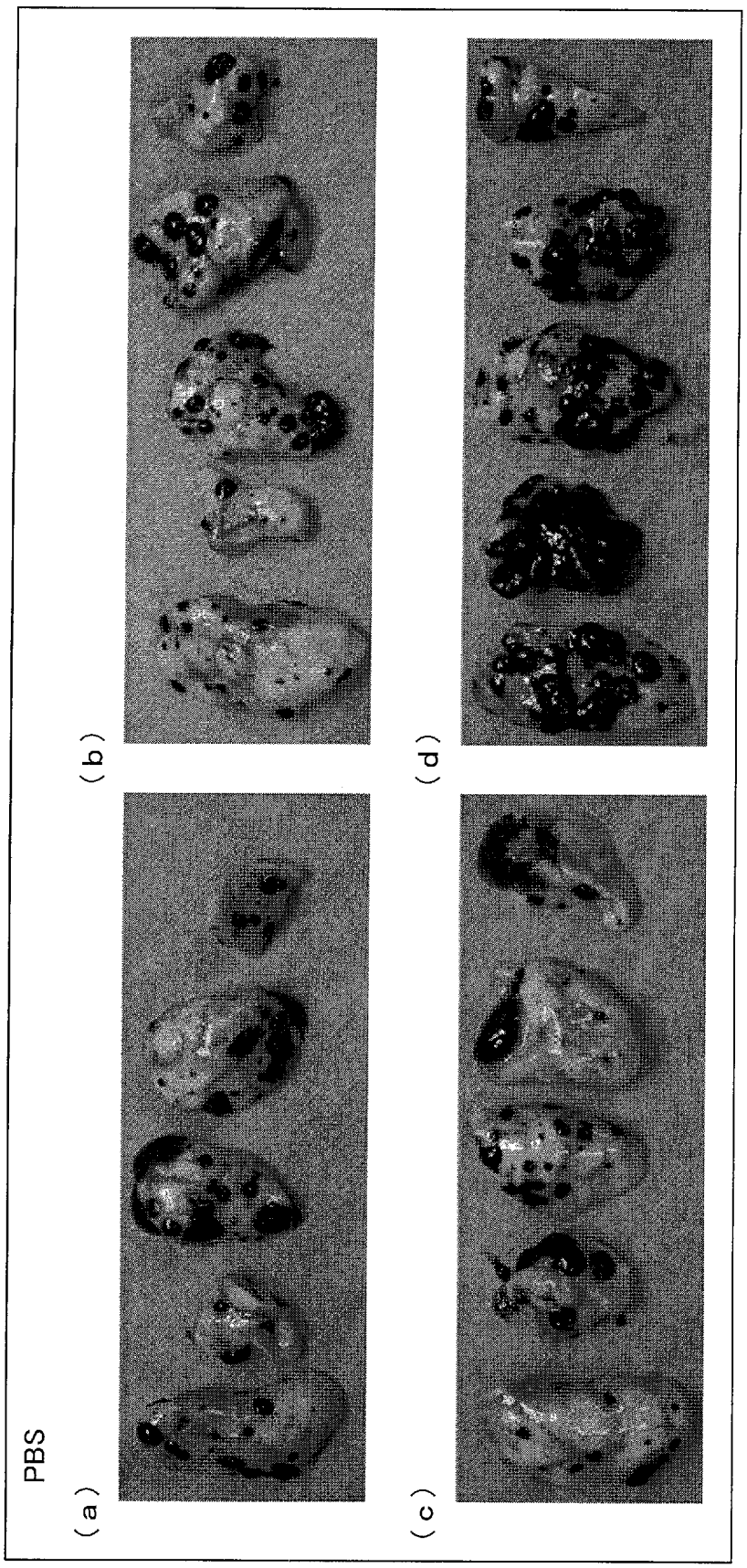
FIG. 36 is a set of views showing results of observations of nodules formed in the lungs of the mice in the group 1 in Example 17. (a) to (d) show respective results for the four experimental mice.
Figure 37:
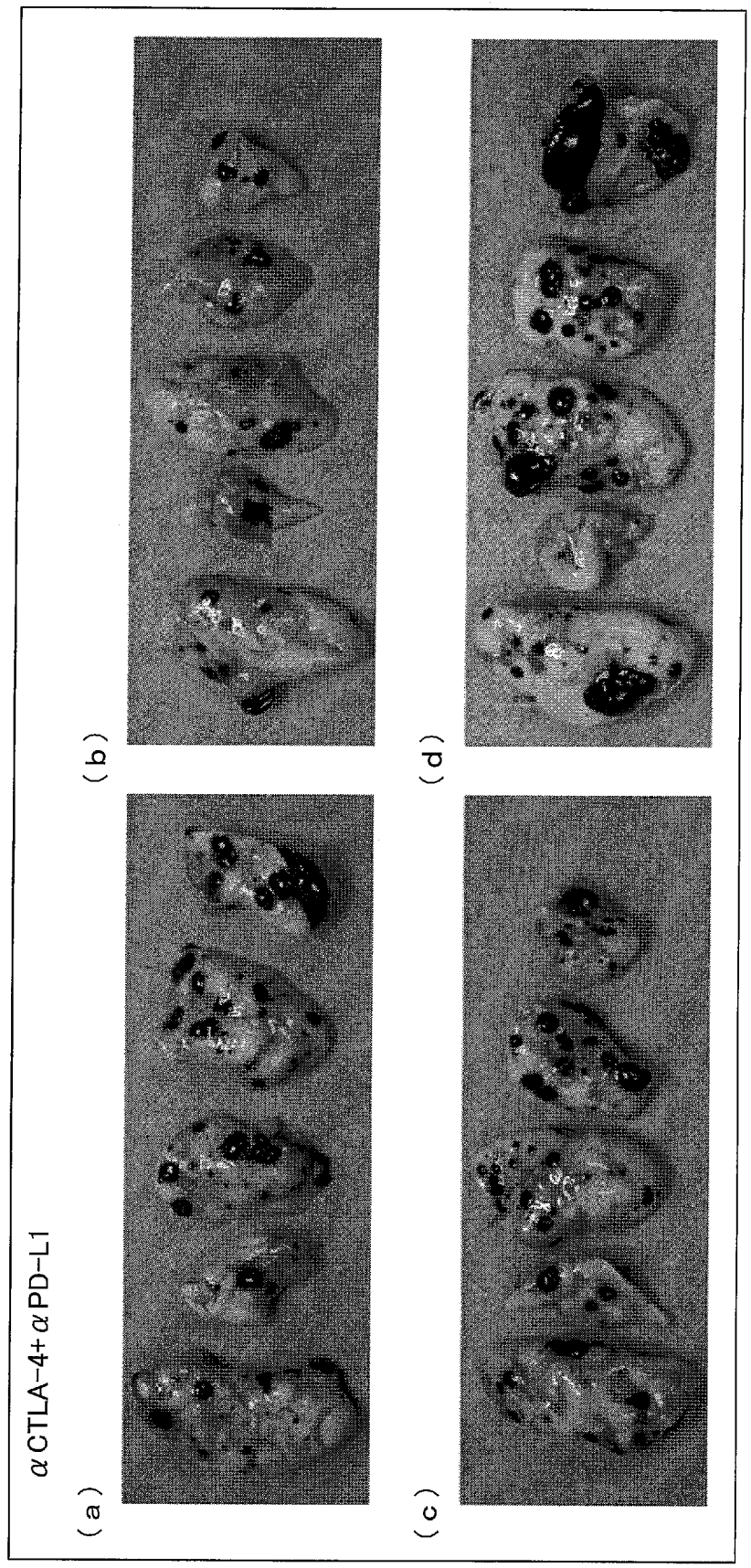
FIG. 37 is a set of views showing results of observations of nodules formed in the lungs of the mice in the group 2 in Example 17. (a) to (d) show respective results for the four experimental mice.
Figure 38:
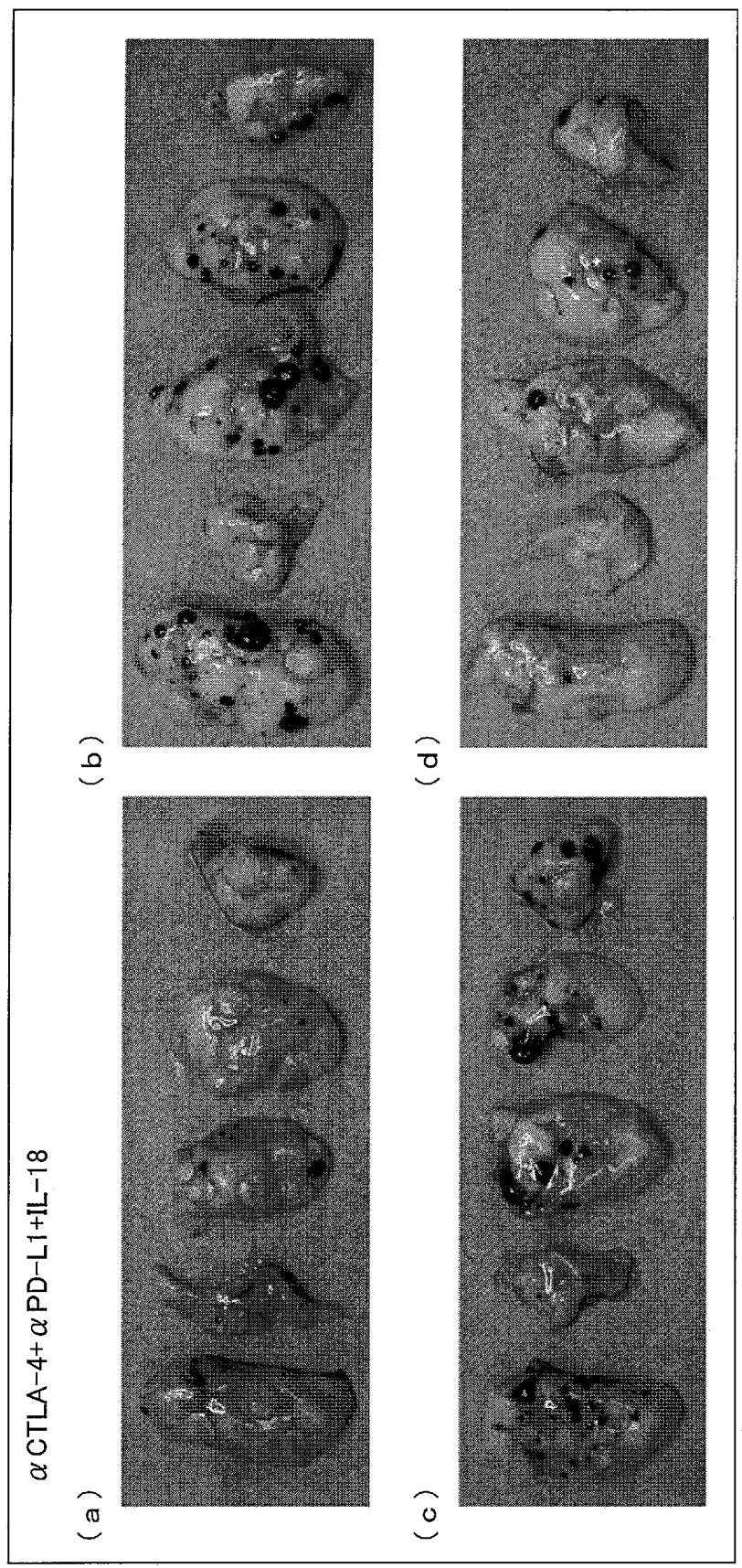
FIG. 38 is a set of views showing results of observations of nodules formed in the lungs of the mice in the group 3 in Example 17. (a) to (d) show respective results for the four experimental mice.

Lungs were excised from the sacrificed mice. Then, the degree of metastasis was measured by counting the number of black nodules formed in the lungs. FIGS. 36 to 38 are views showing results of observations of the nodules formed in the lungs of the mice in the groups 1 to 3, wherein (a) to (d) of FIGS. 36 to 38 show respective results for the four experimental mice.

In the control group (the above group 1), the number of nodules on surfaces of the lungs averaged 233±22.6. In the group administered with the anti-CTLA4 antibody and the anti-PD-L1 antibody every four days, 4 times in total, 3 days after the day of inoculation of the B16 melanoma cells (the above group 2), the number of nodules on surfaces of the lungs averaged 179±14.0. In the group administered with the anti-CTLA4 antibody, the anti-PD-L1 antibody, and IL-18 (the above group 3) the number of nodules on surfaces of the lungs averaged 121±42.7.

The result for the group 3 did not show a statistically significant difference from to the result for the group 2. However, as can be seen from comparison between FIG. 37 and FIG. 38, the group 3 suppressed organ metastasis in comparison with the group 2. From this result, it is considered quite possible that the significant difference would be shown if more mice were subjected to the experiment (although the four mice was subjected to the experiment in Example 17) or if, as in Example 1, the survival rate of the mice was determined with time since the day of inoculation of the B16 melanoma cells.

In the group 3, there was no difference between a therapeutic effect obtained in a case where the anti-CTLA4 antibody and the anti-PD-L1 antibody were intraperitoneally administered, but IL-18 was hypodermically administered and a therapeutic effect obtained in a case where those antibodies and IL-18 were intraperitoneally administrated concurrently. This is presumed to occur because the above antibodies and IL-18 are moved together into blood. That is why the same effect was provided regardless of administration route.

[Recap]

As shown in the Examples, it was revealed that the cancer therapeutic agent according to an embodiment of the present invention provides a very excellent antitumor effect in a cancer peritoneal dissemination model by using at least one molecular-targeted antibody, such as the anti-CTLA-4 antibody and the anti-PD-L1 antibody, and IL-18 in combination. Besides, strong antitumor effects were also provided similarly in a lung metastasis model and in a solid cancer model. This is presumed to occur because IL-18 remarkably enhances the therapeutic effect of the molecular-targeted antibody (antibodies).

Specifically, it is presumed that IL-18 enhances the therapeutic effect of the molecular-targeted antibody (antibodies) by promoting activation and growth of effector cells, such as CD8-positive T cells and NK cells, in an abdominal cavity of a mouse into which tumor cells have been transferred.

Particularly, it is suggested that IL-18 increases B220-positive, DX5-positive, CD11c-positive NK-like cells (referred to as "IKDC", which is an abbreviation for Interferon introducing killer dendritic cells), and the increased B220-positive, DX5-positive, CD11c-positive NK-like cells are associated with enhancement of the antitumor effect provided by the above combination.

Meanwhile, the above combination inhibits growth of CD4-positive T cells. Because of this, it is not considered that the above combination promotes growth of lymphocytes having an immunosuppressive action and/or an inflammation inhibiting action, such as Treg.

Further, the mouse administered with the anti-CTLA-4 antibody and/or the anti-PD-L1 antibody, and IL-18 was in good health, and did not show body weight loss or other symptom. Moreover, strong autoimmune-like lesions were not found in the intestines and other organs. Furthermore, results of the study on liver function, renal function, and tissue lesions confirmed that the cancer therapeutic agent according to an embodiment of the present invention is considered to produce few adverse reactions.

Consequently, it can be said that the cancer therapeutic agent according to an embodiment of the present invention is a useful therapeutic agent that provides an excellent antitumor effect. Particularly, it can be said that the cancer therapeutic agent according to an embodiment of the present invention is effective in treating cancer associated with peritoneal dissemination.

INDUSTRIAL APPLICABILITY

The present invention can be effectively used for treatment of a cancer, and in particular, to treatment of a cancer associated with peritoneal dissemination. The present invention can be widely used in the field of pharmaceuticals and its relevant fields.

The invention claimed is:

1. A method for treating a cancer, comprising of:
(a) administering, to a patient, a composition comprising an IL-18 polypeptide selected from the group consisting of SEQ ID NOs: 1 and 2; and one or more antibodies selected from the group consisting of an anti-PD-L1 antibody and an anti-CTLA-4 antibody, and the composition further comprises a pharmaceutically acceptable carrier, a diluent, a moisture retention agent or an emulsifier, a pH buffer, a binder, or an excipient, or
(b) administering, to a patient, a first composition comprising an IL-18 polypeptide selected from the group consisting of SEQ ID NOs: 1 and 2; and a second composition comprising of one or more antibodies selected from the group consisting of an anti-PD-L1 antibody and an anti-CTLA-4 antibody; wherein the IL-18 polypeptide and the one or more said antibodies being administered separately or simultaneously, and the first and second composition further comprises a pharmaceutically acceptable carrier, a diluent, a moisture retention agent or an emulsifier, a pH buffer, a binder, or an excipient;

wherein only the IL-18 polypeptide and the one or more antibodies being active ingredients,
a mass of the IL-18 polypeptide and a sum of a mass(es) of the one or more antibodies being in a ratio of 1:25 to 1:100,
the anti-CTLA-4 antibody being an anti-human CTLA-4 antibody, or an anti-mouse CTLA-4 antibody,
the cancer being one or more cancers selected from the group consisting of adenocarcinomas, osteosarcoma, and leukemia.

2. The method according to claim 1, wherein the cancer is adenocarcinomas.

3. The method according to claim 2, wherein the cancer is selected from the group consisting of prostate cancer, small intestine cancer, endometrium cancer, cervical canal cancer, large intestine cancer, lung cancer, pancreas cancer, gullet cancer, intestinum rectum cancer, uterus cancer, gastric cancer, breast cancer, and ovary cancer.

4. The method according to claim 1, wherein the cancer is one or more cancers selected from the group consisting of osteosarcoma and leukemia.

* * * * *

UNITED STATES PATENT AND TRADEMARK OFFICE
CERTIFICATE OF CORRECTION

PATENT NO. : 11,219,672 B2
APPLICATION NO. : 15/501760
DATED : January 11, 2022
INVENTOR(S) : Haruki Okamura, Kyosuke Yamanishi and Wen Li Page 1 of 1

It is certified that error appears in the above-identified patent and that said Letters Patent is hereby corrected as shown below:

On the Title Page

Item (73) should read:
(73) Assignees: Haruki Okamura, Osaka (JP);
Kyosuke Yamanishi, Hyogo (JP);
Yoshimasa Tanaka, Nagasaki (JP);
MEDICAL RESEARCH AND DEVELOPMENT CORPORATION, Aichi (JP);
FOUNDATION FOR BIOMEDICAL RESEARCH AND INNOVATION AT KOBE, Hyogo (JP)

Signed and Sealed this
Eleventh Day of October, 2022

Katherine Kelly Vidal
*Director of the United States Patent and Trademark Office*